(12) United States Patent
Lindner et al.

(10) Patent No.: US 6,630,325 B1
(45) Date of Patent: Oct. 7, 2003

(54) COMPOSITIONS, METHODS AND KITS RELATING TO REMODEL

(75) Inventors: Volkhard Lindner, South Portland, ME (US); Robert E. Friesel, Cape Elizabeth, ME (US)

(73) Assignee: Maine Medical Center Research Institute, Scarborough, ME (US)

( * ) Notice: Subject to any disclaimer, the term of this patent is extended or adjusted under 35 U.S.C. 154(b) by 25 days.

(21) Appl. No.: 09/692,081

(22) Filed: Oct. 19, 2000

(51) Int. Cl.$^7$ .......................... C12P 21/06; C12N 15/87; C12N 1/20; C12N 15/00; C07H 21/04
(52) U.S. Cl. ..................... 435/69.1; 536/23.5; 435/455; 435/252.3; 435/320.1
(58) Field of Search ........................ 536/23.5; 435/69.1, 435/455, 252.3, 320.1

(56) References Cited

U.S. PATENT DOCUMENTS 6,210,663 B1 * 4/2001 Ertl

FOREIGN PATENT DOCUMENTS

WO    WO 98/54963    * 12/1998

OTHER PUBLICATIONS

Wallace RW. Does antisense make sense? Drug Discov Today. vol. 4(1):4–5, 1999.*
Attwood TK. Genomics. The Babel of bioinformatics. Science. 290(5491):471–473, 2000.*
Skolnick et al. From genes to protein structure and function: novel applications of computational approaches in the genomic era. Trends Biotechnol. 18(1):34–9, 2000.*
Matunis MJ, Wu J, Blobel G. SUMO–1 modification and its role in targeting the Ran GTPase–activating protein, RanGAP1, to the nuclear pore complex. J Cell Biol. 9;140(3):499–509, 1998.*
Darnell et al. Molecular Cell Biology. New York: W H Freeman & Co; pp. 248–255, 1986.*
Battegay et al., 1990, Cell 63:515–524.
Bray et al., 1998, Hypertension 31:986–994.
Calés et al., 1998, Biomed. Pharmacother. 52:259–263.
Chipev et al., 2000, Cell Death Differ. 7:166–176.
Darby et al, 1990, Lab. Invest. 63:21–29.
Desmouliere et al., 1993, J. Cell Biol. 122:103–111.
Desmouliere et al., 1995, Am. J. Pathol. 146:56–66.
Desmouliere et al., 1997, Int.J.Biochem. Cell Biol. 29:19–30.
Einhorn et al., 1998, Clin. Orthop. S7–21.
Grainger et al., 1994, Biochem. J. 299:227–235.
Halloran et al., 1995, Am. J. Surg. 170:193–197.
Herbert and Carmeliet, 1997, FEBS Lett. 413:401–404.
Kakuta et al., 1994, Circulation 89:2809–2815.
Khalil et al., 1996, Am. J. Respir. Cell Mol. Biol. 14:131–138.
Koyama et al., 1990, Biochem. Biophys. Res. Commun. 169:725–729.
Kurihara et al., 1989, Biochem. Biophys. Res. Commun. 159:1435–1440.
Lindner and Reidy 1993, Circ. Res. 73:589–595.
Majesky et al., 1991, J. Clin. Invest. 88:904–910.
McCaffrey et al., 1995 J. Clin. Invest. 96:2667–2675.
Messadi et al., 1999, Wound Repair Regen 7:511–517.
Mii et al., 1993, Surgery 114:464–470.
Mintz et al., 1993, Circulation 88:I–654 (Abstract No. 3523).
Mintz et al., 1994, Circulation 90:I–24 (Abstract No. 0117).
Neilson and Friesel, 1996, J. Biol. Chem. 271:25049–25057.
Nikol et al., 1992, J. Clin. Invest. 90:1582–1592.
Nunes et al., 1995, Arterioscler. Thromb. Vasc. Biol. 15:156–165.
Olmedo et al., 1999, J. Orthop. Trauma 13:356–362.
Orlandi et al., 1994, Exp. Cell Res. 214:528–536.
Pelton et al., 1991, Am. J. Respir. Cell Mol. Biol. 5:522–530.
Perella et al., 1996, J. Biol. Chem. 271:13776–13780.
Reddy and Howe, 1993, J. Cell Physiol. 156:48–55.
Scott et al., 1996, Circulation 93:2178–2187.
Shi et al., 1996 Arterioscler. Thromb. Vasc. Biol. 16:1298–1305.
Shi et al., 1996, Circulation 93:340–348.
Shulick et al., 1998, Proc. Natl. Acad. Sci. USA 95:6983–6988.
Smith et al., 1999, Circ. Res. 84:1212–1222.
Stouffer and Owens, 1994, J. Clin. Invest. 93:2048–2055.
Takemura et al., 1998, Circ. Res. 82:1130–1138.
Verbeek et al., 1994, Am J. Pathol. 144:372–382.
Wang et al., 1999, Thorax 54:805–812.
Ward et al., 1997, Arterioscler. Thromb. Vasc. Biol. 17:2461–2470.
Wilcox et al. 1997, Ann. N.Y. Acad. Sci. 811:437–447.
Wolf et al., 1994, J. Clin. Invest. 93:1172–1178.

* cited by examiner

*Primary Examiner*—Christina Chan
*Assistant Examiner*—Maher Haddad
(74) *Attorney, Agent, or Firm*—Morgan, Lewis & Bockius, LLP

(57) ABSTRACT

The invention relates to novel nucleic acids encoding a mammalian adventitia inducible and bone expressed gene designated REMODEL, and proteins encoded thereby, whose expression is increased in certain diseases, disorders, or conditions, including, but not limited to, negative remodeling, arterial restenosis, vessel injury, ectopic ossification, fibrosis, and the like. REMODEL also plays a role in cell-cell and cell-matrix adhesion, bone density, bone formation, dorsal closure, and is associated with spina bifida-like phenotype. The invention further relates to methods of treating and detecting these diseases, disorders or conditions, comprising modulating or detecting REMODEL expression and/or production of REMODEL polypeptide.

11 Claims, 15 Drawing Sheets

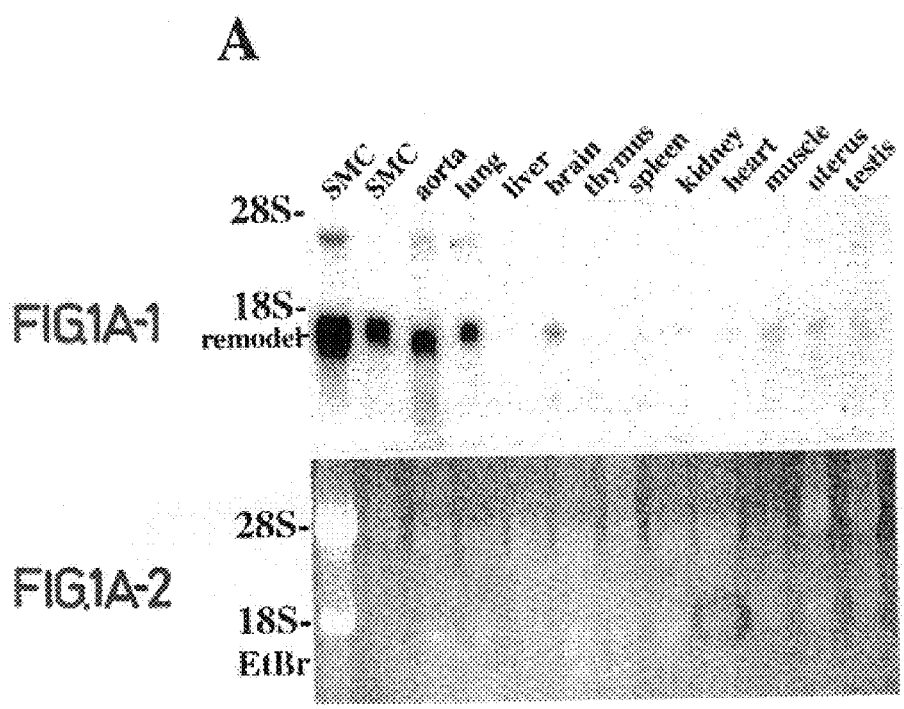
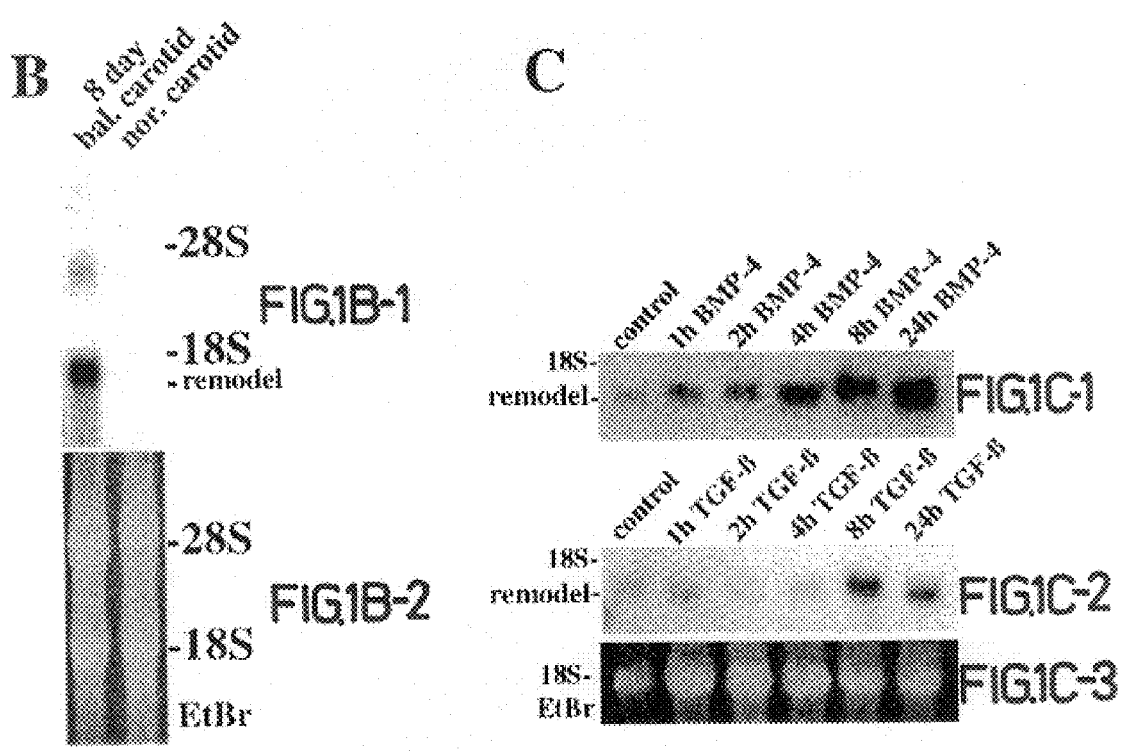

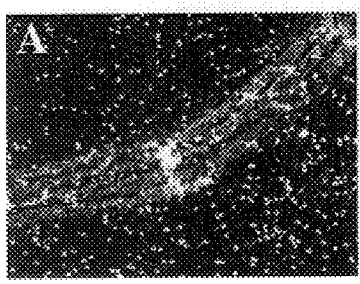
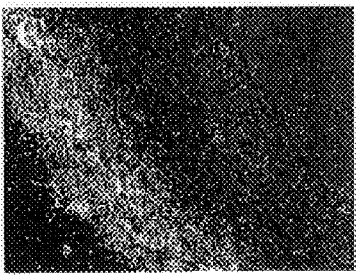
FIG.2A  FIG.2B  FIG.2C
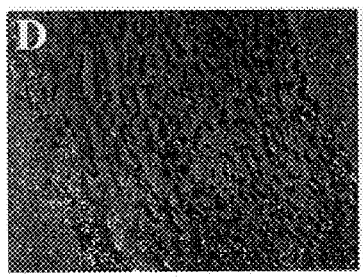
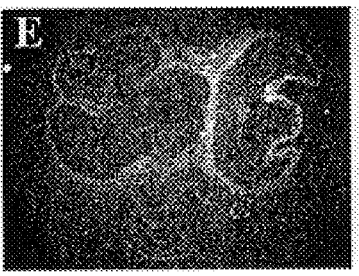
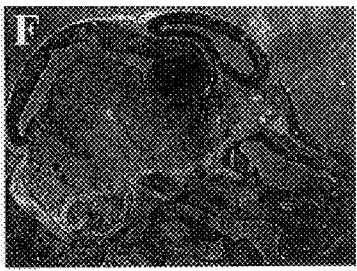
FIG.2D  FIG.2E  FIG.2F
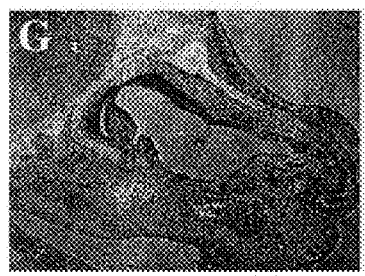
FIG.2G  FIG.2H  FIG.2I
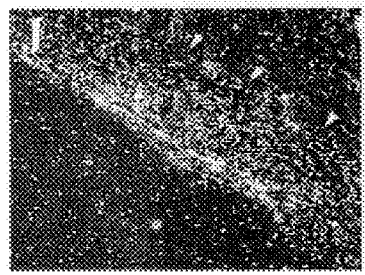
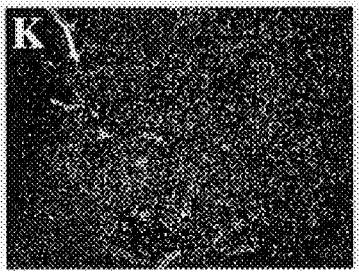
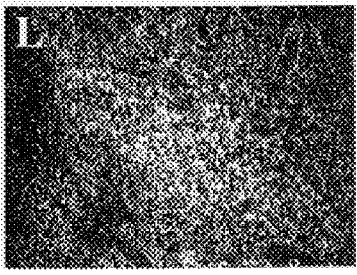
FIG.2J  FIG.2K  FIG.2L

```
              30         40         50         60         70
Rat   ATGCGGCCGGCCGCAGAGCTGGGC-----CAGACGCTGAGCAGGGCCGGGCTCTGCCGAC
Human ACGAGGGCGGCCTCGGAGCGCGGCGGAGCCAGACGCTGACCACGTTCCT-CTCCTCGGTC
               10         20         30         40         50         60
         80         90        100        110        120        130
Rat   CCCTTTGCCTCCTGCTCTGCGCTTCGCAGCTACCGCACACGATGCACCCCAAGGCCGCG
Human TCCTCCGCCTCCAGCTCCGCGCTGCCCGGCAGCCGGGAGCCATGCGACCCCAGGGCCCCG
              70         80         90        100        110        120
        140        150        160        170        180        190
Rat   CCGCCTCCCCACAGCTGCTGCTCGGCCTCTTCCTTGTGCTACTGCTGCTTCTGCAGCTGT
Human CCGCCTCCCCGCAGCGGCTCCGCGGCCTCCT------GCTGCTCCTGCTGCTGCAGCTGC
             130        140        150               160        170
        200        210        220        230        240        250
Rat   CCGCGCCGTCCAGCGCCTCTGAGAATCCCAAGGTGAAGCAAAAAGCGCTGATCCGGCAGA
Human CCGCGCCGTCGAGCGCCTCTGAGATCCCCAAGGGGAAGCAAAAGGCGCAGCTCCGGCAGA
             180        190        200        210        220        230
        260        270        280        290        300        310
Rat   GGGAAGTGGTAGACCTGTATAATGGGATGTGCCTACAAGGACCAGCAGGAGTTCCTGGTC
Human GGGAGGTGGTGGACCTGTATAATGGAATGTGCTTACAAGGGCCAGCAGGAGTGCCTGGTC
             240        250        260        270        280        290
        320        330        340        350        360        370
Rat   GCGATGGGAGCCCTGGGGCCAATGGCATTCCTGGCACACCGGGAATCCCAGGTCGGGATG
Human GAGACGGGAGCCCTGGGGCCAATGGCATTCCGGGTACACCTGGGATCCCAGGTCGGGATG
             300        310        320        330        340        350
        380        390        400        410        420        430
Rat   GATTCAAAGGAGAGAAAGGGGAGTGCTTAAGGGAAAGCTTTGAGGAATCCTGGACCCCAA
Human GATTCAAAGGAGAAAAGGGGGAATGTCTGAGGGAAAGCTTTGAGGAGTCCTGGACACCCA
             360        370        380        390        400        410
        440        450        460        470        480        490
Rat   ACTACAAGCAGTGTTCATGGAGTTCACTTAATTATGGCATAGATCTTGGGAAAATTGCGG
Human ACTACAAGCAGTGTTCATGGAGTTCATTGAATTATGGCATAGATCTTGGGAAAATTGCGG
 420        430        440        450        460        470
        500        510        520        530        540        550
Rat   AATGTACATTCACAAAGATGCGATCCAACAGCGCTCTTCGAGTTCTGTTCAGTGGCTCGC
Human AGTGTACATTTACAAAGATGCGTTCAAATAGTGCTCTAAGAGTTTTGTTCAGTGGCTCAC
             480        490        500        510        520        530

560        570        580        590        600        610
Rat   TTCGGCTCAAATGCAGGAATGCTTGCTGTCAACGCTGGTATTTTACCTTTAATGGAGCTG
Human TTCGGCTAAAATGCAGAAATGCATGCTGTCAGCGTTGGTATTTCACATTCAATGGAGCTG
             540        550        560        570        580        590
        620        630        640        650        660        670
Rat   AATGTTCAGGACCTCTTCCCATTGAAGCTATCATCTATCTGGACCAAGGAAGCCCTGAGT
Human AATGTTCAGGACCTCTTCCCATTGAAGCTATAATTTATTTGGACCAAGGAAGCCCTGAAA
             600        610        620        630        640        650
        680        690        700        710        720        730
Rat   TAAATTCAACTATTAATATTCATCGTACTTCCTCCGTGGAAGGACTCTGTGAAGGGATTG
Human TGAATTCAACAATTAATATTCATCGCACTTCTTCTGTGGAAGGACTTTGTGAAGGAATTG
             660        670        680        690        700        710
        740        750        760        770        780        790
Rat   GTGCTGGACTGGTAGACGTGGCCATCTGGGTCGGCACCTGTTCAGATTACCCCAAAGGAG
```

FIG.4A

```
Human GTGCTGGATTAGTGGATGTTGCTATCTGGGTTGGCACTTGTTCAGATTACCCAAAAGGAG
         720       730       740       750       760       770
         800       810       820       830       840       850
Rat   ACGCTTCTACTGGGTGGAATTCTGTGTCCCGCATCATCATTGAAGAACTACCAAAATAAA
Human ATGCTTCTACTGGATGGAATTCAGTTTCTCGCATCATTATTGAAGAACTACCAAAATAAA
         780       790       800       810       820       830
         860       870       880       890       900       910
Rat   GCCCCTGAAGGTTTCATTCCCTGCCTCATTTACTTGTTAAATCAAGCCTCTGGATGGGTC
Human TGCTTTAAT--TTTCATTTGCTACCTCTTTTTTT------ATTATGCCTTGGAATGGTTC
         840       850       860          870       880
         920       930       940       950       960       970
Rat   ATTTAAATGACATTTCAGAAGTCACTTATGTGCTCAGCCAAATGAAAAAGCAAAGTTAAA
Human ACTTAAATGACATTTTA-AATAAGTTTATGTATACATCTGAATGAAAA-GCAAAGCTAAA
         890       900       910       920       930       940
         980       990      1000      1010      1020      1030
Rat   TACGTTTACAGACCAAAGTGTGATCTCACACT---TTAAGATCTAGCATTATCCATTTTA
Human TATGTTTACAGACCAAAGTGTGATTTCACACTGTTTTAAATCTAGCATTATTCATTTTG
         950       960       970       980       990      1000
                  1040      1050      1060      1070      1080
Rat   TTTCAACCAAAGATGGTTTCAGGATTTTATTTCTCATT--GATTACTTTTTG--------
Human CTTCAATCAAAAGTGGTTTCAATATTTTTTTAGTTGGTTAGAATACTTTCTTCATAGTCA
         1010      1020      1030      1040      1050      1060
                            1090      1100      1110      1120      1130
Rat   ---------AGCCTATATACCGGAATGCTGTTATAGTCTTTAATATTTCCTACT-GTTGA
Human CATTCTCTCAACCTATAATTTGGAATATTGTTGTGGTCTTTTGTTTTTTCTCTTAGTATA
         1070      1080      1090      1100      1110      1120
              1140      1150      1160      1170
1180
Rat   -CATTTTGAAACA--TATAAAAGTTATG--TCTTTGTAAGAGCTGTATA------GAATT
Human GCATTTTTAAAAAAATATAAAAGCTACCAATCTTTGTACAATTTGTAAATGTTAAGAATT
         1130      1140      1150      1160      1170      1180
                   1190      1200      1210
Rat   ATTTT---ATATGTTAAATAAA---TGCTTCAAACAA
Human TTTTTTATATCTGTTAAATAAAAATTATTTCCAACAA
         1190      1200      1210      1220
```

FIG.4A-1

```
Rat:     1  MHPQGRAASPQLLLGLFLVLLLLLQLSAPSSASENPKVKQKALIRQREVVDLYNGMCLQG   60
            M+PQG+AASPQ+L+GL+++LLLLLQL+APSSASE+PK+KQKA++RQREVVDLYNGMCLQG
Human:   1  MRPQGPAASPQRIRGL--LLLLLQLPAPSSASEIPKGKQKAQLRQREVVDLYNGMCLQG   58

Rat:    61  PAGVPGRDGSPGANGIPGTPGIPGRDGFKGEKGECLRESFEESWTPNYKQCSWSSLNYGI  120
            PAGVPGRDGSPGANGIPGTPGIPGRDGFKGEKGECLRESFEESWTPNYKQCSWSSLNYGI
Human:  59  PAGVPGRDGSPGANGIPGTPGIPGRDGFKGEKGECLRESFEESWTPNYKQCSWSSLNYGI  118

Rat:   121  DLGKIAECTFTKMRSNSALRVLFSGSLRLKCRNACCQRWYFTFNGAECSGPLPIEAIIYL  180
            DLGKIAECTFTKMRSNSALRVLFSGSLRLKCRNACCQRWYFTFNGAECSGPLPIEAIIYL
Human: 119  DLGKIAECTFTKMRSNSALRVLFSGSLRLKCRNACCQRWYFTFNGAECSGPLPIEAIIYL  178

Rat:   181  DQGSPELNSTINIHRTSSVEGLCEGIGAGLVDVAIWVGTCSDYPKGDASTGWNSVSRIII  240
            DQGSPE+NSTINIHRTSSVEGLCEGIGAGLVDVAIWVGTCSDYPKGDASTGWNSVSRIII
Human: 179  DQGSPEMNSTINIHRTSSVEGLCEGIGAGLVDVAIWVGTCSDYPKGDASTGWNSVSRIII  238

Rat:   241  EELPK  245
            EELPK
Human: 239  EELPK  243
```

FIG4B

MRPAAELGQTLSRAGLCRPLCLLLCASQLPHTMHPQGRAASPQLLLGLFLVLLLLQL
SAPSSASENPKVKQKALIRQREVVDLYNGMCLQGPAGVPGRDGSPGANGIPGTPGIPG
RDGFKGEKGECLRESFEESWTPNYKQCSWSSLNYGIDLGKIAECTFTKMRSNSALRVL
FSGSLRLKCRNACCQRWYFTFNGAECSGPLPIEAIIYLDQGSPELNSTINIHRTSSVE
GLCEGIGAGLVDVAIWVGTCSDYPKGDASTGWNSVSRIIIEELPK

FIG 4C

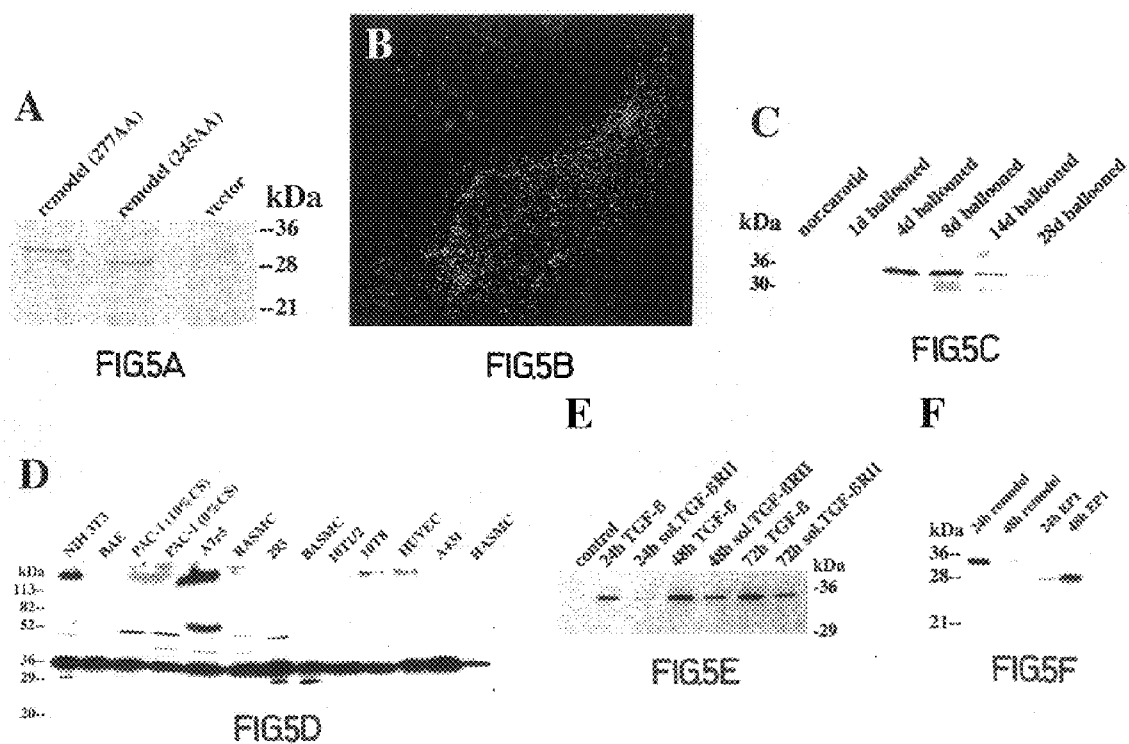

ATG GCCCCCAAGG CCGGCGCCGCC TCCCCACAGC TGCTGCTCGG CCTCTTCCTT GTGCTACTGC
TGCTTCTGCA GCTGTCCGCG CCGTCCAGCG CCTCTGAGAA TCCCAAGGTG AAGCAAAAAG
CGCTGATCCG GCAGAGGGAA GTGGTAGACC TGTATAATGG GATGTGCCTA CAAGGACCAG
CAGGAGTTCC TGGTCGCGAT GGGAGCCCTG GGGCCAATGG CATTCCTGGC ACACCGGGAA
TCCCAGGTCG GGATGGATTC AAAGGAGAGA AAGGGGAGTG CTTAAGGAA AGCTTTGAGG
AATCCTGGAC CCCAAACTAC AAGCAGTGTT CATGGAGTTC ACTTAATTAT GGCATAGATC
TTGGGAAAAT TGCGGAATGT ACATTCACAA AGATGCGATC CAACAGCGCT CTTCGAGTTC
TGTTCAGTGG CTCGCTTCGG CTCAAATGCA GGAATGCTTG CTGTCAACGC TGGTATTTTA
CCTTTAATGG AGCTGAATGT TCAGGACCTC TTCCCATTGA AGCTATCATC TATCTGGACC
AAGGAAGCCC TGAGTTAAAT TCAACTATTA ATATTCATCG TACTTCCTCC GTGGAAGGAC
TCTGTGAAGG GATTGGTGCT GGACTGGTAG ACGTGGCCAT CTGGGTCGGC ACCTGTTCAG
ATTACCCCAA AGGAGACGCT TCTACTGGGT GGAATTCTGT GTCCCGCATC ATCATTGAAG
AACTACCAAA A

FIG 7

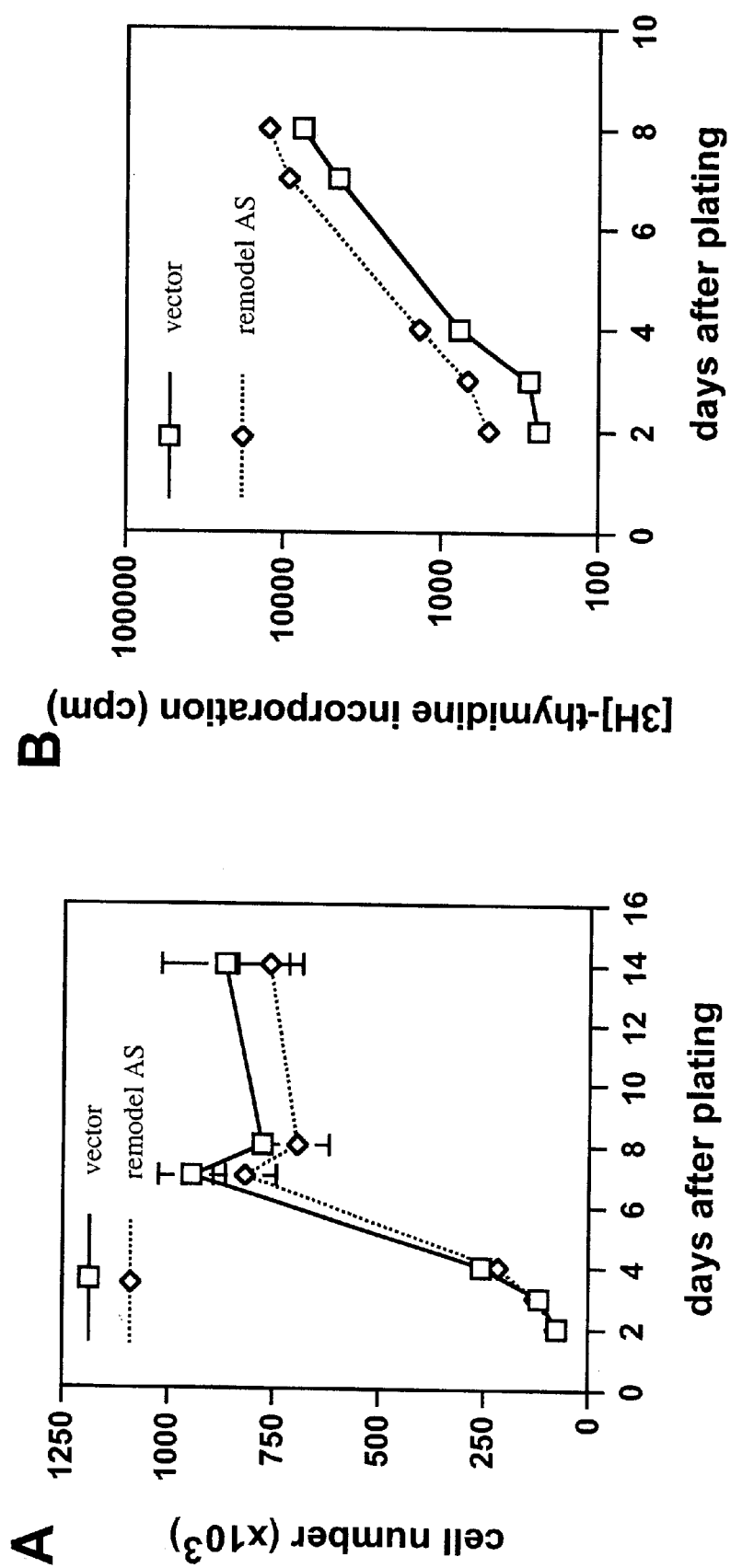

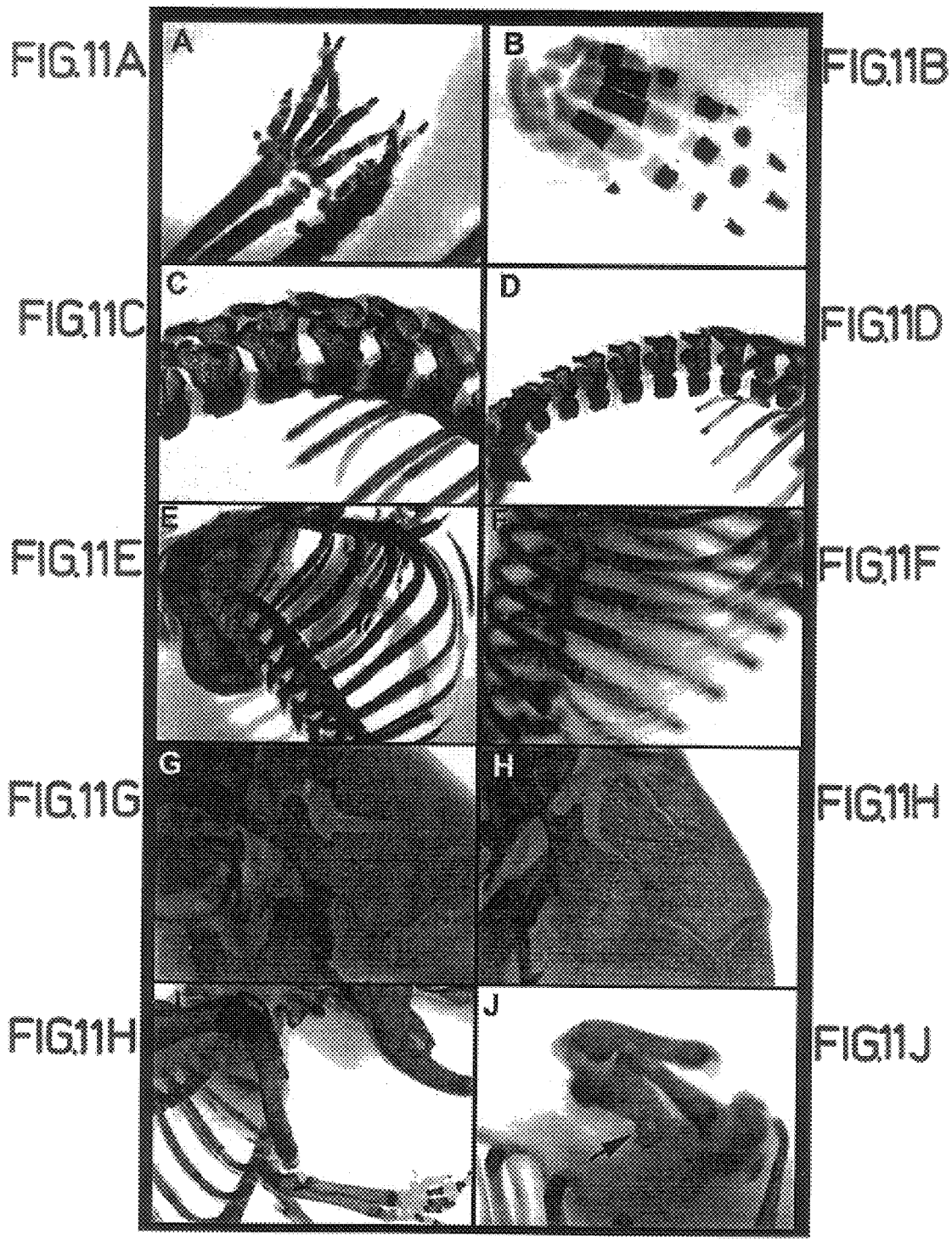

CCACCCAGAGUAGAAGCGGUCUCCCUUUGGGGUAAUCUGAACAGGUGCCGACCCAGAUGGCC
ACGUCUACAGGUCCAGCACCAAUCCCCUUCACAGAGUCCUUCACGGAGGAAGUACGAU
GAAUAUUAAAGUUGAAUUUAACUCAGGGCUUCCCUUGGUCCAGAUAGAUAGAUAGCUUC
AAUGGGAAGAGGUCCUGAACAUUCAGCUCCAUUAAAGGUAAAAUACCAGCGUUGACAG
CAAGCAUUCCCUGCAUUUGAGCCGAAGCGAGCCACUGAACAGAACUCGAAGAGCGCUGU
UGGAUCGCAUCUUUGUGAAUGUACAUUCCGCAAUUUCCCAAGAUCUAUGCCAUAAUU
AAGUGAACUCCAUGAACACACUGCUUGUAGUUUGGGGUCCAGAGAUUCCCUCAAAGCUU

FIG. 12

COMPOSITIONS, METHODS AND KITS RELATING TO REMODEL

BACKGROUND OF THE INVENTION

The present invention relates to identifying novel processes involved in mediating arterial remodeling.

Arterial stenosis with reduction in blood flow is a common problem in many vascular diseases. Several growth factors have been implicated in the mechanisms leading to vascular stenosis. For instance, fibroblast growth factor 2 (FGF-2) has been identified as an important factor in mediating proliferation of smooth muscle cells leading to intimal lesion formation. Furthermore, it has been demonstrated that arterial stenosis in response to angioplasty is largely due to negative remodeling as a result of adventitial fibrosis. As more fully set forth below, transforming growth factor beta (TGF-β) signaling has been demonstrated to play an important role in arterial stenosis in that, among other things, inhibition of TGF-β signaling using a soluble TGF-β receptor type II dramatically reduced lumen narrowing by decreasing negative remodeling and adventitial matrix deposition as well by decreasing neointima formation. These results indicate the crucial role of TGF-β signaling in arterial response to injury.

Vascular remodeling is a response of blood vessels to both physiological and pathological stimuli, leading to either vessel enlargement (positive remodeling) or shrinkage (negative remodeling). It has been demonstrated that neointimal proliferation or intimal mass following angioplasty shows little correlation with restenosis because of permanent changes in vascular geometry (Kakuta et al., 1994, Circulation 89:2809–2815; Nunes et al., 1995, Arterioscler. Thromb. Vasc. Biol. 15:156–165). Negative remodeling has been shown to account for most of the restenosis process (Mintz et al., 1993, Circulation 88:1–654), and is now generally considered the predominant cause of restenosis. A successful therapeutic approach to restenosis, therefore, would target negative vascular remodeling.

Several growth factors have been implicated in the mechanisms leading to vascular stenosis, such as fibroblast growth factor-2 (FGF-2) and transforming growth factor-β (TGF-β). Specifically, cellular responses involving TGF-β in the adventitia have gained increased attention for their potential involvement in adventitial remodeling (Wilcox et al., 1996, Int. J. Radiat. Oncol. Biol. Phys. 36:789–796; Wilcox and Scott, 1996, Int. J. Cardiol. 54S:S21–35; Shi et al., 1996, Circulation 93:340–348). There is evidence that proliferative events occurring in the adventitia contribute to vascular remodeling and restenosis in response to vascular injury (Wilcox et al., 1996, Int. J. Radiat. Oncol. Biol. Phys. 36:789–796; Wilcox et al., 1997, Ann. N.Y. Acad. Sci. 811:437–447; Scott et al., 1996, Circulation 93:2178–2187). There is now general agreement that TGF-β is a potential factor in the adventitial remodeling process (Shi et al., 1996, Arterioscler. Thromb. Vasc. Biol. 16:1298–1305).

Although it is known that the TGF-β family of cytokines can have a variety of effects on vascular cells, very little is known about the role of this family of cytokines in vascular remodeling. TGF-β affects many functions including proliferation of smooth muscle cells (SMC) (Halloran et al., 1995, Am. J. Surg. 170:193–197). It has been demonstrated that inhibition of SMC proliferation by TGF-β occurs via extension of the G2 phase of the cell cycle (Grainger et al., 1994, Biochem. J. 299:227–235). In contrast, it has also been shown that inhibition of SMC proliferation by TGF-β1 is due to arrest in the late G1 phase of the cell cycle (Reddy and Howe, 1993, J. Cell Physiol. 156:48–55). SMC derived from atherosclerotic lesions responded to TGF-β1 with an increase in proliferation, and lower levels of TGF-β receptor II (TGF-βRII) have been implicated in the lack of inhibition by TGF-β in these cells (McCaffrey et al., 1995, J. Clin. Invest. 96:2667–2675).

Further studies have established that TGF-β1 stimulates SMC proliferation in vitro. Low doses of TGF-β1 stimulated SMC proliferation via platelet-derived growth factor (PDGF)-amino acid (AA)-dependent and PDGF-AA-independent mechanisms, while higher doses of TGF-β1 were inhibitory (Battegay et al., 1990, Cell 63:515–524; Stouffer and Owens, 1994, J. Clin. Invest. 93:2048–2055). Bifunctional effects of TGF-β1 in migration assays with SMC were also demonstrated (Koyama et al., 1990, Biochem. Biophys. Res. Commun. 169:725–729; Mii et al., 1993, Surgery 114:464–470).

TGF-β1 also plays a role in intimal lesion formation as indicated by a 5–7 fold induction of TGF-β1 mRNA in the balloon-injured rat carotid artery, with elevated levels of TGF-β1 mRNA persisting for 2 weeks (Majesky et al., 1991, J. Clin. Invest. 88:904–910). During the 2 week period, elevated TGF-β1 mRNA levels correlated with increases in mRNA expression of fibronectin and alpha-2 (I) and alpha-1 (III) collagens. These studies also demonstrated that infusion of recombinant TGF-β1 caused an increase in intimal SMC proliferation in vivo (id.).

Among clinically significant findings regarding the role of TGF-β signaling in arterial response to injury, it has been demonstrated that TGF-β1 mRNA expression in restenotic lesions compared to primary atherosclerotic lesions is increased (Nikol et al., 1992, J. Clin. Invest. 90:1582–1592). In the rat balloon injury model, treatment with TGF-β1 antibodies caused a small but significant reduction in neointima formation (Wolf et al., 1994, J. Clin. Invest. 93:1172–1178). Overexpression of TGF-β1 in the rat carotid artery by adenoviral gene transfer led to transient neointima formation with cartilaginous metaplasia that almost completely resolved within 8 weeks (Shulick et al., 1998, Proc. Natl. Acad. Sci. USA 95:6983–6988). Without wishing to be bound by any particular theory, TGF-β1 may also effect vascular tone since the factor was found to suppress nitric oxide synthase expression (Perella et al., 1996, J. Biol. Chem. 271:13776–13780) while at the same time inducing the vasoconstrictor endothelin in SMC in vitro (Kurihara et al., 1989, Biochem. Biophys. Res. Commun. 159:1435–1440). Further, TGF-β1 has been implicated in anti-apoptotic effects in SMC (Herbert and Carmeliet, 1997, FEBS Lett. 413:401–404).

Studies examining the expression of TGF-β ligand and TGF-β receptor (TGF-βR) mRNAs using reverse transcriptase polymerase chain reaction (RT-PCR) analysis revealed that TGF-β1, TGF-β3, and TGF-βRII mRNA levels were increased in the media of the injured rat carotid artery (Ward et al., 1997, Arterioscler. Thromb. Vasc. Biol. 17:2461–2470) and expression of TGF-β2 and TGF-β3 were also reported in SMC of the lung vasculature (Khalil et al., 1996, Am. J. Respir. Cell Mol. Biol. 14:131–138; Pelton et al., 1991, Am. J. Respir. Cell Mol. Biol. 5:522–530). However, reduced levels of TGF-βRII were demonstrated in human atherosclerotic lesions (McCaffrey et al., 1995, J. Clin. Invest. 96:2667–2675). The three TGF-β ligands have overlapping functions and all of them induce expression of the alpha-1 (I), alpha-2 (I) and alpha-1 (III) chains of collagen (Bray et al., 1998, Hypertension 31:986–994).

The role of TGF-β isoforms in vascular repair processes was examined using a rat balloon catheter denudation model (Smith et al., 1999, Circ. Res. 84:1212–1222). Proliferating and quiescent SMC in denuded vessels expressed high levels of mRNA for TGF-β1, TGF-β2, and TGF-β3, and lower levels of TGF-βRII mRNA (Smith et al., 1999, Circ. Res. 84:1212–1222). The role of TGF-β signaling in the rat carotid artery balloon injury model was tested and it was shown that control vessels developed an extensive neointima and adventitial fibrosis with abundant collagen production. Vessels from animals injected with a recombinant soluble TGF-βRII (designated as "TGF-βR:Fc") revealed only little neointima formation and much less collagen deposition in the adventitia. The adventitia also contained significantly fewer cells, indicating that the proliferation of adventitial fibroblasts is mediated by TGF-β. Further, inhibition of TGF-β signaling with TGF-βR:Fc dramatically reduced lumen narrowing by decreasing negative remodeling and adventitial matrix deposition, as well as neointima formation.

TGF-β has been implicated in myofibroblastic transdifferentiation (Orlandi et al., 1994, Exp. Cell Res. 214:528–536; Desmouliere et al., 1993, J. Cell Biol. 122:103–111; Verbeek et al., 1994, Am. J. Pathol. 144:372–382), causing fibroblasts to transiently express smooth muscle α-actin (Darby et al., 1990, Lab. Invest. 63:21–29). The expression of smooth muscle α-actin in the carotid artery was examined using immunostaining at 4 days after balloon denudation when proliferation of adventitial fibroblasts is rapid. Immunoreactive smooth muscle α-actin was either completely absent or markedly reduced in the outer adventitia of vessels from rats treated with TGF-βR:Fc compared to controls. This result demonstrated that the induction of smooth muscle α-actin expression by adventitial fibroblasts is at least in part mediated by TGF-β.

Morphometric analysis of the carotid arteries demonstrated significant increases in lumen area in all rats treated with TGF-βR:Fc with an approximate 88% increase with a dose of 2 mg/kg given every other day for 2 weeks. Further, a dose of 0.5 mg/kg every other day for 2 weeks caused nearly a 60% increase in lumen area despite the fact that intimal lesion formation was not affected by this dose. These results indicate that loss of lumen area is in large part due to negative remodeling and measurements of the perimeter of the neointima (IEL) and media (EEL) demonstrated that all doses of TGF-βR:Fc used in this study significantly inhibited the reduction in IEL and EEL.

The effect of TGF-βR:Fc on remodeling is highly relevant to the clinical situation of restenosis after angioplasty (Mintz et al., 1993, Circulation 88:1–654; Mintz et al., 1994, Circulation 90:1–24). Immunostaining with anti-human IgG antibody demonstrated that the TGF-βR:Fc primarily localized to the adventitia and neointima indicating that these are the predominant sites of TGF-β activity because TGF-βR:Fc binds only active TGF-β. One prominent effect of soluble TGF-βRII was the effect on collagen synthesis, which was particularly striking in the adventitia of Masson's trichrome stained sections. It was further found that the effects of TGF-βR:Fc on collagen expression by Northern blot analysis of RNA isolated from carotid arteries 4 days after injury were markedly reduced for collagen Type I and Type III, but Type XV was unaffected. No differences in levels of osteopontin, tropoelastin, or fibronectin mRNA were detected.

Taken together, the aforementioned findings identify the TGF-β isoforms as major factors mediating adventitial fibrosis and negative remodeling following vascular injury. Thus, genes whose expression is affected by TGF-β are likely involved in such TGF-β associated processes, including arterial stenosis mediated by, inter alia, adventitial fibrosis and negative remodeling.

Arterial stenosis with reduction in blood flow is a common problem in many vascular diseases and it is an important causal factor in the morbidity and mortality associated with these diseases. Despite the fact that various growth factors, especially TGF-β, have been implicated in arterial stenosis, very few factors involved in arterial stenosis have been identified and characterized. Nevertheless, the identification of such factors is crucial in the development of diagnostics and therapeutics for treatment of vascular diseases associated or mediated by arterial stenosis. Thus, there is long-felt need for the identification and characterization of factors associated with arterial stenosis. The present invention meets this need.

BRIEF SUMMARY OF THE INVENTION

The invention includes an isolated nucleic acid encoding a mammalian REMODEL, or a fragment thereof.

In one aspect, the nucleic acid shares at least about 33% sequence identity with a nucleic acid encoding at least one of rat REMODEL (SEQ ID NO:1), and a human REMODEL (SEQ ID NO:3).

The invention also includes an isolated nucleic acid encoding a mammalian REMODEL, wherein the amino acid sequence of the REMODEL shares at least about 6% sequence identity with an amino acid sequence of at least one of SEQ ID NO:2, SEQ ID NO:4, and SEQ ID NO:5.

The invention includes an isolated polypeptide comprising a mammalian REMODEL. In one aspect, the mammalian REMODEL molecule shares at least about 6% sequence identity with an amino acid sequence of at least one of SEQ ID NO:2, SEQ ID NO:4, and SEQ ID NO:5.

The invention includes an isolated nucleic acid encoding a mammalian REMODEL, or a fragment thereof, wherein the nucleic acid further comprises a nucleic acid encoding a tag polypeptide covalently linked thereto.

In one aspect, the tag polypeptide is selected from the group consisting of a green fluorescent protein tag polypeptide, an influenza virus hemagglutinin tag polypeptide, a myc tag polypeptide, a glutathione-S-transferase tag polypeptide, a myc-pyruvate kinase tag polypeptide, a His6 tag polypeptide, a FLAG tag polypeptide, and a maltose binding protein tag polypeptide.

In another aspect, the nucleic acid further comprises a nucleic acid encoding a promoter/regulatory sequence operably linked thereto.

The invention includes a vector comprising an isolated nucleic acid encoding a mammalian REMODEL, or a fragment thereof. In another aspect, the invention includes a recombinant cell comprising the vector. In a further aspect, the vector further comprises a nucleic acid encoding a promoter/regulatory sequence operably linked thereto.

The invention includes a recombinant cell comprising an isolated nucleic acid encoding a mammalian REMODEL, or a fragment thereof.

The invention also includes an isolated nucleic acid complementary to an isolated nucleic acid encoding a mammalian REMODEL, or a fragment thereof, the complementary nucleic acid being in an antisense orientation. In one aspect, the complementary nucleic acid shares at least about 33% identity with a nucleic acid complementary with a nucleic acid having the sequence of at least one of a rat REMODEL molecule (SEQ ID NO:1), and a human REMODEL molecule (SEQ ID NO:3).

The invention includes a recombinant cell comprising the isolated nucleic acid complementary to an isolated nucleic acid encoding a mammalian REMODEL, or a fragment thereof, the complementary nucleic acid being in an antisense orientation.

The invention includes an antibody that specifically binds with a mammalian REMODEL molecule polypeptide, or a fragment thereof.

In one aspect, the antibody is selected from the group consisting of a polyclonal antibody, a monoclonal antibody, a humanized antibody, a chimeric antibody, and a synthetic antibody.

The invention includes a composition comprising the antibody that specifically binds with a mammalian REMODEL molecule polypeptide, or a fragment thereof, and a pharmaceutically-acceptable carrier.

The invention also includes a composition comprising the isolated nucleic acid complementary to the isolated nucleic acid encoding a mammalian REMODEL, or a fragment thereof, the complementary nucleic acid being in an antisense orientation, and a pharmaceutically-acceptable carrier.

The invention includes a composition comprising the isolated nucleic acid encoding a mammalian REMODEL, or a fragment thereof, and a pharmaceutically-acceptable carrier.

The invention includes a composition comprising the isolated polypeptide of comprising a mammalian REMODEL, and a pharmaceutically-acceptable carrier.

The invention includes a transgenic non-human mammal comprising the isolated nucleic acid encoding a mammalian REMODEL, or a fragment thereof.

The invention includes a method of treating a disease mediated by malexpression of a REMODEL molecule in a human. The method comprises administering to a human patient afflicted with a disease mediated by malexpression of a REMODEL molecule, a REMODEL molecule expression-inhibiting amount of the composition comprising the isolated nucleic acid complementary to the nucleic acid encoding a mammalian REMODEL, or a fragment thereof, and a pharmaceutically-acceptable carrier.

In one aspect, the disease is selected from the group consisting of impaired wound healing, fibrosis of an organ, ectopic ossification, and hypertrophic scar formation.

The invention includes a method of diagnosing arterial restenosis in a previously undiagnosed mammal. The method comprises obtaining a biological sample from the mammal, assessing the level of REMODEL in the biological sample, and comparing the level of REMODEL in the biological sample with the level of REMODEL in a biological sample obtained from a like mammal not afflicted with arterial restenosis, wherein a higher level of REMODEL in the biological sample from the mammal compared with the level of REMODEL in the biological sample from the like mammal is an indication that the mammal is afflicted with arterial restenosis, thereby diagnosing arterial restenosis in the previously undiagnosed mammal.

In one aspect, the biological sample is selected from the group consisting of a blood vessel sample, and a damaged tissue sample.

The invention includes a method of diagnosing negative remodeling in a previously undiagnosed mammal. The method comprises obtaining a biological sample from the mammal, assessing the level of REMODEL in the biological sample, and comparing the level of REMODEL in the biological sample with the level of REMODEL in a biological sample obtained from a like mammal not afflicted with negative remodeling, wherein a higher level of REMODEL in the biological sample from the mammal compared with the level of REMODEL in the biological sample from the like mammal is an indication that the mammal is afflicted with negative remodeling, thereby diagnosing negative remodeling in the previously undiagnosed mammal.

The invention includes a method of diagnosing fibrosis in a previously undiagnosed mammal. The method comprises obtaining a biological sample from the mammal, assessing the level of REMODEL in the biological sample, and comparing the level of REMODEL in the biological sample with the level of REMODEL in a biological sample obtained from a like mammal not afflicted with fibrosis, wherein a higher level of REMODEL in the biological sample from the mammal compared with the level of REMODEL in the biological sample from the like mammal is an indication that the mammal is afflicted with fibrosis, thereby diagnosing fibrosis in the previously undiagnosed mammal.

The invention includes a method of identifying a compound that affects expression of REMODEL in a cell. The method comprises contacting a cell with a test compound and comparing the level of REMODEL expression in the cell with the level of REMODEL expression in an otherwise identical cell not contacted with the test compound, wherein a higher or lower level of REMODEL expression in the cell contacted with the test compound compared with the level of REMODEL expression in the otherwise identical cell not contacted with the test compound is an indication that the test compound affects expression of REMODEL in a cell. In one aspect, the invention includes a compound identified by the method.

The invention includes a method of identifying a compound that reduces expression of REMODEL in a cell. The method comprises contacting a cell with a test compound and comparing the level of REMODEL expression in the cell with the level of REMODEL expression in an otherwise identical cell not contacted with the test compound, wherein a lower level of REMODEL expression in the cell contacted with the test compound compared with the level of REMODEL expression in the otherwise identical cell not contacted with the test compound is an indication that the test compound reduces expression of REMODEL in a cell. In one aspect, the invention includes a compound identified by the method.

The invention includes a method of identifying a compound that affects TGF-β signaling. The method comprises contacting a cell with a test compound and comparing the level of REMODEL expression in the cell with the level of REMODEL expression in an otherwise identical cell not contacted with the test compound, wherein a higher or lower level of REMODEL expression in the cell contacted with the test compound compared with the level of REMODEL expression in the otherwise identical cell not contacted with the test compound is an indication that the test compound affects TGF-β signaling in a cell.

The invention includes a kit for alleviating a disease mediated by malexpression of a REMODEL in a human. The kit comprises a REMODEL expression-inhibiting amount of a composition comprising the isolated nucleic acid complementary to the nucleic acid encoding a mammalian REMODEL, or a fragment thereof, and a pharmaceutically-acceptable carrier, the kit further comprising an applicator, and an instructional material for the use thereof. In one aspect, the disease is selected from the group consisting of negative remodeling, arterial restenosis, vessel injury, fibrosis.

The invention includes a kit for alleviating a disease mediated by malexpression of a REMODEL in a human. The kit comprises a REMODEL expression-inhibiting amount of the composition comprising encoding a mammalian REMODEL, or a fragment thereof, and a pharmaceutically-acceptable carrier, the kit further comprising an applicator, and an instructional material for the use thereof.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that invention is not limited to the precise arrangements and instrumentalities shown. In the drawings:

FIG. 1A-1 is an image of a Northern blot depicting total RNA isolated from various rat organs probed with labeled REMODEL (remodel) cDNA. A significant 1.2 kb band was present in cultured rat aortic smooth muscle cells, ballooned rat aorta, lung, and brain. Significantly lower REMODEL mRNA levels were detected in other tissues (i.e., liver, thymus, spleen, kidney, heart, muscle, uterus, and testis). A transcript of about 3.5 kb was detected in SMC upon longer exposure of the blot or loading of higher amount of RNA on the gel.

FIG. 1A-2 is an image depicting the gel used for Northern blot analysis in FIG. 1A-1. The gel was stained with ethidium bromide.

FIG. 1B-1 is an image of a Northern blot depicting expression of REMODEL mRNA in 8 day balloon-injured rat carotid arteries and normal carotid arteries. The data depicted herein demonstrate that REMODEL mRNA is expressed in the injured arteries only.

FIG. 1B-2 is an image depicting the gel used for Northern blot analysis in FIG. 1B-1. The gel was stained with ethidium bromide.

FIG. 1C-1 is an image of a Northern blot depicting levels of REMODEL mRNA in MC3T3 cells. The data disclosed herein demonstrate that the levels of REMODEL mRNA were increased by the addition of bone morphogenetic protein-4 (BMP-4), with peak expression after 8 hours.

FIG. 1C-2 is an image of a Northern blot depicting levels of REMODEL mRNA in MC3T3 cells. The data disclosed herein demonstrate that the levels of REMODEL mRNA were increased by the addition of TGF-β, with peak expression after 8 hours.

FIG. 1C-3 is an image depicting the gel used for Northern blot analysis in FIG. 1C-2. The gel was stained with ethidium bromide.

FIG. 2A is an image depicting an in situ hybridization analysis using [$^{35}$S]-UTP labeled antisense REMODEL riboprobe (sequence, SEQ ID NO:6). The arrowheads indicate the position of the internal elastic lamina. The image depicts normal carotid arteries and demonstrates no detectable REMODEL expression therein. The presence of silver grains, appearing as white specks under dark field illumination, indicates REMODEL expression.

FIG. 2B is an image depicting an in situ hybridization analysis using [$^{35}$S]-UTP labeled antisense REMODEL riboprobe (SEQ ID NO:6). The arrowheads indicate the position of the internal elastic lamina. The image demonstrates strong REMODEL expression limited to the adventitia of 8 day balloon injured arteries. The presence of silver grains, appearing as white specks under dark field illumination, indicates REMODEL expression.

FIG. 2C is an image depicting an in situ hybridization analysis using [$^{35}$S]-UTP labeled antisense REMODEL riboprobe (SEQ ID NO:6). The arrowheads indicate the position of the internal elastic lamina. The image demonstrates maintained but decreased REMODEL expression in the adventitia two weeks post-injury. The presence of silver grains, appearing as white specks under dark field illumination, indicates REMODEL expression.

FIG. 2D is an image depicting an in situ hybridization analysis using [$^{35}$S]-UTP labeled antisense REMODEL riboprobe (SEQ ID NO:6). The arrowheads indicate the position of the internal elastic lamina. The image demonstrates that at 4 weeks post-injury, expression levels of REMODEL expression were similar to levels detected in normal, control vessels. The presence of silver grains, appearing as white specks under dark field illumination, indicates REMODEL expression.

FIG. 2E is an image depicting an in situ hybridization analysis using [$^{35}$S]-UTP labeled antisense REMODEL riboprobe (SEQ ID NO:6). The image depicts a transverse section of an 11.5 days post coitus (dpc) mouse embryo wherein REMODEL expression is detectable in the developing mesoderm. The presence of silver grains, appearing as white specks under dark field illumination, indicates REMODEL expression.

FIG. 2F is an image depicting an in situ hybridization analysis using [$^{35}$S]-UTP labeled antisense REMODEL riboprobe (sequence, SEQ ID NO:6). The image depicts a 14.5 dpc mouse embryo expressing REMODEL in developing bone. The developing brain and bone are depicted. The image depicts that REMODEL expression becomes limited to the developing bone at later stages of embryo development. The presence of silver grains, appearing as white specks under dark field illumination, indicates REMODEL expression.

FIG. 2G is an image depicting an in situ hybridization analysis using [$^{35}$S]-UTP labeled antisense REMODEL riboprobe (SEQ ID NO:6). The image depicts REMODEL expression in the bones of the snout in a 14.5 dpc embryo. The presence of silver grains, appearing as white specks under dark field illumination, indicates REMODEL expression.

FIG. 2H is an image depicting an in situ hybridization analysis using [$^{35}$S]-UTP labeled antisense REMODEL riboprobe (SEQ ID NO:6). The image depicts strong detectable REMODEL expression in the bone of the developing skull of a 14.5 dpc mouse embryo. The presence of silver grains, appearing as white specks under dark field illumination, indicates REMODEL expression.

FIG. 2I is an image depicting an in situ hybridization analysis using [$^{35}$S]-UTP labeled antisense REMODEL riboprobe (SEQ ID NO:6). The image depicts osteoblasts adjacent to mineralized bone in a femur from a rat pup depicting expression of remodel mRNA. The arrowheads indicate the transition from the osteoblast layer to the mineralized bone layer at the upper right portion of the image. The image demonstrates strong REMODEL expression in osteoblasts along mineralized bone. The presence of silver grains, appearing as white specks under dark field illumination, indicates REMODEL expression.

FIG. 2J is an image depicting an in situ hybridization analysis using [$^{35}$S]-UTP labeled antisense REMODEL riboprobe (SEQ ID NO:6). The image depicts osteoblasts adjacent to mineralized bone in a femur from a rat pup depicting expression of REMODEL mRNA. The arrowheads indicate the transition from the osteoblast layer to the mineralized bone layer at the upper right portion of the image. The image demonstrates strong REMODEL expression in osteoblasts along mineralized bone.

The presence of silver grains, appearing as white specks under dark field illumination, indicates REMODEL expression.

FIG. 2K is an image depicting an in situ hybridization analysis using [$^{35}$S]-UTP labeled antisense REMODEL riboprobe (SEQ ID NO:6). The image depicts expression of REMODEL was undetectable in normal skin (the skin surface is located on the left side of the image). The presence of silver grains, appearing as white specks under dark field illumination, indicates REMODEL expression.

FIG. 2L is an image depicting an in situ hybridization analysis using [$^{35}$S]-UTP labeled antisense REMODEL riboprobe (SEQ ID NO:6). The image depicts extensive expression of REMODEL in a 7 day old skin incision along the wound edge in (myo)fibroblasts of the granulation tissue. The presence of silver grains, appearing as white specks under dark field illumination, indicates REMODEL expression.

Figure 3:
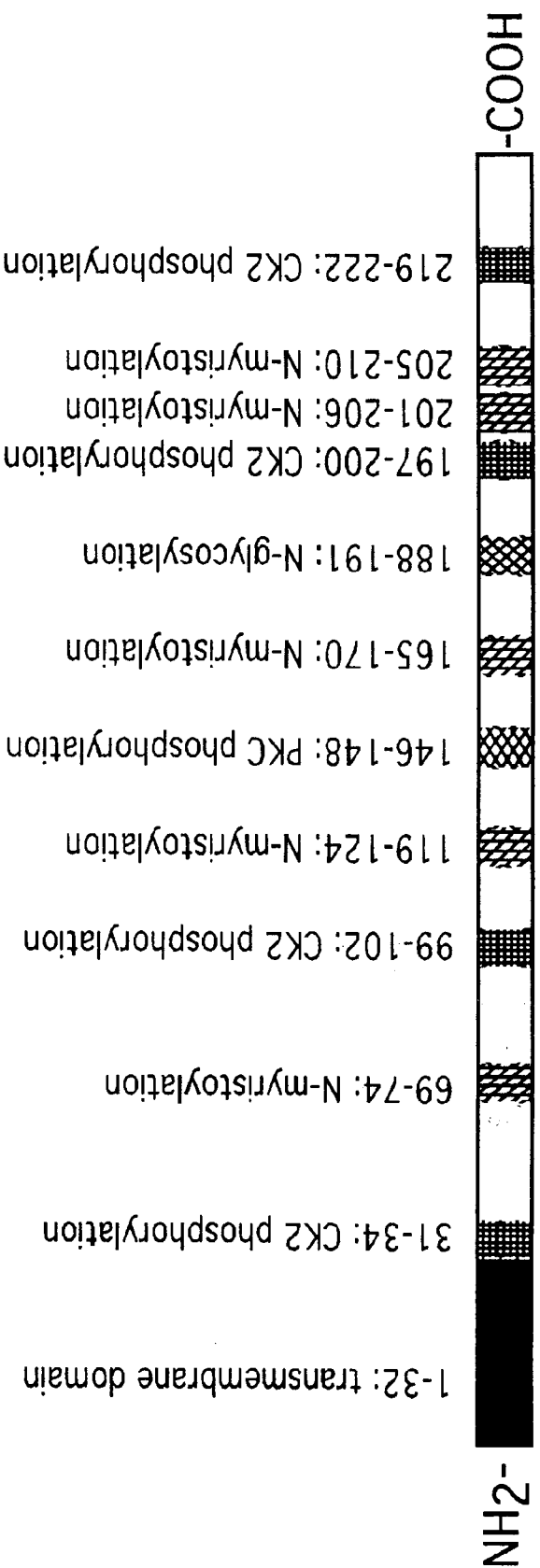

FIG. 3 is a diagram depicting the putative domains within the rat REMODEL-short (REMODELs) protein. The following domains are indicated: transmembrane domain/signal peptide (amino acid residues from about 1 to 32); a CK2 phosphorylation domain (amino acid residues from about 31 to 34); an N-myristoylation domain (amino acid residues from about 69 to 74); a CK2 phosphorylation domain (amino acid residues from about 99 to 102); an N-myristoylation domain (amino acid residues from about 119 to 124); a PKC phosphorylation domain (amino acid residues from about 146 to 148); an N-myristoylation domain (amino acid residues from about 165 to 170); an N-glycosylation domain (amino acid residues from about 188 to 191); a CK2 phosphorylation domain (amino acid residues from about 197 to 200); an N-myristoylation domain (amino acid residues from about 201 to 206); an N-myristoylation domain (amino acid residues from about 205 to 210); and a CK2 phosphorylation domain (amino acid residues from about 219 to 222).

FIG. 4A and FIG. 4A-1 is an image depicting the nucleic acid sequences for the rat (SEQ ID NO:1) and human (SEQ ID NO:3) REMODEL cDNA. Sequence homology between rat and human REMODEL cDNA is about 78% at the amino acid level. Translational start sites and stop codons are underlined. Gaps introduced into a sequence to maximize the alignment are indicated by a dash ("–").

FIG. 4B is an image depicting a comparison of the amino acid sequences of rat (SEQ ID NO:2) and human (SEQ ID NO:4) REMODEL. The data disclosed demonstrate that the two proteins share about 95% sequence identity. A consensus sequence is depicted between the two sequences. The "+" indicates a conserved amino acid substitution whereas "–" indicates either a gap or non-conserved amino acid substitution.

FIG. 4C is an image depicting the amino acid sequence of the long form of rat REMODEL (rREMODEL$_L$) (SEQ ID NO:5), encoded by the isolated nucleic acid SEQ ID NO:1 depicted in FIG. 4A, supra.

FIG. 5A is an image of an autoradiograph depicting expression of REMODEL protein using a rabbit reticulocyte lysate expression system. The image depicts the proteins produced by in vitro translation using the long and short forms of REMODEL cDNA. Using the long form of the rat REMODEL cDNA that contains an additional 5' in frame AUG start codon as a template, a predominant 34 kDa protein was expressed and lesser amounts of a 30 kDa protein was detected. Only the 30 kDa protein was produced when translation was performed using the short form of REMODEL cDNA.

FIG. 5B is an image depicting NIH3T3 cells transfected with a myc-tagged REMODEL (myc-REMODEL) expression construct. The myc-REMODEL fusion protein product was detected using anti-myc antibody using confocal microscopy. The image depicts that immunoreactivity was observed throughout the cytoplasm in a punctate/vesicular pattern. Nuclear counterstain was performed using propidium iodide.

FIG. 5C is an image of an immunoblot probed using rabbit antibody raised by immunizing using the carboxyterminal 15 amino acid residues of REMODEL (i.e., anti-REMODEL IgG). Cell lysates obtained from normal carotid arteries, and 1, 4, 7, 14 and 28 day balloon injured rat carotid arteries were resolved using SDS-PAGE and the proteins were transferred by Western blotting. The REMODEL antibody recognized a single band of approximately 34 kDa band only in the cell lysate prepared from the injured vessel but not in the normal vessel (nor. carotid).

FIG. 5D is an image of an immunoblot probed using rabbit anti-REMODEL IgG demonstrating expression of REMODEL protein in various cell lines from different species as follows: NIH3T3, bovine aortic epithelium (BAE), PAC-1 (a rat smooth muscle cell line), Ar75 (a rat smooth muscle cell line), RASMC (rat aortic smooth muscle cells), 293 cells, BASMC (bovine aortic SMC), 10T1/2 cells, human umbilical vein endothelial cells (HUVEC), A431 cells, and human aortic SMC (HASMC).

FIG. 5E is an image of an immunoblot probed using rabbit anti-REMODEL IgG depicting the effect of TGF-β1 or soluble TGF-β receptor type II (sol. TGF-βRII) on REMODEL expression. MC3T3 cells were treated with 1 ng/ml of TGF-β1 or 100 ng/ml TGF-βRII and the cells were harvested at the times indicated in the image. The data disclosed demonstrate that TGF-β1 stimulated REMODEL expression while TGF-βRII inhibited REMODEL expression. Approximately 30 micrograms of protein were loaded per lane.

FIG. 5F is an image depicting BAE cells transfected with a myc-tagged REMODEL (myc-REMODEL) expression construct. BAE were transiently transfected with a myc-tagged REMODEL expression construct. Expression of the transfected REMODEL fusion protein was detected using an anti-myc antibody and the data disclosed demonstrate that very little expression is detectable at 48 hours post-transfection. Without wishing to be bound by any particular theory, these data suggest loss of the transfected cells. BAE transfected with an unrelated protein (EP1) using the same vector as that used to prepare the myc-tagged REMODEL construct demonstrated higher levels of fusion protein expression 48 hours after transfection.

Figure 6A:
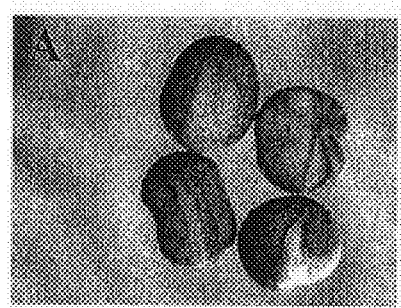

FIG. 6A is an image depicting the resulting phenotypes in Xenopus embryos after injection of REMODEL mRNA at the oocyte 2 cell stage. At the 17-cell stage, embryos injected with lacZ control RNA (shown on the left side of the image) exhibited normal development while embryos injected with REMODEL mRNA (shown on the right side of the image) exhibited inhibition of neurectodermal cell migration.

Figure 6B:

FIG. 6B is an image depicting normal control embryos at the 34-cell stage.

Figure 6C:

FIG. 6C is an image depicting REMODEL-injected 34-cell stage embryos. The REMODEL-injected embryos were smaller, distorted, and demonstrated abnormal development of the head compared with control embryos depicted in FIG. 6B.

Figure 6D:
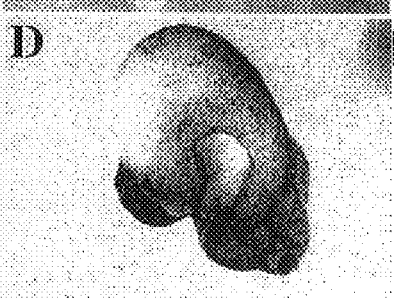

FIG. 6D is an image depicting a REMODEL-injected embryo exhibiting an unfused neurectoderm due to failure of the neural tissue cells to migrate.

Figure 6E:
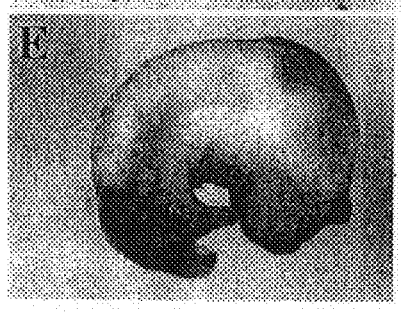

FIG. 6E is an image depicting a REMODEL-injected embryo exhibiting displaying the split tail phenotype common in REMODEL-injected embryos.

FIG. 7 is an image depicting the nucleic acid sequence (SEQ ID NO:9) of a myc-tagged REMODEL construct.

Figure 8A:
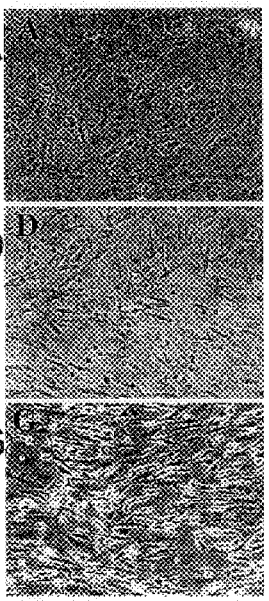

FIG. 8A is an image depicting the effect of REMODEL on cell adhesion and cell-cell contacts. MC3T3 cells were stably transfected with control vector and clonal populations were isolated. The data disclosed demonstrate that vector-transfected cells were of a cobblestone morphology. The image depicts a phase contrast image using 200×original magnification.

Figure 8B:
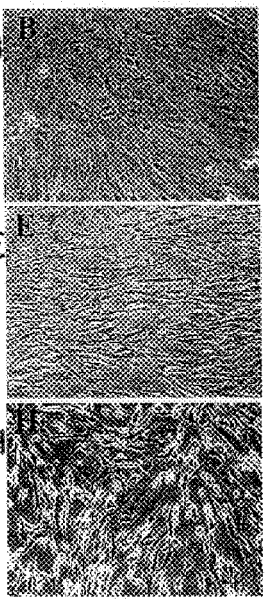

FIG. 8B is an image depicting the effect of REMODEL on cell adhesion and cell-cell contacts. MC3T3 cells were stably transfected with control vector and clonal populations were isolated. The data disclosed demonstrate that vector-transfected cells were of a cobblestone morphology. The image depicts a phase contrast image using 200×original magnification.

Figure 8C:
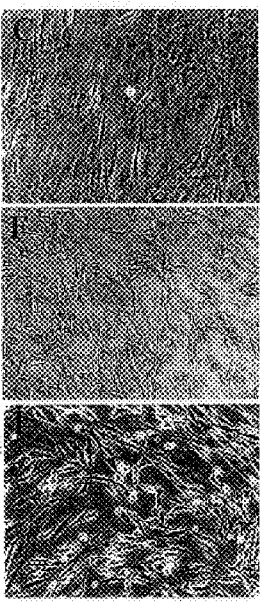

FIG. 8C is an image depicting the effect of REMODEL on cell adhesion and cell-cell contacts. MC3T3 cells were stably transfected with control vector and clonal populations were isolated. The data disclosed demonstrate that vector-transfected cells were of a cobblestone morphology. The image depicts a phase contrast image using 200×original magnification.

Figure 8D:
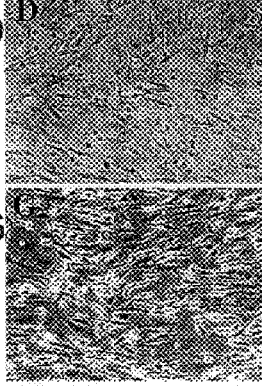

FIG. 8D is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

Figure 8E:
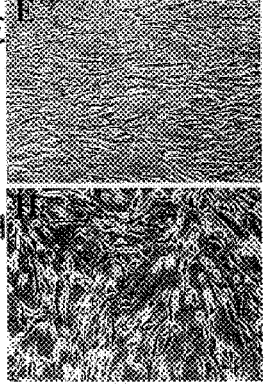

FIG. 8E is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

Figure 8F:
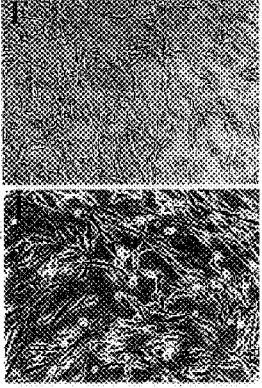

FIG. 8F is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

Figure 8G:
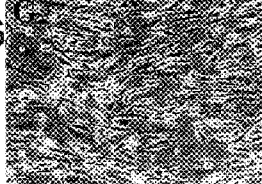

FIG. 8G is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

Figure 8H:

FIG. 8H is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

Figure 8I:

FIG. 8I is an image depicting the effect of REMODEL on cell adhesion and cell-cell contacts. MC3T3 cells were stably transfected with full length rat antisense REMODEL cDNA and clonal populations were isolated. The data disclosed herein demonstrate that antisense REMODEL transfected cells exhibit a distinctly altered phenotype with less adhesion to the substratum and reduced cell-cell contacts compared with control vector transfected cells. The image further depicts the increased number in dead cells and cell debris in the antisense transfected cells. The image depicts a phase contrast image using 200×original magnification.

FIG. 9A is a graph demonstrating that REMODEL expression is associated with and/or mediates increased cell turnover. MC3T3 cells were transfected with control vector or full-length rat antisense REMODEL cDNA and clonal populations were isolated. Cells were harvested at the time points indicated and cell numbers were determined. The data disclosed demonstrate that there was no increase in cell number in the antisense transfected cells compared with control cells.

FIG. 9B is a graph demonstrating that REMODEL expression is associated with and/or mediates increased cell turnover. MC3T3 cells were transfected with control vector or full-length rat antisense REMODEL cDNA and clonal populations were isolated. The cells were pulsed with [$^3$H]-thymidine for 4 hours before measuring incorporation of tritium in DNA. The cells were harvested in parallel at the time points after plating indicated and cell numbers were determined (FIG. 9A). The data disclosed demonstrate that there was increased cell turnover since there was increased [$^3$H]-thymidine incorporation but there was no increase in cell number in the antisense transfected cells compared with control cells (FIG. 9A).

Figure 10A:
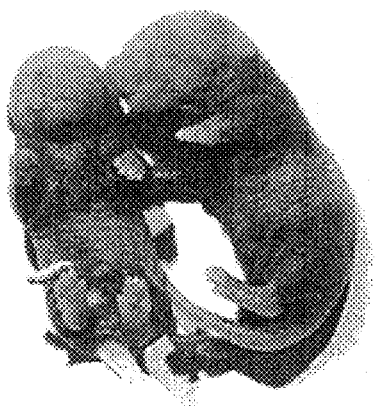

FIG. 10A is an image depicting one day old REMODEL transgenic mouse pups. Transgenic mice expressing REMODEL under the control of the cytomegalovirus (CMV) promoter/regulatory sequence were generated and a transgenic female was bred with a transgenic male giving rise to the pups depicted herein. All of the transgenic pups exhibited hemorrhaging in the hip and shoulder regions.

Figure 10B:
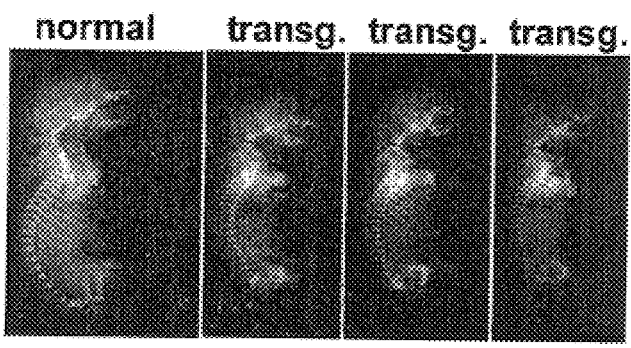

FIG. 10B is an image depicting one day old REMODEL transgenic mouse pups. Transgenic mice expressing REMODEL under the control of the cytomegalovirus (CMV) promoter/regulatory sequence were generated and a transgenic female was bred with a transgenic male giving rise to the pups depicted herein. X-ray examination of the skeleton identified that all transgenic mice were smaller with considerable shortening of the long bones. The image of three transgenic ("transg.") and one normal mouse are depicted.

Figure 10C:
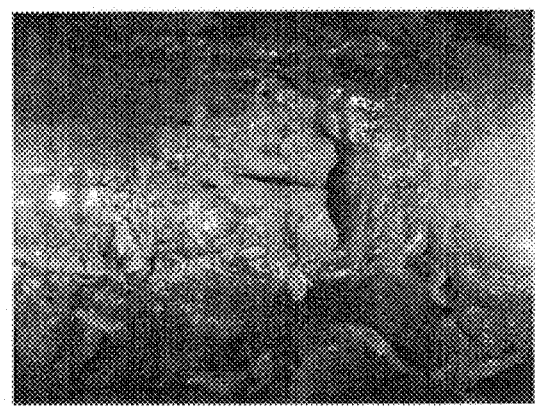

FIG. 10C is an image depicting one day old REMODEL transgenic mouse pups. Transgenic mice expressing REMODEL under the control of the cytomegalovirus (CMV) promoter/regulatory sequence were generated and a transgenic female was bred with a transgenic male giving rise to the pups depicted herein. Without wishing to be bound by any particular theory, similar to a spina bifida phenotype, the transgenic mice exhibited protrusion of neural tissue through the dorsal muscle layers in the thoracic area.

FIG. 11A is an image depicting skeletal preparation made from one day old non-transgenic pups otherwise identical to REMODEL transgenic pups. Mineralized bone appears pink in color (darker gray) and cartilage appears blue (lighter gray).

FIG. 11B is an image depicting skeletal preparation made from one day old REMODEL transgenic pups. Mineralized bone appears pink in color (darker gray) and cartilage appears blue (lighter gray). The image depicts reduced cartilage formation in all bones, including the distal phalanges of the feet when compared with normal, non-transgenic pups (FIG. 11A).

FIG. 11C is an image depicting skeletal preparation made from one day old non-transgenic pups otherwise identical to REMODEL transgenic pups. Mineralized bone appears pink in color (darker gray) and cartilage appears blue (lighter gray).

FIG. 11D is an image depicting skeletal preparation made from one day old REMODEL transgenic pups. Mineralized bone appears pink in color (darker gray) and cartilage appears blue (lighter gray). The image depicts that cartilage was absent from the intervertebral joints and the posterior portions of the vertebra when compared with normal, non-transgenic pups (FIG. 11C).

FIG. 11E is an image depicting skeletal preparation made from one day old non-transgenic pups otherwise identical to REMODEL transgenic pups. Mineralized bone appears pink in color (darker gray) and cartilage appears blue (lighter gray).

FIG. 11F is an image depicting skeletal preparation made from one day old REMODEL transgenic pups. Mineralized bone appears pink in color (darker gray) and cartilage appears blue (lighter gray). The image depicts that the anterior portions of the ribs, particularly the more caudal ones, exhibited a marked decrease in cartilage content when compared with normal, non-transgenic pups (FIG. 11E).

FIG. 11G is an image depicting skeletal preparation made from one day old non-transgenic pups otherwise identical to REMODEL transgenic pups. Mineralized bone appears pink in color (darker gray) and cartilage appears blue (lighter gray).

FIG. 11H is an image depicting skeletal preparation made from one day old REMODEL transgenic pups. Mineralized bone appears pink in color (darker gray) and cartilage appears blue (lighter gray). The image depicts that the transgenic pups exhibited decreased bone density, particularly in the flat bones of the skull which had a transparent appearance, when compared with normal, non-transgenic pups (FIG. 11G).

FIG. 11I is an image depicting skeletal preparation made from one day old non-transgenic pups otherwise identical to REMODEL transgenic pups. Mineralized bone appears pink in color (darker gray) and cartilage appears blue (lighter gray).

FIG. 11J is an image depicting skeletal preparation made from one day old REMODEL transgenic pups. Mineralized bone appears pink in color (darker gray) and cartilage appears blue (lighter gray). The image depicts that the transgenic pups exhibited decreased bone density compared with normal, non-transgenic pups (FIG. 11I). The data disclosed demonstrated that decreased bone density was associated with fragility leading to multiple fractures such as a fractured humerus (arrow), which explained the hemorrhaging observed in upper and lower limbs (FIG. 10A).

FIG. 12 is an image depicting the sequence of an isolated REMODEL antisense ribonucleic acid (SEQ ID NO:6) complementary to a portion of a nucleic acid encoding REMODEL.

DETAILED DESCRIPTION OF THE INVENTION

The invention relates to the discovery of a novel nucleic acid encoding a mammalian adventitia-inducible bone expressed molecule termed REMODEL, and the proteins encoded thereby. The data disclosed herein demonstrate that REMODEL plays a role in, inter alia, arterial restenosis mediated by or associated with adventitial fibrosis. Identification of REMODEL has important implications in the development of therapeutics and diagnostics for, among other things, adventitial fibrosis, arterial restenosis, negative remodeling, wound healing, and anti-cancer therapy.

More specifically, nucleic acids encoding REMODEL have been isolated in both rat and human. These sequences are provided herein, and have no significant homology to any known cDNA sequence.

The data disclosed herein demonstrate that expression of REMODEL is induced by vessel injury in mammals. That is, REMODEL was expressed in balloon-injured rat carotid arteries but not in normal, uninjured vessels. Furthermore, REMODEL was expressed selectively in the adventitia of the injured vessel, and was not expressed in the neointima or in the adventitia of normal vessels. Moreover, REMODEL expression was induced by TGF-β. This is important since proliferative events occurring in the adventitia contribute to vascular remodeling and restenosis in response to vascular injury and recent data demonstrate that TGF-β is a factor in this adventitial remodeling process. Thus, these data further indicate that REMODEL plays a role in cell proliferation and/or migration associated with vessel injury and restenosis due to negative remodeling.

The data disclosed herein also demonstrate that REMODEL plays an important role in development of bone during mammalian embryogenesis. REMODEL is normally expressed during mouse embryogenesis, but expression is localized to developing bone. However, in the adult mouse, REMODEL expression is virtually undetectable, expressing at very low levels in the adult brain and lung tissue.

Additionally, the data disclosed herein demonstrate that in studies using frog embryos, REMODEL also plays a role in cell proliferation and/or migration in that expression of REMODEL in frog embryos resulted in inhibition blastopore closure, failure of closure of the neural folds, formation of a split tail, and other developmental abnormalities. The REMODEL-injected embryos also presented with decreased size and distortion and abnormal development of the head.

Injection of REMODEL mRNA into frog embryos inhibited FGF-induced mesoderm formation. That is, animal caps from REMODEL-injected embryos incubated with FGF-1 resembled animal caps incubated in the absence of FGF-1. Indeed, the data disclosed herein demonstrate that the phenotype observed in frog embryos injected with REMODEL mRNA is similar to that of embryos injected from mRNA for dominant-negative FGF receptor constructs. These results, in addition to the induction of REMODEL by TGF-β, further indicate that REMODEL is an important factor in cell proliferation, migration, or both.

Additionally, over-expression of REMODEL in transgenic mice gave rise to spina bifida-like spinal defects. The transgenic mouse pups exhibited altered bone density and bone growth further indicating that REMODEL plays an important role in embryogenesis, including, but not limited to, a role in bone growth and dorsal closure.

The data disclosed herein also demonstrate that REMODEL is localized in the cell membrane via 5 potential N-myristoylation sites. Without wishing to be bound by any particular theory, these myristoylation sites may serve to anchor REMODEL protein in the cell membrane. This would indicate that REMODEL is not a secreted protein, but rather, it is associated with the cell in mediating its effect(s).

In sum, the data disclosed herein demonstrate that REMODEL plays a role in cell proliferation and/or migration and is involved in cellular signaling. Furthermore, the data demonstrate that REMODEL likely plays a role in adventitial fibrosis, negative remodeling and arterial restenosis, mediated by, among other things, smooth muscle cell proliferation. Therefore, the instant invention provides an in vitro model for the study of the function and role(s) of REMODEL in arterial remodeling, adventitial fibrosis, and restenosis in vessels, as well as potential therapeutics and diagnostics for treatment of diseases, disorders or conditions associated with adventitial fibrosis, arterial restenosis, bone density and bone growth.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name     | Three-Letter Code | One-Letter Code |
|---------------|-------------------|-----------------|
| Aspartic Acid | Asp               | D               |
| Glutamic Acid | Glu               | E               |
| Lysine        | Lys               | K               |
| Arginine      | Arg               | R               |
| Histidine     | His               | H               |
| Tyrosine      | Tyr               | Y               |
| Cysteine      | Cys               | C               |
| Asparagine    | Asn               | N               |
| Glutamine     | Gln               | Q               |
| Serine        | Ser               | S               |
| Threonine     | Thr               | T               |
| Glycine       | Gly               | G               |
| Alanine       | Ala               | A               |
| Valine        | Val               | V               |
| Leucine       | Leu               | L               |
| Isoleucine    | Ile               | I               |
| Methionine    | Met               | M               |
| Proline       | Pro               | P               |
| Phenylalanine | Phe               | F               |
| Tryptophan    | Trp               | W               |

By the term "adventitial fibrosis," as used herein, is meant the extensive fibrous (connective) tissue formation in the outer layer (i.e., adventitia) of a blood vessel. Adventitial fibrosis is associated with abundant deposition of extracellular matrix and proliferation of myofibroblasts and fibroblasts.

As used herein, to "alleviate" a disease, disorder or condition means reducing the severity of one or more symptoms of the disease, disorder or condition. This can include, but is not limited to, reducing the level of REMODEL expressed in a cell or tissue (e.g., SMC, lung tissue, an artery), reducing the level of cell proliferation and or migration, affecting wound healing, affecting granulation tissue formation, affecting bone growth and/or fracture healing, reducing negative remodeling, arterial restenosis and/or adventitial fibrosis, reducing or increasing the level of REMODEL in a patient, compared with the level of REMODEL in the patient prior to or in the absence of the method of treatment, and the like.

" Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, a bronchoscope, a nebulizer, and the like, for administering the REMODEL nucleic acid, protein, and/or composition of the invention to a mammal.

"Arterial restenosis," as that term is used herein, means the re-narrowing of an artery in response to a vascular intervention aimed at dilating a stenosed (i.e., narrowed) artery.

"Biological sample," as that term is used herein, means a sample obtained from an animal that can be used to assess the level of expression of a REMODEL, the level of REMODEL protein present, or both. Such a sample includes, but is not limited to, a blood vessel (e.g., carotid artery, aorta, and the like) sample, a lung tissue sample, a SMC sample, and a sample from any tissue undergoing wound healing.

By "candidate anti-REMODEL drug," as the term is used herein, is meant a compound that when contacted with a cell, reduces the level of expression of a nucleic acid encoding a REMODEL protein in the cell compared with the level of REMODEL expression in that cell prior to contacting the cell with the compound or which reduces the level of expression in the cell compared with the level of REMODEL expression in an otherwise identical cell which is not contacted with the compound.

By "complementary to a portion or all of the nucleic acid encoding REMODEL" is meant a sequence of nucleic acid which does not encode a REMODEL protein. Rather, the sequence which is being expressed in the cells is identical to the non-coding strand of the nucleic acid encoding a REMODEL protein and thus, does not encode REMODEL protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, preferably, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 650 nucleotides, yet even more preferably, at least about 650 to about 800, more preferably, from about 800 to about 1000 nucleotides, preferably, at least about 1000 to about 1100 nucleotides, even more preferably, at least about 1100 nucleotides to about 1200 nucleotides, yet even more preferably, at least about 1200 to about 1210, even more preferably, at least about 1210 nucleotides to about 1220 nucleotides, yet even more preferably, at least about 1220 to about 1225, and most preferably, the nucleic acid fragment will be greater than about 1230 nucleotides in length.

However, the present invention does not encompass the following isolated nucleic acids: AA335862 (sharing about 87% identity over about 373 nucleotides with REMODEL cDNA); C01758 (sharing about 87% identity over about 356 nucleotides with REMODEL cDNA); AA335551 (sharing about 87% identity over about 334 nucleotides with REMODEL cDNA); AA406425 (sharing about 88% identity over about 312 nucleotides with REMODEL cDNA); R46857; AA584310; D79314; AI085616; D62262; AA482398; AA482544; AI359844; AI352209; AI239604; AI218433; AI081084; AI074870; AI074769; AA974239; AA969841; AA857920; AA723450; AA410434; AA738416; AI370649; AA507081.

As applied to a protein, a "fragment" of REMODEL is about 20 amino acids in length. More preferably, the fragment of a REMODEL is about 30 amino acids, even more preferably, at least about 40, yet more preferably, at least about 60, even more preferably, at least about 80, yet more preferably, at least about 100, even more preferably, about 100, and more preferably, at least about 150, more preferably, at least about 200, yet more preferably, at least about 240, even more preferably, at least about 243, yet more preferably, at least about 250, even more preferably, about 270, and more preferably, at least about 277 amino acids in length amino acids in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, *Molecular Cloning: A Laboratory Manual*, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example, at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the mouse proteins described herein are within the scope of the invention. Nucleic acid molecules corresponding to natural allelic variants and homologs of a cDNA of the invention can be isolated based on their identity to mouse nucleic acid molecules using the mouse cDNAs, or a portion thereof, as a hybridization probe according to standard hybridization techniques under stringent hybridization conditions. For example, a homolog of a nucleic acid encoding a rat REMODEL protein of the invention can be isolated based on its hybridization with a nucleic acid molecule encoding all or part of rat and/or human REMODEL under high stringency conditions.

As used herein, an "instructional material" includes a publication, a recording, a diagram, or any other medium of expression which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a g22hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By the term "malexpression of REMODEL," as used herein, is meant that the level of expression of a REMODEL molecule (e.g., rat $REMODEL_S$, rat $REMODEL_L$, human REMODEL) in a cell is detectably higher or lower than the level of expression of REMODEL in an otherwise identical cell where the otherwise identical cell is obtained from normal tissue that does not exhibit any detectable disease, disorder or condition associated with or mediated by expression of REMODEL, such as, but not limited to, adventitial remodeling, adventitial fibrosis, arterial restenosis, negative remodeling, bone growth, bone fracture healing, wound healing in any tissue, and the like.

As used herein, the term "negative remodeling" (also known as inward remodeling) means a physiologic or pathologic response of a blood vessel to a stimulus resulting in a reduction of vessel diameter and lumen diameter. Such a stimulus could be provided by, for example, but not limited to, a change in blood flow or an angioplasty procedure.

"Neointima formation," as that term is used herein, means the thickening and enlargement of the tunica intima of a blood vessel due to accumulation of cells and extracellular matrix in this layer of the vessel.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

As used herein, the term "REMODEL" means any adventitia-induced and bone expressed molecule having significant sequence identity with REMODEL disclosed herein. More specifically, the putative REMODEL will share at least about 33% sequence identity with at least one of a nucleic acid having the sequence SEQ ID NO:1 and a nucleic acid having the sequence SEQ ID NO:3. More preferably, the nucleic acid encoding REMODEL has at least about 35% identity, even more preferably, at least about 40% identity, yet more preferably, at least about 45% identity, even more preferably, at least about 50% identity, more preferably, at least about 55% identity, even more preferably, at least about 60% identity, yet more preferably, at least about 65% identity, more preferably, at least about 70% identity, yet more preferably, at least about 75% identity, even more preferably, at least about 80% identity, more preferably, at least about 85% identity, yet more preferably, about 90% identity, even more preferably, at least about 95% identity, and most preferably, at least about 99% sequence identity with at least one of SEQ ID NO:1 and SEQ ID NO:3 disclosed herein. Even more preferably, the nucleic acid is at least one of SEQ ID NO:1 and SEQ ID NO:3. Further, the biological activity of a REMODEL preferably includes inhibition of expression of the nucleic acid encoding the REMODEL protein by a soluble TGF-β receptor type II (TGF-βRII), which blocks TGF-β signaling. Further, preferably, the biological activity of a REMODEL molecule includes induction of expression of the nucleic acid by TGF, induction of expression of the nucleic acid encoding a REMODEL in a blood vessel following vessel injury, induction of expression of the nucleic acid encoding the protein in fibroblasts during wound healing, expression in osteoblasts during bone formation, causing cell death in endothelial cells when it is overexpressed, involvement in cell-cell and cell-matrix interaction, and affecting cell viability such as by, for example, affecting the life span of a cell.

Further, the data disclosed elsewhere herein demonstrate that REMODEL plays an important role in bone growth. In one embodiment, transgenic mice over-expressing REMODEL, similar to data obtained using frog embryos which exhibited failure of dorsal closure, exhibited spina bifida-like effects. Therefore, the term "REMODEL" encompasses a nucleic acid that, when over-expressed in a mammalian embryo, mediates or is associated with altered bone growth, bone density, and/or spina bifida-like phenotype.

Unless otherwise indicated, "REMODEL" encompasses all known REMODELs (e.g., rat REMODEL$_S$, rat REMODEL$_L$, and human REMODEL), and REMODELs to be discovered, including but not limited to, mouse REMODEL, having the characteristics and/or physical features of the REMODEL disclosed herein.

However, the present invention does not include the isolated nucleic acids having the sequences designated by the following GenBank Accession Numbers: AA335862 (sharing about 87% identity with REMODEL over about 373 nucleotides); C01758 (sharing about 87% identity with REMODEL over about 356 nucleotides); AA335551 (sharing about 87% identity with REMODEL over about 334 nucleotides); and AA406425 (sharing about 88% identity with REMODEL over about 312 nucleotides); R46857; AA584310; D79314; AI085616; D62262; AA482398; AA482544; AI359844; AI352209; AI239604; AI218433; AI081084; AI074870; AI074769; AA974239; AA969841; AA857920; AA723450; AA410434; AA738416; AI370649; AA507081.

"REMODEL-inhibiting amount," as used herein, means any amount of a substance or molecule that detectably decreases the level of REMODEL expression, amount, and/or activity compared with the level of REMODEL expression, amount, and/or activity in the absence of the substance or molecule. Thus, any amount that mediates a detectable decrease in: the amount of REMODEL present, the level of REMODEL mRNA expression, and/or the ability of REMODEL to form necessary ligand/receptor interactions, is encompassed in the present invention. The assays by which these conditions are examined are well-known in the art and several are exemplified herein.

By the term "REMODEL-like activity," as used herein, refers to the ability of a molecule or compound to be induced by TGF-β, selectively induced in adventitia of injured vessels, to cause phenotypic abnormalities in amphibian embryos such as those disclosed herein (e.g., split tail, abnormal head development, lack of mesoderm development upon FGF-induction, failure of dorsal closure, and the like), to exhibit increased expression only in injured vessel adventitia but not in uninjured vessels nor in the neointima of injured or uninjured vessels, the ability to induce adventitial cell proliferation, to be inhibited by a soluble TGF-β receptor II (which blocks TGF-β signaling), the ability to be induced in fibroblasts during wound healing, the ability to be expressed by osteoblasts during bone formation, the ability to be expressed in osteoblasts adjacent to mineralized bone, the ability to be strongly expressed along full thickness skin incisions undergoing wound healing and remodeling, the ability to mediate cell death in endothelial cells when overexpressed, the ability to inhibit cell adhesion and cell-cell interaction when an antisense nucleic complementary to the nucleic acid encoding the molecule is expressed in a cell, and the ability to mediate excessive or insufficient wound healing responses, scarring, keloids, bone formation, bone density, lack of dorsal closure, spina bifida-like effects, fracture healing, and the like.

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgenic mammal" means a mammal, the germ cells of which comprise an exogenous nucleic acid.

As used herein, to "treat" means reducing the frequency with which symptoms of arterial restenosis, adventitial fibrosis, excessive or insufficient wound healing responses, scarring, keloids, bone formation, fracture healing, and the like, are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the REMODEL protein or nucleic acid encoding a mammalian REMODEL, to the patient, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/178310, published Aug. 18, 1994; International Patent Application No. WO94/23744, published Oct. 27, 1994). Examples of non-viral vectors include, but are not limited to, liposomes, polyamine derivatives of DNA, and the like.

A "knock-out targeting vector," as the term is used herein, means a vector comprising two nucleic acid sequences each of which is complementary to a nucleic acid regions flanking a target sequence of interest which is to be deleted and/or replaced by another nucleic acid sequence. The two nucleic acid sequences therefore flank the target sequence which is to be removed by the process of homologous recombination Description I. Isolated Nucleic Acids A. Sense Nucleic Acids The present invention includes an isolated nucleic acid encoding a mammalian adventitia-inducible and bone expressed molecule, REMODEL, or a fragment thereof, wherein the nucleic acid shares at least about 33% identity with at least one nucleic acid having the sequence of (SEQ ID NO:1) and (SEQ ID NO:3). Preferably, the nucleic acid is at least about 35% homologous, more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to at least one of SEQ ID NO:1 and SEQ ID NO:3 disclosed herein. Even more preferably, the nucleic acid is at least one of SEQ ID NO:1 and SEQ ID NO:3.

The present invention includes an isolated nucleic acid encoding rat REMODEL, or a fragment thereof, wherein the nucleic acid shares at least about 33% homology with a nucleic acid having the sequence SEQ ID NO:1. Preferably, the nucleic acid is at least about 35% homologous, more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to the rat REMODEL disclosed herein (SEQ ID NO:1). Even more preferably, the nucleic acid is SEQ ID NO:1.

The present invention includes an isolated nucleic acid encoding human REMODEL, or a fragment thereof, wherein the nucleic acid shares at least about 33% homology with human REMODEL (SEQ ID NO:3). Preferably, the nucleic acid is at least about 35% homologous, more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to the human REMODEL disclosed herein (SEQ ID NO:3). Even more preferably, the nucleic acid is SEQ ID NO:3.

In another aspect, the present invention includes an isolated nucleic acid encoding a mammalian REMODEL, or a fragment thereof, wherein the protein encoded by the nucleic acid shares greater than about 6% homology with the amino acid sequence of at least one of SEQ ID NO:2 (rat REMODEL$_S$), SEQ ID NO:4 (human REMODEL), and SEQ ID NO:5 (rat REMODEL$_L$). That is, searching GenBank databases disclosed that REMODEL shares about 62% sequence identity with a portion of the sequence GenBank Acc. No. P27393, collagen alpha-2 (IV) chain precursor, over a stretch of about 35 amino acids. Full-length REMODEL protein comprises about 243 amino acids such that full-length REMODEL shares about 5.7% overall sequence identity with collagen alpha-2 (IV) chain precursor (i.e., GenBank Acc. No. P27393).

Preferably, the protein encoded by the isolated nucleic acid encoding REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to at least one of SEQ ID NO:2, SEQ ID NO:4, and SEQ ID NO:5. Even more preferably, the REMODEL protein encoded by the nucleic acid is at least one of SEQ ID NO:2, SEQ ID NO:4, and SEQ ID NO:5.

In another aspect, the present invention includes an isolated nucleic acid encoding rat REMODEL, or a fragment thereof, wherein the protein encoded by the nucleic acid shares at least about 6% homology with the amino acid sequence of SEQ ID NO:2. Preferably, the protein encoded by the isolated nucleic acid encoding REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to rat REMODEL disclosed herein (SEQ ID NO:2). Even more preferably, the rat REMODEL protein encoded by the nucleic acid is SEQ ID NO:2.

In another aspect, the present invention includes an isolated nucleic acid encoding human REMODEL, or a fragment thereof, wherein the protein encoded by the nucleic acid shares at least about 6% homology with the amino acid sequence of SEQ ID NO:4. Preferably, the protein encoded by the isolated nucleic acid encoding REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to the human REMODEL disclosed herein (SEQ ID NO:4). Even more preferably, the human REMODEL protein encoded by the nucleic acid is SEQ ID NO:4.

One skilled in the art would understand, based upon the disclosure provided herein, that a nucleic acid encoding a rat REMODEL (SEQ ID NO:1) can be alternatively translated to produce an alternate rat REMODEL protein comprising 245 amino acids (rat $REMODEL_S$; SEQ ID NO:2) and a protein comprising an additional 32 amino acid residues at the N-terminus (i.e., the 277 amino acid long form of REMODEL designated $REMODEL_L$ [SEQ ID NO:5]) since the nucleic acid encoding rat REMODEL (SEQ ID NO:1) comprises two putative transcriptional start sites at positions 19 and 116 (FIG. 4A) that are compatible with the Kozak rule.

Therefore, in another aspect, the present invention includes an isolated nucleic acid encoding rat REMODEL, or a fragment thereof, wherein the protein encoded by the nucleic acid shares at least about 6% homology with the amino acid sequence of SEQ ID NO:5 (i.e., 277 amino acid rat $REMODEL_L$). Preferably, the protein encoded by the isolated nucleic acid encoding REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to the rat $REMODEL_L$ disclosed herein (SEQ ID NO:5). Even more preferably, the rat $REMODEL_L$ protein encoded by the nucleic acid is SEQ ID NO:5.

One skilled in the art would appreciate, based upon the disclosure provided herein, that a mouse REMODEL homolog likely exists and can be readily identified and isolated using the methods described herein using the sequence data disclosed herein regarding the highly-conserved rat and mouse homologs. Thus, the present invention encompasses additional REMODELs that can be readily identified based upon the disclosure provided herein, including, but not limited to, mouse REMODEL.

The isolated nucleic acid of the invention should be construed to include an RNA or a DNA sequence encoding a REMODEL protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding REMODEL proteins can such as those present in other species of mammals (e.g., ape, gibbon, bovine, ovine, equine, porcine, canine, feline, and the like) be obtained by following the procedures described herein in the experimental details section for the isolation of the rat, and human REMODEL nucleic acids encoding REMODEL polypeptides as disclosed herein (e.g., screening of genomic or cDNA libraries), and procedures that are well-known in the art (e.g., reverse transcription PCR using mRNA samples) or to be developed.

Further, any number of procedures may be used for the generation of mutant, derivative or variant forms of REMODEL using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding a mammalian REMODEL wherein a nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one of rat REMODEL and human REMODEL. Such tag polypeptides are well known in the art and include, for instance, green fluorescent protein (GFP), an influenza virus hemagglutinin tag polypeptide, myc, myc-pyruvate kinase (myc-PK), $His_6$, maltose biding protein (MBP), a FLAG tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize REMODEL within a cell, a tissue (e.g., a blood vessel, bone, and the like), and/or a whole organism (e.g., an amphibian and/or a mammalian embryo, and the like), detect REMODEL if secreted from a cell, and to study the role(s) of REMODEL in a cell. Further, addition of a tag polypeptide facilitates isolation and purification of the "tagged" protein such that the proteins of the invention can be produced and purified readily.

B. Antisense Nucleic Acids

In certain situations, it may be desirable to inhibit expression of REMODEL and the invention therefore includes compositions useful for inhibition of REMODEL expression. Thus, the invention features an isolated nucleic acid complementary to a portion or all of a nucleic acid encoding a mammalian REMODEL, which nucleic acid is in an antisense orientation with respect to transcription.

Preferably, the antisense nucleic acid is complementary with a nucleic acid having at least about 33% homology with at least one of SEQ ID NO:1 and SEQ ID NO:3, or a fragment thereof. Preferably, the nucleic acid is at least about 35% homologous, more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to a nucleic acid complementary to a portion or all of a nucleic acid encoding a mammalian REMODEL having the sequence of at least one of SEQ ID NO:1 and SEQ ID NO:3, or a fragment thereof, which is in an antisense orientation with respect to transcription. Most preferably, the nucleic acid is complementary to a portion or all of a nucleic acid that is at least one of SEQ ID NO:1 and SEQ ID NO:3, or a fragment thereof. Such antisense nucleic acid serves to inhibit the expression, function, or both, of an adventitia-inducible and bone expressed (REMODEL) molecule.

In one aspect, the invention includes an isolated nucleic acid complementary to a portion or all of a nucleic acid encoding a mammalian REMODEL molecule, which nucleic acid is in an antisense orientation with respect to transcription. Preferably, the antisense nucleic acid is complementary with a nucleic acid having at least about 33% homology with SEQ ID NO:1, or a fragment thereof. Preferably, the antisense nucleic acid is complementary with a nucleic acid having at least about 35% identity, more preferably, at least about 40% identity, even more preferably, at least about 45% identity, yet more preferably, at least about 50% identity, more preferably, at least about 55% identity, more preferably, at least about 60% identity, even more preferably, at least about 65% identity, yet more preferably, at least about 70% identity, more preferably, at least about 75% identity, even more preferably, at least about 80% identity, yet more preferably, at least about 85% identity, more preferably, at least about 90% identity, even more preferably, at least about 95% identity, and most preferably, at least about 99% identity with a nucleic acid complementary to a portion or all of a nucleic acid encoding a mammalian REMODEL having the sequence SEQ ID NO:1

Most preferably, the nucleic acid is complementary to a portion or all of a nucleic acid that is SEQ ID NO:1, or a fragment thereof. Such antisense nucleic acid serves to inhibit the expression, function, or both, of an adventitia-inducible and bone expressed REMODEL molecule.

In another aspect, the invention includes an isolated nucleic acid complementary to a portion or all of a nucleic acid encoding a mammalian REMODEL molecule, which nucleic acid is in an antisense orientation with respect to transcription. Preferably, the antisense nucleic acid is complementary with a nucleic acid having at least about 35% identity, more preferably, at least about 40% identity, even more preferably, at least about 45% identity, yet more preferably, at least about 50% identity, more preferably, at least about 55% identity, more preferably, at least about 60% identity, even more preferably, at least about 65% identity, yet more preferably, at least about 70% identity, more preferably, at least about 75% identity, even more preferably, at least about 80% identity, yet more preferably, at least about 85% identity, more preferably, at least about 90% identity, even more preferably, at least about 95% identity, and most preferably, at least about 99% identity with a nucleic acid complementary to a nucleic acid encoding a mammalian REMODEL having the sequence SEQ ID NO:3, or a fragment thereof. Most preferably, the nucleic acid is complementary to a portion or all of a nucleic acid that is SEQ ID NO:3, or a fragment thereof. Such antisense nucleic acid serves to inhibit the expression, function, or both, of an adventitia-inducible and bone expressed REMODEL molecule.

Further, antisense nucleic acids complementary to all or a portion of a nucleic acid encoding REMODEL can be used to detect the expression of REMODEL mRNA in a cell, tissue, and/or organism, using, for example but not limited to, in situ hybridization. Thus, one skilled in the art would understand, based upon the disclosure provided herein, that the invention encompasses antisense nucleic acids that can be used as probes to assess REMODEL expression. Such antisense nucleic acids encompass, but are not limited to, a nucleic acid having the sequence SEQ ID NO:6.

Antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

II. Isolated Polypeptides

The invention also includes an isolated polypeptide comprising a mammalian REMODEL. Preferably, the isolated polypeptide comprising a mammalian REMODEL is at least about 6% homologous to a polypeptide having the amino acid sequence of at least one of SEQ ID NO:2, SEQ ID NO:4, and SEQ ID NO:5. Preferably, the isolated polypeptide is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to at least one of SEQ ID NO:2, SEQ ID NO:4, and SEQ ID NO:5. More preferably, the isolated polypeptide comprising a mammalian REMODEL is at least one of rat REMODEL$_S$, human REMODEL, and rat REMODEL$_L$. Most preferably, the isolated polypeptide comprising a mammalian REMODEL is at least one of SEQ ID NO:2, SEQ ID NO:4, and SEQ ID NO:5.

The invention also includes an isolated polypeptide comprising a mammalian REMODEL molecule. Preferably, the isolated polypeptide comprising a mammalian REMODEL is at least about 6% homologous to a polypeptide having the amino acid sequence of SEQ ID NO:2. More preferably, the isolated polypeptide comprising a mammalian REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to rat $REMODEL_S$ (SEQ ID NO:2) More preferably, the isolated polypeptide comprising a mammalian REMODEL is rat $REMODEL_S$. Most preferably, the isolated polypeptide comprising a mammalian REMODEL molecule is SEQ ID NO:2.

The invention also includes an isolated polypeptide comprising a mammalian REMODEL molecule. Preferably, the isolated polypeptide comprising a mammalian REMODEL molecule is at least about 6% homologous to a polypeptide having the amino acid sequence of SEQ ID NO:4. More preferably, the isolated polypeptide comprising a mammalian REMODEL is at least is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to SEQ ID NO:4. More preferably, the isolated polypeptide comprising a mammalian REMODEL molecule is human REMODEL. Most preferably, the isolated polypeptide comprising a mammalian REMODEL molecule is SEQ ID NO:4.

The invention also includes an isolated polypeptide comprising a mammalian REMODEL molecule. Preferably, the isolated polypeptide comprising a mammalian REMODEL molecule is at least about 6% homologous to a polypeptide having the amino acid sequence of SEQ ID NO:5. More preferably, the isolated polypeptide comprising a mammalian REMODEL is at least about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to rat $REMODEL_L$. More preferably, the isolated polypeptide comprising a mammalian REMODEL molecule is rat $REMODEL_L$. Most preferably, the isolated polypeptide comprising a mammalian REMODEL molecule is SEQ ID NO:5.

The present invention also provides for analogs of proteins or peptides which comprise a REMODEL as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its finction. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are REMODEL peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the REMODEL peptide of the present invention.

A biological property of a REMODEL protein should be construed but not be limited to include, the ability of the expression of the peptide to be induced by TGF-β, the ability of the peptide to be expressed selectively in adventitia, the ability of the peptide to be induced by balloon-injury, the ability of the peptide to be expressed in bone, the ability of the peptide to be expressed in a mouse embryo commencing at about day 11.5 post coitus, the ability of a molecule to be selectively induced in adventitia of injured vessels, to cause phenotypic abnormalities in amphibian embryos such as those disclosed herein (e.g., split tail, abnormal head development, lack of mesoderm development upon FGF-induction, failure of dorsal closure, and the like), to exhibit increased expression only in injured vessel adventitia but not in uninjured vessels nor in the neointima of injured or uninjured vessels, the ability to induce adventitial cell proliferation, to be inhibited by a soluble TGF-β receptor II (which blocks TGF-β signaling), the ability to be induced in fibroblasts during wound healing, the ability to be expressed by osteoblasts during bone formation, the ability to mediate cell death in endothelial cells when overexpressed, the ability to affect cell adhesion and cell-cell interaction, the ability to affect bone density and/or bone growth, and the ability to mediate excessive or insufficient wound healing responses, scarring, keloids, bone formation, fracture healing, and the like.

Further, the invention should be construed to include naturally occurring variants or recombinantly derived mutants of REMODEL sequences, which variants or mutants render the protein encoded thereby either more, less, or just as biologically active as the full-length clones of the invention.

The nucleic acids, and peptides encoded thereby, are useful tools for elucidating the function(s) of REMODEL molecule in a cell. Further, nucleic and amino acids comprising mammalian REMODEL molecule are useful diagnostics which can be used, for example, to identify a compound that affects REMODEL expression and/or TGF-β signaling, and the like, and is a potential therapeutic drug candidate for arterial restenosis, anti-cancer therapy, to promote or inhibit wound healing, to inhibit scar tissue or keloid formation, to promote bone fracture healing, and the like. The nucleic acids, the proteins encoded thereby, or both, can be administered to a mammal to increase or decrease expression of REMODEL in the mammal. This can be beneficial for the mammal in situations where under or over-expression of REMODEL in the mammal mediates a disease or condition associated with altered expression of REMODEL compared with normal expression of REMODEL in a healthy mammal. Such conditions that can be affected by modulating REMODEL expression thereby providing a therapeutic benefit include, but are not limited to, wound healing, arterial injury, ossification, and the like. This is because, as more fully disclosed elsewhere herein, REMODEL is transiently expressed in (myo)fibroblasts in conditions associated with healing and repair following tissue injury. For instance, REMODEL is expressed in osteoblasts bone, which is undergoing constant remodeling. Additionally, over-expression of REMODEL during embryogenesis affects dorsal closure, bone density, and bone growth, and mediates and/or is associated with spina bifida-like effects all of which demonstrate the important biological role(s) of REMODEL.

Additionally, the nucleic and amino acids of the invention can be used to produce recombinant cells and transgenic non-human mammals which are useful tools for the study of REMODEL action, the identification of novel diagnostics and therapeutics for treatment, and for elucidating the cellular role(s) of REMODEL, among other things. For instance, transgenic animals can be used to study bone related, wound healing related, and vascular disease related conditions.

Further, the nucleic and amino acids of the invention can be used diagnostically, either by assessing the level of gene expression or protein expression, to assess severity and prognosis of negative remodeling, arterial restenosis, vessel injury, fibrosis, bone growth, and the like. The nucleic acids and proteins of the invention are also useful in the development of assays to assess the efficacy of a treatment for preventing arterial restenosis, affecting bone density and bone growth, and the like. That is, the nucleic acids and polypeptides of the invention can be used to detect the effect of various therapies on REMODEL expression, thereby ascertaining the effectiveness of the therapies such as, but not limited to, assessment of treatment efficacies for restenosis, anti-fibrotic therapy in any tissue, therapies to promote wound healing in any tissue and therapies for bone formation including bone fracture healing.

III. Vectors

In other related aspects, the invention includes an isolated nucleic acid encoding a mammalian REMODEL operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, supra), and Ausubel et al. (1997, supra).

Expression of REMODEL, either alone or fused to a detectable tag polypeptide, in cells which either do not normally express the REMODEL or which do not express REMODEL fused with a tag polypeptide, may be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding REMODEL may be accomplished by placing the nucleic acid encoding REMODEL, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing REMODEL using a vector allows the isolation of large amounts of recombinantly produced protein. Further, where the lack or decreased level of REMODEL expression causes a disease, disorder, or condition associated with such expression, the expression of REMODEL driven by a promoter/regulatory sequence can provide useful therapeutics including, but not limited to, gene therapy whereby REMODEL is provided. A disease, disorder or condition associated with a decreased level of expression, level of protein, or decreased activity of the protein, for which administration of REMODEL can be useful can include, but is not limited to, bone formation, bone fracture healing, wound healing and repair in any tissue, and the like. Therefore, the invention includes not only methods of inhibiting REMODEL expression, translation, and/or activity, but it also includes methods relating to increasing REMODEL expression, protein level, and/or activity since both decreasing and increasing REMODEL expression and/or activity can be useful in providing effective therapeutics.

One skilled in the art would appreciate, based upon the disclosure provided herein, that because of the selective expression of REMODEL during wound healing in response to injury in any tissue, the promoter for REMODEL can be an excellent choice for targeting nucleic acid expression of a desired gene to a site of tissue injury.

Selection of any particular plasmid vector or other DNA vector is not a limiting factor in this invention and a wide plethora vectors is well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook, supra, and Ausubel, supra.

The invention thus includes a vector comprising an isolated nucleic acid encoding a mammalian REMODEL. The incorporation of a desired nucleic acid into a vector and the choice of vectors is well-known in the art as described in, for example, Sambrook et al., supra, and Ausubel et al., supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding REMODEL can be cloned into various plasmid vectors. However, the present invention should not be construed to be limited to plasmids or to any particular vector. Instead, the present invention should be construed to encompass a wide plethora of vectors which are readily available and/or well-known in the art and no vector at all.

IV. Antisense Molecules and Ribozymes

Further, the invention includes a recombinant cell comprising an antisense nucleic acid which cell is a useful model for elucidating the role(s) of REMODEL in cellular processes. That is, the increased expression of REMODEL in balloon-injured vessels and, more specifically, in the adventitia thereof, indicate that REMODEL is involved in cell proliferation associated with negative remodeling and arterial restenosis. Accordingly, a transgenic cell comprising an antisense nucleic acid complementary to REMODEL but in an antisense orientation is a useful tool for the study of the mechanism(s) of action of REMODEL and its role(s) in the cell and for the identification of therapeutics that ameliorate the effect(s) of REMODEL expression.

One skilled in the art can appreciate, based upon the disclosure provided herein, that an antisense nucleic acid complementary to a nucleic acid encoding REMODEL can be used to transfect a cell and the cell can be studied to determine the effect(s) of altered expression of REMODEL in order to study the function(s) of REMODEL and to identity useful therapeutics and diagnostics.

Further, methods of decreasing REMODEL expression and/or activity in a cell can provide useful diagnostics and/or therapeutics for diseases, disorders or conditions mediated by or associated with increased REMODEL expression, increased level of REMODEL protein in a cell or secretion therefrom, and/or increased REMODEL activity. Such diseases, disorders or conditions include, but are not limited to, any condition associated with fibrosis, e.g., proliferation of fibroblasts with or without excessive fibrous tissue formation, and any condition associated with excessive bone formation or ectopic ossification (malignant or benign), and the like.

One skilled in the art will appreciate that one way to decrease the levels of REMODEL mRNA and/or protein in a cell is to inhibit expression of the nucleic acid encoding the protein. Expression of REMODEL may be inhibited using, for example, antisense molecules, and also by using ribozymes or double-stranded RNA as described in, for example, Wianny and Kernicka-Goetz (2000, Nature Cell Biol. 2:70–75).

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of REMODEL can be designed by incorporating target sequences into the basic ribozyme structure which are complementary to the mRNA sequence of the REMODEL encoded by REMODEL or having at least about 33% homology to at least one of SEQ ID NO:1 and SEQ ID NO:3. Preferably, the sequence is at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to at least one of SEQ ID NO:1 and SEQ ID NO:3. Ribozymes targeting REMODEL may be synthesized using commercially available reagents (Applied Biosystems, Inc., Foster City, Calif.) or they may be genetically expressed from DNA encoding them.

V. Recombinant Cells and Transgenic Non-human Mammals

The invention includes a recombinant cell comprising, inter alia, an isolated nucleic acid encoding REMODEL, an antisense nucleic acid complementary thereto, a nucleic acid encoding an antibody that specifically binds REMODEL, and the like. In one aspect, the recombinant cell can be transiently transfected with a vector (e.g., a plasmid, and the like) encoding a portion of the nucleic acid encoding REMODEL. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, fibroblasts, mouse stem cells, amphibian oocytes, osteoblasts, smooth muscle cells, endothelial cells, and the like.

In one aspect, the recombinant cell comprising an isolated nucleic acid encoding mammalian REMODEL is used to produce a transgenic non-human mammal. That is, the exogenous nucleic acid, or "transgene" as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding a mammalian REMODEL is introduced, including, without limitation, a prokaryotic cell and a eukaryotic cell comprising an isolated nucleic acid encoding mammalian REMODEL.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, negative remodeling, arterial restenosis, and the like. That is, one skilled in the art would appreciate, based upon the disclosure provided herein, that because proliferation of fibroblasts with scar tissue formation is part of any would healing process, selected disease states or processes associated with such proliferation that can be investigated by assessing REMODEL expression include, but are not limited to, wound healing, bone formation, bone fracture healing, and fibrosis of any organ.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding REMODEL can be used to provide REMODEL to a cell, tissue, or whole animal where a higher level of REMODEL can be useful to treat or alleviate a disease, disorder or condition associated with low level of REMODEL expression and/or activity. Such diseases, disorders or conditions can include, but are not limited to, wound healing, bone formation, and bone fracture healing, and the like. Moreover, one skilled in the art would understand that one goal of a wound healing response is to regain mechanical strength and structural support. Remodel is expressed during such a healing response. Additional expression of REMODEL could thus lead to accelerated wound healing, bone growth, and fracture healing. Therefore, the invention includes a cell expressing REMODEL to increase or induce REMODEL expression, translation, and/or activity, where increasing REMODEL expression, protein level, and/or activity can be useful to treat or alleviate a disease, disorder or condition.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding REMODEL and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (i.e., a "knock-out" vector) or which insert (i.e., a "knock-in" vector) a nucleic acid encoding REMODEL, or a fragment thereof, from or into a mammalian genome, respectively. The crucial feature of the targeting vector is that it comprise sufficient portions of two sequences located towards opposite, i.e., 5' and 3', ends of the REMODEL open reading frame (ORF) in the case of a "knock-out" vector, to allow deletion/insertion by homologous recombination to occur such that all or a portion of the nucleic acid encoding REMODEL is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the REMODEL coding region to be used in the targeting vector may be easily selected based upon known methods and following the teachings disclosed herein based on the disclosure provided herein including the nucleic and amino acid sequences of both rat and human REMODEL. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of transgenic a cell where the nucleic acid encoding REMODEL, or a portion thereof, has been deleted and replaced with the neomycin resistance gene by the cell's ability to grow in the presence of G418. However, the present invention should not be construed to be limited to neomycin resistance as a selectable marker. Rather, other selectable markers well-known in the art may be used in the knock-out targeting vector to allow selection of recombinant cells where the REMODEL gene has been deleted and/or inactivated and replaced by the nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a non-human transgenic mamunal comprising an exogenous nucleic acid inserted into a desired site in the genome thereof thereby deleting the coding region of a desired endogenous target gene, i.e., a knock-out transgenic mammal. Further, the invention includes a transgenic non-human mammal wherein an exogenous nucleic acid encoding REMODEL is inserted into a site the genome, i.e., a "knock-in" transgenic mammal. The knock-in transgene inserted may comprise various nucleic acids encoding, for example, a tag polypeptide, a promoter/regulatory region operably linked to the nucleic acid encoding REMODEL not normally present in the cell or not typically operably linked to REMODEL.

The generation of the non-human transgenic mammal of the invention is preferably accomplished using the method which is now described. However, the invention should in no way be construed as being limited solely to the use of this method, in that, other methods can be used to generate the desired knock-out mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp.146–179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146–179). and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693–702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian REMODEL gene may be used in the methods described herein to produce a transgenic mammal or a transgenic cell harboring a transgene comprising a deletion of all or part of that mammalian REMODEL gene. Preferably, a rodent REMODEL gene such as, e.g., rat REMODEL (SEQ ID NO:1), encoding rat $REMODEL_S$ (SEQ ID NO:2) and rat $REMODEL_L$ (SEQ ID NO:5), is used, and human REMODEL (SEQ ID NO:3) gene, is also used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639–645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of REMODEL in the circulating blood of the transgenic animal can be determined, if the protein is secreted, by using, for example, Western blot analysis, or using standard methods for protein detection that are well-known in the art.

Cells obtained from the transgenic mammal of the invention, which are also considered "transgenic cells" as the term is used herein, encompass such as cells as those obtained from the REMODEL (+/−) and (−/−) transgenic non-human mammal described elsewhere herein, are useful systems for modeling diseases and symptoms of mammals which are believed to be associated with altered levels of REMODEL expression such as negative remodeling, arterial restenosis, adventitial fibrosis, wound healing, bone formation, bone density, dorsal closure, spina bifida-like conditions, and any other disease, disorder or condition associated with an altered level of REMODEL expression. Moreover, as a marker of a pathway(s) associated with cell proliferation and cell migration, REMODEL expression levels are also useful indicators in assessment of various diseases, disorders or conditions associated with excessive or impaired wound healing (e.g., skin wound healing) and conditions associated with excessive or impaired bone formation, and the like.

Particularly suitable are cells derived from a tissue of the non-human knock-out or knock-in transgenic mammal described herein, wherein the transgene comprising the REMODEL gene is expressed or inhibits expression of REMODEL in various tissues. By way of example, cell types from which such cells are derived include fibroblasts and like cells of (1) the REMODEL (+/+), (+/−) and (−/−) non-human transgenic liveborn mammal, (2) the REMODEL (+/+), (−/−) or (+/−) fetal animal, and (3) placental cell lines obtained from the REMODEL (+/+), (−/−) and (+/−) fetus and liveborn mammal.

One skilled in the art would appreciate, based upon this disclosure, that cells comprising decreased levels of REMODEL protein, decreased level of REMODEL activity, or both, include, but are not limited to, cells expressing inhibitors of REMODEL expression (e.g., antisense or ribozyme molecules).

Methods and compositions useful for maintaining mammalian cells in culture are well known in the art, wherein the mammalian cells are obtained from a mammal including, but not limited to, cells obtained from a mouse such as the transgenic mouse described herein.

The recombinant cell of the invention can be used to study the effect of qualitative and quantitative alterations in REMODEL levels on cell signal transduction systems. This is because the fact that the data disclosed herein indicate that REMODEL is involved in TGF-β signaling pathways. Further, the recombinant cell can be used to produce REMODEL for use for therapeutic and/or diagnostic purposes. That is, a recombinant cell expressing REMODEL can be used to produce large amounts of purified and isolated REMODEL that can be administered to treat or alleviate a disease, disorder or condition associated with or caused by a decreased level of REMODEL.

Alternatively, recombinant cells expressing REMODEL can be administered in ex vivo and in vivo therapies where administering the recombinant cells thereby administers the protein to a cell, a tissue, and/or an animal. Additionally, the recombinant cells are useful for the discovery of REMODEL ligand(s) and REMODEL signaling pathway(s).

The recombinant cell of the invention may be used to study the effects of elevated or decreased REMODEL levels on cell homeostasis and cell proliferation and/or migration since REMODEL has been hypothesized to play a role in cell migration, adventitial fibrosis, arterial restenosis, negative remodeling, and the like The recombinant cell of the invention, wherein the cell has been engineered such that it does not express REMODEL, or expresses reduced or altered REMODEL lacking biological activity, can also be used in ex vivo and in vivo cell therapies where either an animal's own cells (e.g., fibroblasts, and the like), or those of a syngeneic matched donor, are recombinantly engineered as described elsewhere herein (e.g., by insertion of an antisense nucleic acid or a knock-out vector such that REMODEL expression and/or protein levels are thereby reduced in the recombinant cell), and the recombinant cell is administered to the recipient animal. In this way, recombinant cells that express REMODEL at a reduced level can be administered to an animal whose own cells express increased levels of REMODEL thereby treating or alleviating a disease, disorder or condition associated with or mediated by increased REMODEL expression as disclosed elsewhere herein.

The transgenic mammal of the invention, rendered susceptible to adventitial fibrosis, arterial restenosis, and the like, such as, for example, a REMODEL knock-out mouse, can be used to study the pathogenesis of these diseases and the potential role of REMODEL therein.

Further, the transgenic mammal and/or cell of the invention may be used to further study the subcellular localization of REMODEL.

Also, the transgenic mammal (both +/− and −/− live born and fetuses) and/or cell of the invention may be used to study to role(s) of REMODEL in cell migration and proliferation, and TGF-β signaling to elucidate the target(s) of REMODEL action as well as any receptor(s) and/or ligands that bind with REMODEL to mediate its effect(s) in the cell.

VI. Antibodies

The invention also includes an antibody that specifically binds REMODEL, or a fragment thereof.

One skilled in the art would understand, based upon the disclosure provided herein, that an antibody that specifically binds REMODEL, binds with a protein of the invention, such as, but not limited to rat REMODEL$_S$, human REMODEL, and rat REMODEL$_L$, or an immunogenic portion thereof. In one embodiment, the antibody is directed to rat REMODEL comprising the amino acid sequence of SEQ ID NO:2 and SEQ ID NO:5, and an antibody directed to human REMODEL, comprising the amino acid sequence SEQ ID NO:4.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the REMODEL portion is rendered immunogenic (e.g., REMODEL conjugated with keyhole limpet hemocyanin, KLH) and a portion comprising the respective rodent and/or human REMODEL amino acid residues. The chimeric proteins are produced by cloning the appropriate nucleic acids encoding REMODEL (e.g., SEQ ID NO:1 and SEQ ID NO:3) into a plasmid vector suitable for this purpose, such as but not limited to, pMAL-2 or pCMX.

However, the invention should not be construed as being limited solely to these antibodies or to these portions of the protein antigens. Rather, the invention should be construed to include other antibodies, as that term is defined elsewhere herein, to rat and human REMODEL, or portions thereof. Further, the present invention should be construed to encompass antibodies, inter alia, bind with REMODEL and they are able to bind REMODEL present on Western blots, in immunohistochemical staining of tissues thereby localizing REMODEL in the tissues, and in immunofluorescence microscopy of a cell transiently transfected with a nucleic acid encoding at least a portion of REMODEL.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with mammalian REMODEL. That is, the invention includes immunizing an animal using an immunogenic portion, or antigenic determinant, of the REMODEL protein. Such immunogenic portions can include, but are not limited to, the carboxy-terminal 15 amino acids (GWNSVSRIIIEELPK) (SEQ ID NO:7). The antibodies can be produced by immunizing an animal such as, but not limited to, a rabbit or a mouse, with a protein of the invention, or a portion thereof, or by immunizing an animal using a protein comprising at least a portion of REMODEL, or a fusion protein including a tag polypeptide portion comprising, for example, a maltose binding protein tag polypeptide portion covalently linked with a portion comprising the appropriate REMODEL amino acid residues. One skilled in the art would appreciate, based upon the disclosure provided herein, that smaller fragments of these proteins can also be used to produce antibodies that specifically bind REMODEL.

One skilled in the art would appreciate, based upon the disclosure provided herein, that various portions of an isolated REMODEL polypeptide can be used to generate antibodies to either highly conserved regions of REMODEL or to non-conserved regions of the polypeptide. As disclosed elsewhere herein, REMODEL comprises various conserved domains including, but not limited to, a putative signal peptide from about amino acid residue 1 to about amino acid residue 32 transmembrane domain/signal peptide (amino acid residues from about 1 to 32); a CK2 phosphorylation domain (amino acid residues from about 31 to 34); an N-myristoylation domain (amino acid residues from about 69 to 74); a CK2 phosphorylation domain (amino acid residues from about 99 to 102); an N-myristoylation domain (amino acid residues from about 119 to 124); a PKC phosphorylation domain (amino acid residues from about 146 to 148); an N-myristoylation domain (amino acid residues from about 165 to 170); an N-glycosylation domain (amino acid residues from about 188 to 191); a CK2 phosphorylation domain (amino acid residues from about 197 to 200); an N-myristoylation domain (amino acid residues from about 201 to 206); an N-myristoylation domain (amino acid residues from about 205 to 210); and a CK2 phosphorylation domain (amino acid residues from about 219 to 222). These domains are also present in rat and human REMODELs (see, e.g., SEQ ID NO:2, SEQ ID NO:4, and SEQ ID NO:5).

Once armed with the sequence of REMODEL and the detailed analysis localizing the various conserved and non-conserved domains of the protein, the skilled artisan would understand, based upon the disclosure provided herein, how to obtain antibodies specific for the various portions of a mammalian REMODEL polypeptide using methods well-known in the art or to be developed, as well as methods disclosed herein.

Further, the skilled artisan, based upon the disclosure provided herein, would appreciate that the non-conserved regions of a protein of interest can be more immunogenic than the highly conserved regions which are conserved among various organisms. Further, immunization using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of each REMODEL molecule can be used to produce antibodies that are specific only for that REMODEL and do not cross-react non-specifically with other REMODELs or with other proteins.

Alternatively, the skilled artisan would also understand, based upon the disclosure provided herein, that antibodies developed using a region that is conserved among one or more REMODEL molecule can be used to produce antibodies that react specifically with one or more REMODEL molecule. Methods for producing antibodies that specifically bind with a conserved protein domain which may otherwise be less immunogenic than other portions of the protein are well-known in the art and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one REMODEL and antibodies that specifically bind with more than one REMODEL, including antibodies that specifically bind with all REMODEL.

One skilled in the art would appreciate, based upon the disclosure provided herein, which portions of REMODEL are less homologous with other proteins sharing conserved domains. However, the present invention is not limited to any particular domain; instead, the skilled artisan would understand that other non-conserved regions of the REMODEL proteins of the invention can be used to produce the antibodies of the invention as disclosed herein.

Therefore, the skilled artisan would appreciate, based upon the disclosure provided herein, that the present invention encompasses antibodies that neutralize and/or inhibit REMODEL activity (e.g., by inhibiting necessary REMODEL receptor/ligand interactions) which antibodies can recognize one or more REMODELs, including, but not limited to, rat REMODEL$_S$, rat REMODEL$_L$, and human REMODEL, as well as REMODELs from various species (e.g., mouse REMODEL).

The invention should not be construed as being limited solely to the antibodies disclosed herein or to any particular immunogenic portion of the proteins of the invention. Rather, the invention should be construed to include other antibodies, as that term is defined elsewhere herein, to REMODEL, or portions thereof, or to proteins sharing at least about 6% homology with a polypeptide having the amino acid sequence of at least one of SEQ ID NO:2, SEQ ID NO:4, and SEQ ID NO:5. Preferably, the polypeptide is about 10% homologous, more preferably, at least about 15% homologous, more preferably, at least about 20% homologous, even more preferably, at least about 25% homologous, more preferably, at least about 30% homologous, preferably, at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to at least one of rat REMODEL$_S$ (SEQ ID NO:2), human REMODEL (SEQ ID NO:4), and rat REMODEL$_L$ (SEQ ID NO:5). More preferably, the polypeptide that specifically binds with an antibody specific for mammalian REMODEL is at least one of rat REMODEL$_S$ (SEQ ID NO:2), human REMODEL (SEQ ID NO:4), and rat REMODEL$_L$ (SEQ ID NO:5). Most preferably, the polypeptide that specifically binds specifically binds with a mammalian REMODEL is at least one of SEQ ID NO:2, SEQ ID NO:4, and SEQ ID NO:5.

Further, the skilled artisan would appreciate, based upon the disclosure provided herein, that amino acid sequences that may elicit antibodies that non-specifically cross-react with a non-REMODEL protein can also be excluded from use as immunogens. For example, such amino acid sequences include, but are not limited to, an amino acid sequence comprising collagen alpha-2 (IV) chain precursor (GenBank Acc. No. P27393), which shares about 62% identity with REMODEL over a 35 amino acid stretch. Thus, such a portion sharing at least about 62% identity over 35 amino acids of REMODEL would not be used to produce the antibodies of the invention.

The invention encompasses polyclonal, monoclonal, synthetic antibodies, and the like. One skilled in the art would understand, based upon the disclosure provided herein, that the crucial feature of the antibody of the invention is that the antibody bind specifically with REMODEL. That is, the antibody of the invention recognizes REMODEL, or a fragment thereof (e.g., an immunogenic portion or antigenic determinant thereof), as demonstrated by antibody binding REMODEL on Western blots, in immunostaining of cells, and/o immunoprecipitation of REMODEL, using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art.

In addition, the antibody can be used to decrease the level of REMODEL in a cell thereby inhibiting the effect(s) of REMODEL in a cell. Thus, by administering the antibody to a cell or to the tissues of an animal or to the animal itself, the required REMODEL receptor/ligand interactions are therefore inhibited such that the effect of REMODEL-mediated signaling are also inhibited. One skilled in the art would understand, based upon the disclosure provided herein, that detectable effects upon inhibiting REMODEL ligand/receptor interaction using an anti-REMODEL antibody can include, but are not limited to, decreased proliferation of cells, decreased cell migration, decreased negative modeling, decreased adventitial fibrosis, decreased arterial restenosis, decreased fibrosis in any organ or tissue, decreased ossification or bone formation, and the like.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109–115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein.

Further, the antibody of the invention may be "humanized" using the technology described in, for example, Wright et al. (supra), and in the references cited therein, and in Gu et al. (1997, Thrombosis and Hematocyst 77:755–759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

VII. Compositions

The invention includes a composition comprising an isolated nucleic complementary to a nucleic acid, or a portion thereof, encoding a mammalian REMODEL, which is in an antisense orientation with respect to transcription. Preferably, the composition comprises a pharmaceutically acceptable carrier.

The invention includes a composition comprising an isolated mammalian REMODEL polypeptide as described herein. Preferably, the composition comprises a pharmaceutically-acceptable carrier.

The invention also includes a composition comprising an antibody that specifically binds REMODEL. Preferably, the composition comprises a pharnaceutically-acceptable carrier.

The invention further includes a composition comprising an isolated nucleic acid encoding a mammalian REMODEL. Preferably, the composition comprises a pharmaceutically acceptable carrier.

The compositions can be used to administer REMODEL to a cell, a tissue, or an animal or to inhibit expression of REMODEL in a cell, a tissue, or an animal. The compositions are useful to treat a disease, disorder or condition mediated by altered expression of REMODEL such that decreasing or increasing REMODEL expression or the level of the protein in a cell, tissue, or animal, is beneficial to the animal. That is, where a disease, disorder or condition in an animal is mediated by or associate with altered level of REMODEL expression or protein level, the composition can be used to modulate such expression or protein level of REMODEL.

For administration to the mammal, a polypeptide, or a nucleic acid encoding it, and/or an antisense nucleic acid complementary to all or a portion thereof, can be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer REMODEL and/or a nucleic acid encoding the same according to the methods of the invention.

Compounds which are identified using any of the methods described herein may be formulated and administered to a mammal for treatment of arterial restenosis, adventitial fibrosis, fibrosis in any organ or tissue, negative remodeling, excessive bone formation, excessive ossification, and the like, are now described.

The invention encompasses the preparation and use of pharmaceutical compositions comprising a compound useful for treatment of arterial restenosis, adventitial fibrosis, negative remodeling, and the like, as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, anti-ftngal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension.

Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0. 1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

VIII. Methods

A. Methods of Identifying Useful Compounds

The present invention further includes a method of identifying a compound that affects expression of REMODEL in a cell. The method comprises contacting a cell with a test compound and comparing the level of expression of REMODEL in the cell so contacted with the level of expression of REMODEL in an otherwise identical cell not contacted with the compound. If the level of expression of REMODEL is higher or lower in the cell contacted with the test compound compared to the level of expression of REMODEL in the otherwise identical cell not contacted with the test compound, this is an indication that the test compound affects expression of REMODEL in a cell.

Similarly, the present invention includes a method of identifying a compound that reduces expression of REMODEL in a cell. The method comprises contacting a cell with a test compound and comparing the level of expression of REMODEL in the cell contacted with the compound with the level of expression of REMODEL in an otherwise identical cell, which is not contacted with the compound. If the level of expression of REMODEL is lower in the cell contacted with the compound compared to the level in the cell that was not contacted with the compound, then that is an indication that the test compound affects reduces expression of REMODEL in a cell.

One skilled in the art would appreciate, based on the disclosure provided herein, that the level of expression of REMODEL in the cell may be measured by determining the level of expression of mRNA encoding REMODEL. Alternatively, the level of expression of mRNA encoding REMODEL can be determined by using immunological methods to assess REMODEL production from such mRNA as exemplified herein using Western blot analysis using an anti-REMODEL antibody of the invention. Further, nucleic acid-based detection methods, such as Northern blot and PCR assays and the like, can be used as well. In addition, the level of REMODEL activity in a cell can also be assessed by determining the level of various parameters which can be affected by REMODEL activity such as, for example, the level of cell proliferation and/or migration, the level of expression in adventitia, the level of adventitial fibrosis, the level of fibrosis in other organs (e.g., lung, liver, among others), the level of arterial restenosis, the level of ossification, the level of bone formation and fracture healing, the level of osteoblast proliferation, and the like.

Thus, one skilled in the art would appreciate, based upon the extensive disclosure and reduction to practice provided herein, that there are a plethora of methods that are well-known in the art, which can be used to asses the level of expression of REMODEL in a cell including those disclosed herein and others which may be developed in the future.

Further, one skilled in the art would appreciate based on the disclosure provided herein that, as disclosed in the examples below, a cell which lacks endogenous REMODEL expression can be transfected with a vector comprising an isolated nucleic acid encoding REMODEL whereby expression of REMODEL is effected in the cell. The transfected cell is then contacted with the test compound thereby allowing the determination of whether the compound affects the expression of REMODEL. Therefore, one skilled in the art armed with the present invention would be able to, by selectively transfecting a cell lacking detectable levels of REMODEL using REMODEL-expressing vectors, identify a compound which selectively affects REMODEL expression.

The skilled artisan would further appreciate, based upon the disclosure provided herein, that where an isolated nucleic acid encoding REMODEL is administered to a cell lacking endogenous detectable levels of REMODEL expression such that detectable REMODEL is produced by the cell, the isolated nucleic acid can comprise an additional nucleic acid encoding (e.g., a tag polypeptide) covalently linked thereto. This allows the detection of REMODEL expression by detecting the expression of the tag polypeptide. Thus, the present invention encompasses methods of detecting REMODEL expression by detecting expression of another molecule which is co-expressed with REMODEL.

The invention includes a method of identifying a protein that specifically binds with REMODEL. That is, one skilled in the art would appreciate, based upon the disclosure provided herein, that REMODEL, which comprises several myristoylation domains. Further, REMODEL comprises a putative signal peptide indicating the molecule can be secreted from a cell. These data indicate that REMODEL likely effects its biological function(s) by specifically binding with at least one protein, preferably a REMODEL receptor, another REMODEL molecule, and/or a REMODEL ligand. Thus, the invention encompasses methods, which are well-known in the art or to be developed, for identifying a protein that specifically binds with and/or associates with REMODEL. Such methods include, but are not limited to, protein binding assays wherein the target protein, i.e., REMODEL, is immobilized on an appropriate support and incubated under conditions that allow REMODEL binding with a REMODEL-associated protein. REMODEL can be immobilized on a support using standard methods such as, but not limited to, production of REMODEL comprising a glutathione-S-transferase (GST) tag, a maltose binding protein (MBP) tag, or a $His_6$-tag, where the fusion protein is then bound to glutathione-Sepharose beads, a maltose-column, or a nickel chelation resin (e.g., His-Bind resin, Novagen, Madison, Wis.), respectively. The solid support is washed to remove proteins which may be non-specifically bound thereto and any REMODEL-associated protein can then be dissociated from the matrix thereby identifying a REMODEL-associated protein.

In addition, a protein that specifically binds with REMODEL, e.g., a receptor, a ligand, and/or other REMODEL-associated protein, can be identified using, for example, a yeast two hybrid assay. Yeast two hybrid assay methods are well-known in the art and can be performed using commercially available kits (e.g, MATCHMAKER™ Systems, Clontech Laboratories, Inc., Palo Alto, Calif., and other such kits) according to standard methods. Therefore, once armed with the teachings provided herein, e.g., the full amino and nucleic acid sequences of the "bait" protein, REMODEL, one skilled in the art can easily identify a protein that specifically binds with REMODEL such as, but not limited to, a REMODEL receptor protein, a REMODEL ligand, and the like.

One skilled in the art would understand, based upon the disclosure provided herein, that the invention encompasses any molecule identified using the methods discussed elsewhere herein. That is, molecules that associate with REMODEL, such as but not limited to, a REMODEL receptor protein, a REMODEL ligand protein, or both, can be used to develop therapeutics and diagnostics for diseases, disorders or conditions mediated by REMODEL interaction with a REMODEL-associated protein such as negative remodeling, arterial restenosis, adventitial fibrosis, excessive wound healing responses, scarring, keloids, excessive bone formation, fracture healing, ectopic ossification, excessive fibrous tissue formation, failure of dorsal closure, spina bifida-like effects, and the like. That is, one skilled in the art would appreciate, as more fully set forth elsewhere herein in discussing antibodies that specifically bind with REMODEL, that a REMODEL-associated protein can be used to develop therapeutics that inhibit REMODEL activity in a cell by inhibiting necessary REMODEL receptor/ligand interactions and other REMODEL binding interactions, which are required for REMODEL activity.

REMODEL-associated proteins identified by the above-disclosed methods can be used directly to inhibit REMODEL interactions by contacting a cell with the REMODEL-associated protein, or a portion thereof, or they can be used to develop antibodies and/or peptidomimetics that can inhibit the REMODEL-associated interaction with REMODEL thereby inhibiting REMODEL function and activity. Thus, REMODEL-associated proteins, including a REMODEL receptor/ligand protein, are useful and are encompassed by the invention.

B. Methods of Treating or Alleviating a Disease, Disorder or Condition Associated with or Mediated by REMODEL Expression The invention includes a method of alleviating a disease, disorder or condition mediated by malexpression of REMODEL. The method comprises administering an antisense nucleic acid complementary to a nucleic acid encoding REMODEL to a patient afflicted with a disease, disorder or condition mediated by increased REMODEL expression compared to the level of REMODEL expression in otherwise identical but normal tissue, i.e., tissue which does not exhibit any detectable clinical parameters associated with the disease, disorder or condition being treated or alleviated. This, in turn, mediates a decrease in REMODEL expression thereby alleviating a disease, disorder or condition mediated by malexpression of REMODEL. Such diseases, disorder or conditions include, but are not limited to, negative remodeling, arterial restenosis, adventitial fibrosis, excessive wound healing responses, scarring, keloids, abnormal bone formation and/or bone density, fracture healing, ectopic ossification, excessive fibrous tissue formation, lack of dorsal closure, spina bifida-like conditions, and the like.

The data disclosed herein demonstrate that REMODEL expression is induced in fibroblasts following an injury. As such, REMODEL is part of any wound healing process which is characterized by granulation tissue formation, proliferation, and migration of fibroblasts with subsequent apoptosis of these cells extracellular matrix production. Although the wound healing response/process is a normal physiologic response to injury, there are many conditions where an excessive wound healing response leads to symptoms or disease. Thus, the skilled artisan would appreciate, based upon the disclosure provided herein, that because the wound healing response is similar for all organs and tissues, the effects of expression of REMODEL are similar independent of where the injury occurred. Excessive wound healing would result in various conditions depending on the situs of injury such that, for example, in an artery, excessive wound healing would result in negative remodeling with loss of vessel diameter due to adventitial fibrosis. The formation of scars and keloids is an excessive fibrotic reaction associated with excessive wound healing. Chronic inflammatory conditions often lead to organ fibrosis, e.g., liver fibrosis and lung fibrosis.

The data disclosed herein demonstrate that when REMODEL is inhibited using an antisense nucleic acid, the cell exhibited an altered morphology indicating decreased cell adhesion to the substratum and decreased cell-cell interaction. Further, the data demonstrate that REMODEL antisense expression is associated with and/or mediates cell turnover. Therefore, the data further indicate that REMODEL is involved in and/or is associated with processes involving cell turnover, cell adhesion and cell-cell interaction such as, but not limited to, negative remodeling, adventitial fibrosis, and the like.

The expression of REMODEL in osteoblasts suggests a role for this gene in bone formation and indicates a role for REMODEL malexpression. That is, bone formation can occur in undesirable sites, such as after trauma, leading to ossification of otherwise non-calcifying tissues, for example, skeletal muscle and vascular tissues. Indeed, calcification is an important problem involving prostheses and implants, such as, but not limited to, heart valves. Therefore, the data disclosed herein suggest that REMODEL expression plays a role in bone formation, ossification, and calcification in response to trauma and/or injury.

Further, over-expression of REMODEL mediates and/or is associated with lack of dorsal closure, abnormal bone density and bone growth, and spina bifida-like phenotype. Thus, the data disclosed herein suggest that REMODEL plays an important role(s) including, but not limited to, a role in bone formation, bone density, dorsal closure, and the like.

Antisense nucleic acids that inhibit expression of REMODEL can therefore also be used for the manufacture of a medicament for treatment of a disease, disorder or condition mediated by increased expression of REMODEL, when compared with expression of REMODEL in a cell and/or a patient not afflicted with the disease, disorder or condition.

One skilled in the art would understand, based upon the disclosure provided herein, that because reducing expression of REMODEL can mediate a beneficial effect in a patient afflicted with excessive wound healing resulting in negative remodeling, adventitial fibrosis, fibrosis in any organ or tissue (e.g., liver fibrosis and lung fibrosis), scarring, keloids, fibrotic reaction associated with excessive wound healing, excessive bone formation, ectopic ossification, and the like, decreased REMODEL expression can be useful for treating such diseases, disorders, or conditions. This is because, as disclosed elsewhere herein, increased expression of REMODEL is associated with abnormal cell proliferation associated with arterial restenosis, negative remodeling, adventitial fibrosis, fibrosis in any organ or tissue (e.g., liver, lung, among others), excessive bone formation, ectopic ossification, altered cell adhesion and cell-cell interaction, cell turnover, and the like. Thus, one skilled in the art would appreciate, based upon the disclosure provided herein, that inhibition of REMODEL expression can inhibit the deleterious effects of REMODEL malexpression.

One skilled in the art would understand, based upon the disclosure provided herein, that since reduced REMODEL expression can mediate a beneficial effect, methods of decreasing expression of REMODEL, decreasing the level of REMODEL polypeptide present in the cell, and/or decreasing the activity of REMODEL in a cell (using, e.g., antisense nucleic acids, ribozymes, antibodies, and the like), can be used to treat and/or alleviate a disease, disorder or condition associated with altered expression of REMODEL where a lower level of REMODEL would provide a benefit such as in preventing decreased bone growth and/or density, failure of dorsal closure, and spina bifida-like phenotype such as are associated with over-expression of REMODEL as disclosed elsewhere herein. Thus, whether an antisense nucleic acid or a blocking antibody is administered, the crucial feature of the present invention is that the expression of REMODEL be reduced in a cell.

Techniques for inhibiting expression of a nucleic acid in a cell are well known in the art and encompass such methods as disclosed herein (e.g., inhibition using an antibody, an antisense nucleic acid, and the like). Other techniques useful for inhibiting expression of a nucleic acid encoding REMODEL include, but are not limited to, using nucleotide reagents that target specific sequences of the REMODEL promoter, and the like.

One skilled in the art would understand, based upon the disclosure provided herein, that it may be useful to increase the level or activity of REMODEL in a cell. That is, based on the data disclosed herein demonstrating the association between REMODEL expression and wound healing and bone growth, it is likely, without wishing to be bound by any particular theory, that overexpression or an increase in REMODEL activity can result in accelerated wound healing and bone growth. This can be useful to treat or alleviate a disease, disorder of condition associated with or mediated by decreased expression, level, or activity of REMODEL (e.g., various forms of organ and tissue damage including bone fractures), when compared to the expression, level or activity of REMODEL in otherwise identical cell, tissue, or animal that does not suffer from the disease, disorder or condition, by administering REMODEL. Such diseases, disorders or conditions include, but are not limited to, tissue damage or injury, including bone fracture, wound healing, and the like.

The data disclosed herein suggest that over- and under-expression of REMODEL are associated with disease, disorder or condition such that a method of decreasing or increasing the level of REMODEL can produce a benefit.

Whether expression of REMODEL, levels of the polypeptide, or its activity, is increased or decreased, one skilled in the art would appreciate, based on this disclosure, that methods of reducing or inducing REMODEL of the invention encompass administering a recombinant cell that either expresses or lacks expression of REMODEL.

In another embodiment of the invention, an individual suffering from a disease, disorder or a condition that is associated with or mediated by REMODEL expression can be treated by supplementing, augmenting and/or replacing defective cells with cells that lack REMODEL expression. The cells can be derived from cells obtained from a normal syngeneic matched donor or cells obtained from the individual to be treated. The cells may be genetically modified to inhibit REMODEL expression.

An example of a disease, disorder or a condition associated with or mediated by REMODEL expression is, organ and tissue fibrosis (e.g., adventitial, lung, liver, and retroperitoneal fibrosis, and the like), hypertrophic scars, keloids, excessive bone formation, ectopic ossification, and the like.

In addition to replacing defective cells with repaired cells or normal cells from syngeneic, immunologically-matched donors, the method of the invention may also be used to facilitate expression of a desired protein that when secreted in the an animal, has a beneficial effect. That is, cells may be isolated, furnished with a gene encoding REMODEL and introduced into the donor or into a syngeneic matched recipient. Expression of the REMODEL exerts a therapeutic effect.

One skilled in the art would understand, based upon the disclosure provided herein, that secretion of REMODEL from a cell can be effected according to standard methods well-known in the art. Such methods include, but are not limited to, covalently linking a nucleic acid encoding a signal peptide of a secreted molecule (e.g., insulin; MALLVHFLPLLALLALWEPKPTQA [SEQ ID NO:8]) to the 5' end of an isolated nucleic acid encoding REMODEL.

This aspect of the invention relates to gene therapy in which therapeutic amounts of REMODEL are administered to an individual.

According to some aspects of the present invention, recombinant cells transfected with either nucleic acid encoding REMODEL, antisense nucleic acids, or a knock-out targeting vector of the invention, can be used as cell therapeutics to treat a disease, disorder or a condition characterized by expression of REMODEL, or the lack thereof.

In particular, a gene construct that comprises a heterologous gene which encodes REMODEL is introduced into cells. These recombinant cells are used to purify isolated REMODEL, which was is administered to an animal. One skilled in the art would understand, based upon the disclosure provided herein, that instead of administering an isolated REMODEL polypeptide, REMODEL can be administered to a mammal in need thereof by administering to the mammal the recombinant cells themselves. This will benefit the recipient individual who will benefit when the protein is expressed and secreted by the recombinant cell into the recipient's system.

According to the present invention, gene constructs comprising nucleotide sequences of the invention are introduced into cells. That is, the cells, referred to herein as "recombinant cells," are genetically altered to introduce a nucleic acid encoding REMODEL or a nucleic acid that inhibits REMODEL expression in and/or secretion by the recombinant cell (e.g., an antisense REMODEL nucleic acid, a nucleic acid encoding an anti-REMODEL antibody, and the like), thereby mediating a beneficial effect on an recipient to which the recombinant cell is administered. According to some aspects of the invention, cells obtained from the same individual to be treated or from another individual, or from a non-human animal, can be genetically altered to replace a defective REMODEL gene and/or to introduce a REMODEL gene whose expression has a beneficial effect on the individual, or to inhibit REMODEL expression which can have a beneficial effect on the individual.

In some aspects of the invention, an individual suffering from a disease, disorder or a condition can be treated by supplementing, augmenting and/or replacing defective or deficient nucleic acid encoding REMODEL by providing an isolated recombinant cells containing gene constructs that include normal, functioning copies of a nucleic acid encoding REMODEL. This aspect of the invention relates to gene therapy in which the individual is provided with a nucleic encoding REMODEL for which they are deficient in presence and/or function. The isolated nucleic acid encoding REMODEL provided by the cell compensates for the defective REMODEL expression of the individual, because, when the nucleic acid is expressed in the individual, a protein is produced which serves to alleviate or otherwise treat the disease, disorder or condition in the individual. Such nucleic acid preferably encodes a REMODEL polypeptide that is secreted from the recombinant cell.

In all cases in which a gene construct encoding REMODEL is transfected into a cell, the nucleic acid is operably linked to an appropriate promoter/regulatory sequence which is required to achieve expression of the nucleic acid in the recombinant cell. Such promoter/regulatory sequences include but are not limited to, constitutive and inducible and/or tissue specific and differentiation specific promoters, and are discussed elsewhere herein. Constitutive promoters include, but are not limited to, the cytomegalovirus immediate early promoter and the Rous sarcoma virus promoter. In addition, housekeeping promoters such as those which regulate expression of housekeeping genes may also be used. Other promoters include those which are preferentially expressed in cells of the central nervous system, such as, but not limited the promoter for the gene encoding glial fibrillary acidic protein. In addition, promoter/regulatory elements may be selected such that gene expression is inducible. For example, a tetracycline inducible promoter may be used (Freundlich et al., 1997, Meth. Enzymol. 283:159–173).

The gene construct is preferably provided as an expression vector which includes the coding sequence of a mammalian REMODEL of the invention operably linked to essential promoter/regulatory sequences such that when the vector is transfected into the cell, the coding sequence is expressed by the cell. The coding sequence is operably linked to the promoter/regulatory elements necessary for expression of the sequence in the cells. The nucleotide sequence that encodes the protein may be cDNA, genomic DNA, synthesized DNA or a hybrid thereof or an RNA molecule such as mRNA.

The gene construct, which includes the nucleotide sequence encoding REMODEL operably linked to the promoter/regulatory elements, may remain present in the cell as a ftmctioning episomal molecule or it may integrate into the chromosomal DNA of the cell. Genetic material may be introduced into cells where it remains as separate genetic material in the form of a plasmid. Alternatively, linear DNA which can integrate into a host cell chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

In order for genetic material in an expression vector to be expressed, the promoter/regulatory elements must be operably linked to the nucleotide sequence that encodes the protein. In order to maximize protein production, promoter/regulatory sequences may be selected which are well suited for gene expression in the desired cells. Moreover, codons may be selected which are most efficiently transcribed in the cell. One having ordinary skill in the art can produce recombinant genetic material as expression vectors which are functional in the desired cells.

It is also contemplated that promoter/regulatory elements may be selected to facilitate tissue specific expression of the protein. Thus, for example, specific promoter/regulatory sequences may be provided such that the heterologous gene will only be expressed in the tissue where the recombinant cells are implanted. Additionally, the skilled artisan would appreciate, based upon the disclosure provided herein, that the REMODEL promoter can be operably linked to a nucleic acid of interest thereby directing the expression of the nucleic acid at the site of tissue or organ injury and wounding. More specifically, the REMODEL promoter can be used, but is not limited, to direct expression of an angiogenic growth factor to promote angiogenesis after myocardial infarction. Similarly, the REMODEL promoter can drive expression of a nucleic acid of interest where such expression is beneficial where tissue ischemia and impaired wound healing are a problem (e.g., ulcerations of the skin, and the like).

One skilled in the art would understand, based upon the disclosure provided herein, that the preferred tissues where the expression or lack of expression of REMODEL is to be targeted include, but are not limited to, ulcerations of the skin, bone fractures, and the like. In addition, promoter/regulatory elements may be selected such that gene expression is inducible. For example, a tetracycline inducible promoter may be used (Freundlich et al., 1997, Meth. Enzymol. 283:159–173).

Without wishing to be bound by any particular theory, the nucleic acid encoding REMODEL preferably includes a putative signal sequence as disclosed elsewhere herein (e.g., amino acids 1 to 32 of human REMODEL; SEQ ID NO:3) and amino acids 1 to 32 of rat $REMODEL_S$ (SEQ ID NO:1), which may direct the transport and secretion of the REMODEL encoded by the isolated nucleic acid in the recombinant cell. The signal sequence is likely processed and removed upon secretion of the mature REMODEL protein from the cell. Alternatively, without wishing to be bound by any particular theory, the putative signal sequence may not be cleaved, but may instead be a transmembrane domain.

In addition to providing cells with recombinant genetic material that either corrects a genetic defect in the cells, that encodes a protein which is otherwise not present in sufficient quantities and/or functional condition so that the genetic material corrects a genetic defect in the individual, and/or that encodes a protein which is useful as beneficial in the treatment or prevention of a particular disease, disorder or condition associated therewith, and that inhibits expression of REMODEL in the cell (e.g., a knock-out targeting vector, an antisense nucleic acid, and the like), genetic material can also be introduced into the recombinant cells used in the present invention to provide a means for selectively terminating such cells should such termination become desirable. Such means for targeting recombinant cells for destruction may be introduced into recombinant cells.

According to the invention, recombinant cells can be furnished with genetic material which renders them specifically susceptible to destruction. For example, recombinant cells may be provided with a gene that encodes a receptor that can be specifically targeted with a cytotoxic agent. An expressible form of a gene that can be used to induce selective cell death can be introduced into the recombinant cells. In such a system, cells expressing the protein encoded by the gene are susceptible to targeted killing under specific conditions or in, the presence or absence of specific agents. For example, an expressible form of a herpes virus thymidine kinase (herpes tk) gene can be introduced into the recombinant cells and used to induce selective cell death. When the introduced genetic material that includes the herpes tk gene is introduced into the individual, herpes tk will be produced. If it is desirable or necessary to kill the implanted recombinant cells, the drug gangcyclovir can be administered to the individual which will cause the selective killing of any cell producing herpes tk. Thus, a system can be provided which allows for the selective destruction of implanted recombinant cells.

One skilled in the art would understand, based upon the disclosure provided herein, that the present invention encompasses production of recombinant cells to either provide REMODEL to or inhibit REMODEL expression in a mammal. That is, the cells can be used to administer REMODEL to an animal or to deliver a molecule (e.g., a knock-out targeting vector, an antisense nucleic acid, a ribozyme, and antibody that specifically binds with REMODEL, and the like).

Administration of REMODEL to an animal can be used as a model system to study the mechanism of action of REMODEL or to develop model systems useful for the development of diagnostics and/or therapeutics for diseases, disorders or conditions associated with REMODEL expression.

Further, the delivery of REMODEL to an animal mediated by administration of recombinant cells expressing and secreting REMODEL can also be used to treat or alleviate a disease, disorder or condition where increasing the level of AOBE mediates a therapeutic effect. More specifically, administration of REMODEL to an animal by administering a recombinant cell expressing a nucleic acid encoding REMODEL can be useful for treatment of impaired wound healing, bone fracture, and impaired bone formation, among other things.

Alternatively, administration of recombinant cells comprising a nucleic acid the expression of which inhibits or reduces REMODEL expression, activity, and/or secretion from a cell, can be used as a model for the development of diagnostics and/or therapeutics useful for diseases, disorders or conditions associated with or mediated by REMODEL expression, activity, and/or secretion. The present invention encompasses that the recombinant cells can produce the molecule that inhibits REMODEL expression thereby providing such molecule to the animal. Alternatively, without wishing to be bound by any particular theory, the recombinant cells themselves, which are otherwise functional cells, except for the inability to express REMODEL, can perform the functions of otherwise identical but non-recombinant cells, without being subject to the REMODEL signaling pathway.

Cells, both obtained from an animal, from established cell lines that are commercially available or to be developed, or primary cells cultured in vitro, can be transfected using well known techniques readily available to those having ordinary skill in the art. Thus, the present invention is not limited to obtaining cells from a donor animal or from the patient animal itself. Rather, the invention includes using any cell that can be engineered using a nucleic acid of the invention such that the recombinant cell either expresses REMODEL (where it did not express REMODEL prior to being engineered, or where the cell produced REMODEL at a different level prior to the introduction of the nucleic acid into the cell) or the recombinant cell does not express REMODEL or expresses it at a lower level (where it expressed REMODEL before or expressed REMODEL at a different level prior to introduction of the nucleic acid into the cell).

Nucleic acids can be introduced into the cells using standard methods which are employed for introducing a gene construct into cells which express the protein encoded by the gene or which express a molecule that inhibits REMODEL expression. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA having a desired sequence into the cell. In some embodiments, recombinant retrovirus vectors are used to introduce DNA having a desired sequence into the cell. In some embodiments, standard calcium phosphate, DEAE dextran or lipid carrier mediated transfection techniques are employed to incorporate a desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into cells. A second gene is usually co-transfected with and/or covalently linked to the nucleic acid encoding REMODEL, or knock-out targeting vector or antisense molecule thereto. The second gene is frequently a selectable antibiotic-resistance gene. Transfected recombinant cells can be selected by growing the cells in an antibiotic that kills cells that do not take up the selectable gene. In most cases where the two genes are unlinked and co-transfected, the cells that survive the antibiotic treatment contain and express both genes.

Where an isolated REMODEL polypeptide, an antibody that specifically binds with REMODEL, a REMODEL antisense nucleic acid, and/or recombinant cells of the invention are administered to an animal either to increase or reduce the level of REMODEL present in the animal, one skilled in the art would understand, based upon the disclosure provided herein, that the amount of the polypeptide, nucleic acid, antibody, or cell to be administered to the animal can be titrated by assessing the level of expression of REMODEL or the level of REMODEL polypeptide or nucleic acid encoding REMODEL present in the tissues of the animal.

Methods for assessing the level of REMODEL (e.g., using anti-REMODEL antibodies in Western blot or other immune-based analyses such as ELISA) and/or methods for assessing the level of REMODEL expression in a cell and/or tissues (e.g., using Northern blot analysis, RT-PCR analysis, in situ hybridization, and the like) are disclosed herein or are well known to those skilled in the art. Such assays can be used to determine the "effective amount" of REMODEL (whether using an isolated nucleic acid, antibody, antisense nucleic acid, ribozyme, recombinant cell, and the like) to be administered to the animal in order to reduce or increase the level of REMODEL to a desired level.

C. Methods of Diagnosis and Assessment of Therapies

The present invention includes methods of diagnosis certain diseases, disorders, or conditions such as, but not limited to, negative remodeling, arterial restenosis, adventitial fibrosis, excessive wound healing responses, scarring, keloids, excessive bone formation, fracture healing, ectopic ossification (malignant and benign), fibrosis in any organ or tissue (e.g., liver fibrosis and lung fibrosis), altered bone density, altered bone growth, and the like, which are associated with or mediated by malexpression of REMODEL.

The invention includes a method of diagnosing tissue damage, negative remodeling, arterial restenosis, adventitial fibrosis, excessive wound healing responses, scarring, keloids, excessive bone formation, fracture healing, ectopic ossification (malignant and benign), fibrosis in any organ or tissue (e.g., liver fibrosis and lung fibrosis), altered bone density, altered bone growth, and the like, in a previously undiagnosed patient mammal. This is because, as demonstrated by the data disclosed herein, there is a correlation between altered expression of REMODEL, when compared to expression of REMODEL in otherwise identical but undamaged, normal tissue, and tissue injury, negative remodeling, arterial restenosis, adventitial fibrosis, excessive wound healing responses, scarring, keloids, excessive bone formation, fracture healing, ectopic ossification (malignant and benign), fibrosis in any organ or tissue (e.g., liver fibrosis and lung fibrosis), altered bone density, altered bone growth, and the like, such that assessing the level of REMODEL expression is a useful diagnostic for these diseases, disorders, or conditions associated with altered expression of REMODEL.

The method comprises obtaining a biological sample from the mammal and comparing the level of REMODEL (expression, amount, activity) in the sample with the level of REMODEL in a sample from a normal person who is not afflicted with tissue damage, ectopic ossification, and organ fibrosis. A higher level of REMODEL in the sample from the patient compared with the level of REMODEL in the sample obtained from a person not afflicted with tissue damage, ectopic ossification, and organ fibrosis an indication that the patient is afflicted with tissue damage, ectopic ossification, and organ fibrosis. This is because, as disclosed elsewhere herein, an increased level of REMODEL expression is associated with tissue damage, ectopic ossification, organ fibrosis, bone mineralization, skin wounding, bone density and/or bone growth, lack of dorsal closure, spina bifida-like phenotype, and vascular injury.

In one aspect, the biological sample is selected from the group consisting of a lung biopsy, an aorta sample, a smooth muscle cell (SMC) sample, an endarterectomy sample, a liver biopsy, any biopsy from a wound, and the like.

The invention includes a method of assessing the effectiveness of a treatment for arterial restenosis in a mammal. The method comprises assessing the level of REMODEL expression, amount, and/or activity, before, during and after a specified course of treatment for arterial stenosis since arterial restenosis and/or arterial fibrosis is associated with increased REMODEL expression. This is because, as stated previously elsewhere and demonstrated by the data disclosed herein, REMODEL expression, amount and/or activity is associated with or mediates decreased increased cell proliferation which is feature of certain disease states (e.g., negative remodeling, adventitial fibrosis and arterial restenosis). Thus, assessing the effect of a course of treatment upon REMODEL expression/amount/activity indicates the efficacy of the treatment such that a lower level of REMODEL expression, amount, or activity indicates that the treatment method is successful.

The data disclosed herein should allow the identification and characterization of the REMODEL ligand/receptor. This is useful since antagonism of the REMODEL ligand, receptor, or both, should provide useful in treatment of diseases, disorders or conditions mediated by REMODEL ligand/receptor signaling such as, but not limited to, arterial restenosis, negative remodeling, adventitial fibrosis, fibrosis in any organ or tissue (e.g., liver, lung, among others), hypertrophic scar tissue (i.e., keloids), excessive bone formation, ectopic ossification (malignant and benign), and the like.

IX. Kits

The invention includes various kits which comprise a compound, such as a nucleic acid encoding REMODEL, an antibody that specifically binds REMODEL, a nucleic acid complementary to a nucleic acid encoding REMODEL but in an antisense orientation with respect to transcription, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for alleviating a disease mediated by malexpression of REMODEL. The kit is used pursuant to the methods disclosed in the invention. Briefly, the kit may be used to contact a cell with a nucleic acid complementary to a nucleic acid encoding REMODEL where the nucleic acid is in an antisense orientation with respect to transcription to reduce expression of REMODEL, or with an antibody that specifically binds with REMODEL, wherein the decreased expression, amount, or activity of REMODEL mediates an beneficial effect. Moreover, the kit comprises an applicator and an instructional material for the use of the kit. These instructions simply embody the examples provided herein.

The kit includes a pharmaceutically-acceptable carrier. The composition is provided in an appropriate amount as set forth elsewhere herein. Further, the route of administration and the frequency of administration are as previously set forth elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE

The experiments presented in this example may be summarized as follows.

In order to identify novel factors involved in mediating arterial remodeling in response to injury, suppressive subtractive hybridization was performed using mRNA from normal and balloon-injured rat arteries. A novel nucleic acid sequence was identified using this approach and a full length 1235 bp cDNA clone was isolated by screening a cDNA library prepared from 8 day balloon-injured rat carotid arteries and aortae. This cDNA clone comprises an open reading frame (ORF) of about 245 amino acids having no significant homology to any known protein. This protein, referred to herein as REMODEL, was previously termed AIBE for Adventitia Inducible and Bone Expressed protein. REMODEL comprises, inter alia, a potential transmembrane domain and five potential N-myristoylation sites which can target the molecule to the cell membrane.

In situ hybridization analysis disclosed that REMODEL mRNA expression is remarkably restricted to the adventitia of balloon-injured vessels with maximal expression detected at 8 days after carotid artery balloon denudation and with no detectable expression in normal arteries. REMODEL expression in the adventitia was no longer detectable at 6 weeks after balloon injury.

The data disclosed herein further demonstrate that during mouse embryogenesis, REMODEL expression was prominent in developing bone starting at about 12 days post coitus (dpc), while Northern blot analysis demonstrated that only low levels of REMODEL expression were detected in brain and lung of the adult animal.

Injection of REMODEL mRNA into frog embryos caused severe developmental abnormalities, including, but not limited to, inhibition of FGF-induced mesoderm formation, failure of neural tissue cells to migrate, and failure of dorsal closure, abnormal head development, and formation of a split tail.

The Results of the experiments presented in this example are now described.

Identification of Injury Inducible Factor

Suppressive subtractive hybridization was performed between cDNA expressed in normal rat carotid artery/aorta and cDNA expressed in 8 day balloon injured carotid/aorta using the PCR-Select kit from Clontech Laboratories, Inc. (Palo Alto, Calif.), to identify genes that are involved in the arterial remodeling response to injury. The normal vessel provided the "driver" cDNA and the injured vessel provided the "tester" cDNA.

Partial sequences of approximately 300 clones were obtained by automated sequencing and the sequence identities were determined by searching GenBank databases, including non-redundant and EST (expressed sequence tag) databases which are publicly available at http://www.ncbi.nlm.nih.gov/blast/blast.cgi. Those sequences not matching a known gene (usually corresponding murine or human ESTs) were identified in the database and were pursued further.

Duplicate slot blots containing the series of cDNA clones were hybridized with $^{32}$P-dCTP labeled cDNA prepared from either normal vessel RNA or from balloon-injured vessel RNA. The clones that exhibited increased expression in the injured vessels were then further tested using Northern blot technique with RNA from both normal and balloon-injured rat arteries.

The data disclosed herein demonstrate that REMODEL expression was essentially not detectable in normal vessels while injured vessels exhibited a dominant 1.2 kb transcript (FIG. 1B-1). The sequences exhibiting detectable increased expression in the injured vessels compared with normal vessels were further examined for expression in various organs using Northern blot. In order to select for genes that might be specific for the vasculature, those clones that were predominantly expressed in vascular tissues like lung and brain, in addition to showing expression in the aorta or carotid artery, were pursued. The data disclosed herein demonstrate that REMODEL showed low levels of expression in lung and brain (FIG. 1A-1).

Clones identified using the above-described screening approach were then used to make $^{35}$S-UTP labeled sense and antisense strand which were, in turn, used for in situ hybridization on normal and balloon-injured rat carotid artery sections (4, 8, 14, and 28 days after injury), as well as on sections from staged mouse embryos.

To determine expression in quiescent versus proliferating/migrating endothelium, en face preparations of 7 and 14 day injured aortas were also used in the in situ hybridization study as described in Lindner and Reidy (1993, Circ. Res. 73:589–595). In the injured aortae, endothelial regeneration occurs from the intercostal arteries giving rise to migrating/proliferating endothelial cells at the wound edge as well as quiescent endothelium in the monolayer away from the wound edge.

Among the clones exhibiting modulated expression in response to injury, REMODEL was expressed in the adventitia of injured vessels but was absent from normal adventitia (FIGS. 2A and 2B). Strong expression of REMODEL was detected at 8 days after injury with less expression at 14 days (FIGS. 2B and 2C). Surprisingly, there was no appreciable REMODEL expression detected in the media and in the developing neointima despite the fact that Smooth Muscle Cells (SMC) in vitro expressed the 1.2 kb transcript (FIGS. 2B and 2C). No other gene is known in the art which is specifically induced in the adventitia and is not detectably induced in the neointima. Longer exposure or loading of larger amounts of RNA from in vitro SMC also revealed a less abundant transcript of about 3.5 kb (FIG. 1A-1).

At 4 weeks after balloon injury, REMODEL expression was nearly undetectable in the adventitia. At the time when REMODEL is expressed, the adventitia shows rapid proliferation of myofibroblasts as well as a subsequent sharp decline in cell number that is accompanied by abundant synthesis of collagens type I and type III (Smith et al., 1999, Cir. Res. 84:1212–1222). Interestingly, in the staged mouse embryos, REMODEL expression was detected in the mesoderm at 11.5 days post coitus (dpc) (FIG. 2E), which expression later became restricted to the developing bone (FIG. 2F). Lower levels of REMODEL expression were also detected in the cortical bone of a femur from a rat pup. During development expression of REMODEL was prominent in developing bone such as the skull (FIGS. 2F, 2G and 2H). REMODEL continued to be expressed in osteoblasts adjacent to mineralized bone (FIGS. 2I and 2J).

In addition, full thickness skin incisions undergoing wound healing and remodeling revealed strong expression along the incision (FIG. 2L) while no expression was detectable in normal skin (FIG. 2K).

A full length REMODEL clone was obtained using a size-fractionated (500 bp cut-off) cDNA library prepared using mRNA extracted from 8 day balloon-injured rat aortas and carotid arteries using a Lambda Zap Express system (Stratagene, La Jolla, Calif.). After excision with a helper phage, the isolated cDNA clones were ligated into the pBK-CMV vector (Stratagene, La Jolla, Calif.), which allows for convenient expression in mammalian cells using the CMV promoter. This library is expected to contain sequences expressed in proliferating SMC, endothelial cells (EC), and fibroblasts as well as their quiescent counterparts. In addition, sequences from inflammatory cells, predominantly macrophages, are also expected to be present in the library.

The 230 bp REMODEL clone obtained using the differential screen approach was then used to probe the library and six clones were isolated and sequenced. Five clones started within 50 bp upstream of a putative translational AUG start site at nucleotide position 116 (FIG. 4A$i$). The longest clone contained an additional 60 bp of 5' sequence which contained a potential additional in-frame AUG translational start site at position 19 (FIG. 4A$i$). The 230 bp clone was designated REMODEL-short (REMODEL$_S$) and the 290 bp REMODEL clone was designated REMODEL-long (REMODEL$_L$).

Searching The Institute for Genomic Research (TIGR) sequence database for the human homolog of REMODEL, identified a 771 bp of 3' sequence. Using RNA from cultured human aortic SMC, 5' RACE (rapid amplification of cDNA ends) cloning was performed to identify the missing approximately 500 bp sequence located at the 5' end. The sequence alignment of rat (SEQ ID NO:2) and human REMODEL (SEQ ID NO:4) is shown in FIG. 4. Interestingly, the human sequence did not have the additional 5' AUG translational start site but only contained the AUG codon at position 114. A 5' primer located upstream of this AUG start site and a 3' primer were designed to verify that the AUG start site at position 19 of the rat sequence was not a cloning artifact. Reverse transcription polymerase chain reaction (RT-PCR) analysis and sequencing was performed to confirm the presence of the AUG-19 codon. The overall identity between the human and rat REMODEL sequence was 78.3% at the nucleotide level using a blast 2 algorithm search as provided at the web site http://www.ncbi.nlm.nih.gov/gorf/bl2.html, which web site is publicly available. Further, homology between the rat (SEQ ID NO:2) and human REMODEL (SEQ ID NO:4) amino acid sequences is greater than about 97% using the blast 2 algorithm search strategy described previously.

Amino Acid Sequence and Domains Within REMODEL

In vitro translation was performed using a kit (Promega Corp., Madison, Wis.) comprising rabbit reticulocyte lysate and $^{35}$S-methionine. The data disclosed herein demonstrate that REMODEL$_L$ contained two putative transcriptional start sites compatible with the Kozak rule (i.e., at positions 19 and 116) while REMODEL$_S$ had only the AUG$_{16}$ site. In vitro translation revealed that the REMODEL$_L$ construct expressed preferentially the long form but, to a lesser extent, the short form of REMODEL was also expressed from the REMODEL$_L$ construct (FIG. 5A). However, the REMODEL$_S$ construct expressed only the shorter form. The apparent molecular weights of the long and short form were approximately 34 kDa and 30 kDa, respectively (FIG. 5A). Since the human sequence does not have the additional AUG codon at the 5' end, it is most likely that in vivo translation starts at AUG$_{16}$. This is predicted to result in a 245 amino acid (aa) rat protein while the human homolog has about 243 amino acids (SEQ ID NO:4) due to a 2 amino acid deletion in the amino terminus.

A leucine-rich hydrophobic region is located near the amino terminus and, without wishing to be bound by any particular theory, this region is predicted to be a cleavable signal peptide (from about amino acid residue number 1 to amino acid residue 32), which would result in a 213 aa mature peptide having a molecular weight of about 23.1 kDa and a theoretical pI of 6.57 for the human REMODEL. However, if the aa1–aa32 peptide is not a signal sequence and does not get cleaved, it is predicted to be a definitive transmembrane domain. The rat REMODEL$_L$ protein would result in a 277 aa protein which lacks a predicted signal sequence (SEQ ID NO:2).

At the amino acid level, human and rat REMODEL were 95% identical (FIG. 4B). The carboxy terminal half of the molecule was more highly conserved with over 99% identity between the two species. Remarkably, the amino acid composition contains 4.7% cysteine, 2.4% tyrosine, and 2% tryptophan residues. A glycine-rich domain also found in many collagens is located between amino acid residue 59 and amino acid residue 93. A putative N-glycosylation site is located at about amino acid residue 188 to about amino acid residue 191, a putative protein kinase C (PKC) phosphorylation site at amino acid residue 146 to amino acid residue 148, and four casein kinase II (CD2) phosphorylation sites. Furthermore, there are 5 N-myristoylation sites located throughout the molecule. A summary of these putative motifs is depicted in FIG. 3.

Functional Characterization of REMODEL

Contrary to SMC in the vessel wall, cultured rat aortic SMC growing in DMEM supplemented with 10% bovine serum expressed REMODEL mRNA. Expression was inducible by TFG-β in 3T3 cells as well as SMC with peak expression detected after 8 hours of stimulation. Expression levels were still elevated after 24 hours and no induction followed stimulation of cells with FGF-2.

Since REMODEL is also expressed in bone, expression in MC3T3 cells, a bone derived cell line, was also examined. The response to TGF-β stimulation was similar to SMC and NIH3T3 cells with maximal induction occurring after 8 hours (FIG. 1C). Stimulation with bone morphogenetic protein-4 (BMP-4) caused a similar induction of REMODEL mRNA in MC3T3 cells as TGF-β (FIG. 1C).

Antibodies That Specifically Bind REMODEL

The peptide corresponding to the carboxy terminal 15 amino acids of REMODEL was coupled to keyhole limpet hemocyanin (KLH) and used to immunize two rabbits. One of the rabbits produced antiserum that had a titer of greater than about 1:64,000. The antiserum (used at a 1:5000 dilution) detected a specific band with a molecular weight of approximately 30 kDa in lysates prepared from 10 day balloon-injured rat carotid arteries while this band was absent in lysates prepared from normal vessels (FIG. 5C). The same specific band was also detected in lysates from cultured SMC.

In addition, SMC cultured in vitro also expressed a slightly larger immunoreactive band of approximately 34 kDa. However, concentrated conditioned medium obtained from SMC contained no detectable immunoreactivity, indicating that if any REMODEL is secreted, it is at low levels beyond the level of detection. Further, the detectable bands were specific since the preimmune IgG from the same rabbit did not react with these protein bands (FIG. 5C).

Expression of GFP-tagged REMODEL in Transfected Cells

REMODEL cDNA was cloned into a green fluorescent protein (GFP)- and hemagglutinin (HA)-tagged expression vector to produce REMODEL/tag polypeptide fusion proteins. The localization of the GFP-REMODEL fusion protein was then assessed with regard to its cellular localization following transfection of NIH3T3 and 293 cells with the construct encoding the fusion protein. The data disclosed herein demonstrate that fluorescence was distributed homogeneously throughout the cell with absence of GFP in the nucleus. This staining pattern is compatible with cytosolic and/or cell membrane localization. The transfection efficiency obtained using the GFP-REMODEL construct was consistently lower than with the GFP control vector.

Expression of Myc-tagged REMODEL in Transfected Cells

The coding region of rat REMODEL was cloned into a mammalian expression vector comprising a myc tag at the carboxy terminus (pcDNA3.1myc/his, Invitrogen, Carlsbad, Calif.). The sequence of the coding region used in the construct is depicted in FIG. 7 (SEQ ID NO:9).

Transient transfections were performed using bovine aortic endothelial cells (BAE) and NIH3T3 cells. The cell lines were analyzed for transgene expression 24 hours and 48 hours after transfection using Western blotting and immunostaining using an anti-myc monoclonal antibody (Zymed, South San Francisco, Calif.).

Interestingly, the data disclosed herein demonstrate that very little expression remained at 48 hours post-transfection (FIG. 5F). Without wishing to be bound by any particular theory, these data suggest that the transfected cells were lost from the culture. In comparison, the same cell line transfected in parallel with an unrelated cDNA (EP 1) using the same vector exhibited significantly higher levels of expression at 48 hours than at 24 hours (FIG. 5F).

The possibility that overexpression of REMODEL results in cell death was examined further using immunohistochemistry, confocal microscopy and flow cytometry for cell cycle analysis. BAE cells transiently transfected with myc-tagged REMODEL exhibited a 15% increase in accumulation of cells in G0–G1 at 24 hours post-transfection (transfection efficiency approximately 15%). Western blotting of these transfectants using the anti-myc antibody demonstrated that by 48 hours post-transfection very little immunoreactivity remained, indicating that the transfected cells were lost from the culture.

Confocal microscopy of REMODEL transfected NIH3T3 cells demonstrated localization of the myc-tagged protein in very small vesicles distributed throughout the cytoplasm (FIG. 5B).

Vessel wall lysates were prepared from rat carotid arteries harvested at 1, 4, 7, 14, and 28 days after balloon injury. These lysates (30 micrograms of protein in each lane) were analyzed by immunoblotting using an antibody raised against the carboxyterminal peptide of REMODEL. The highest levels of REMODEL were seen at 4 and 7 days after injury with a decline to near control levels at 28 days post injury (FIG. 5C).

Smooth muscle cells in vitro expressed REMODEL mRNA while this cell type showed very little expression in vivo. Therefore expression of REMODEL was examined using a variety of different cell lines using immunoblotting analysis (FIG. 5D). The cell lines included NIH3T3, bovine aortic (BAE), PAC-1 (a rat smooth muscle cell line), A7r5 (a rat smooth muscle cell line), RASMC (rat aortic SMC primary culture), 293, BASMC (bovine aortic SMC), 10T1/2, human umbilical vein endothelial cells (HUVEC), A431, and human aortic SMC (HASMC). The data disclosed herein demonstrate detection of a prominent immunoreactive band with an apparent molecular weight of about 34 kDa that was present in all cell lines tested. These data indicate that the antibody reacted with mouse, rat, bovine, and human homologs of REMODEL (FIG. 5D). A less abundant protein band having an apparent molecular weight of about 30 kDa was present in some cell lines and some additional larger immunoreactive bands were also detected. Without wishing to be bound by any particular theory, the 30 kDa band may reflect differences in glycosylation or phosphorylation of REMODEL.

The regulation of REMODEL expression by TGFβ was further investigated using MC3T3 cells, a bone derived cell line. Immunoblotting of cell lysates harvested after 24, 48, and 72 hours after stimulation with TGF-β demonstrated increased expression levels of REMODEL protein compared to controls (FIG. 5E).

The data disclosed herein demonstrate that blocking signaling via the TGFβ receptor type II by the addition of a soluble TGFβ receptor type II (Biogen, Cambridge, Mass.) to the cells, inhibited expression of REMODEL protein (FIG. 5E). MC3T3 cells were treated with 1 ng/ml of TGF-β1 (TGF-β) or 100 ng/ml soluble TGF-β receptor type II (sol. TGF-βRII), the cells were harvested at various time points, and 30 micrograms of protein were applied to each polyacrylamide gel lane (FIG. 5E). The data disclosed herein demonstrate that TGFβ1 stimulated REMODEL expression while inhibition of TGFβ signaling inhibited REMODEL expression.

Effects of REMODEL Overexpression in *Xenopus laevis*

The biological effects of REMODEL overexpression on *Xenopus laevis* development were studied using injection of REMODEL mRNA into frog embryos. For injection experiments, a dose of 5 ng of either the long form of REMODEL or the short form of REMODEL mRNA was injected into embryos at the 2 cell stage. Controls embryos were injected with an equal volume of empty vehicle or lacZ mRNA.

Injection of both $REMODEL_L$ and $REMODEL_S$ disturbed normal embryonic development. In general, the percentage of oocytes exhibiting disturbed development was significantly higher in the oocytes injected with the short form (close to 100%) while the long form of REMODEL showed fewer malformed embryos. Without wishing to be bound by any particular theory, these data may indicate that the short form of REMODEL is translated into protein in vivo.

In stage 17 embryos, there was a difference between lacZ-injected (FIG. 6A, left 2 embryos) and REMODEL-injected embryos (FIG. 6A, right 2 embryos) indicating inhibition of blastopore closure.

At stage 34, control-injected embryos exhibited normal development (FIG. 6B), however, REMODEL-injected embryos displayed a number of defects (FIG. 6C). The REMODEL-injected embryos were smaller and were often distorted exhibiting abnormal development of the head. Due to failure of closure of the neural folds, fusion of the neurectoderm did not occur (FIG. 6D). Other malformations included development of a split tail (FIG. 6E). Several separate injection experiments were performed with similar results. This phenotype is remarkably similar to that of embryos injected with mRNA for dominant-negative FGF receptor constructs (Neilson and Friesel, 1996, J. Biol. Chem. 271:250497–25057).

The effect of REMODEL on mesoderm induction was further assessed in that REMODEL or control RNA was injected at the 2 cell stage and the embryos were allowed to develop to the blastula stage, at which time the animal pole ectoderm (animal caps) were dissected. Uninjected animal caps incubated in the presence of 200 ng/ml of FGF-1 elongated in a manner consistent with mesoderm induction while control-injected animal caps did not. Animal caps from embryos injected with REMODEL and incubated in the presence of FGF-1 resembled animal caps incubated without FGF-1. This indicates that REMODEL was able to block FGF-induced mesoderm formation.

Further, an important experiment assessed whether secretion of REMODEL is necessary for function as follows. Using PCR, a construct comprising a deletion of the first 32 amino acids that have the potential for being either a cleavable signal peptide or a transmembrane domain, was designed (SEQ ID NO:9, FIG. 7). The construct was cloned into the PCS2+ vector (American Type Culture Collection, Manassas, Va.) and RNA was injected into frog embryos at the 2 cell stage. The resulting phenotype was similar to the one seen in $REMODEL_S$-injected embryos both in severity as well as frequency. Without wishing to be bound by any particular theory, these results suggest that it is likely that REMODEL is not a secreted protein and that the putative N-myristoylation sites can anchor the protein in the cell membrane if required for biological function(s).

Function of REMODEL in MC3T3 Cells

MC3T3 cells were transfected with control vector (pcDNA3.1 myc/his, Invitrogen, Carlsbad, Calif.) or with full length rat REMODEL cDNA in an antisense orientation. Stably transfected clonal cell lines were then obtained and used in cell proliferation assays.

Morphology of the cells was determined using phase contrast microscopy for both vector transfected (FIGS. 8A–C) and antisense REMODEL transfected cells. As depicted in FIGS. 8D–I, antisense REMODEL transfected cells exhibited a distinctly altered phenotype demonstrating less adhesion to the substratum and reduced cell-cell contacts. More specifically, antisense transfected cells were elongated and fibroblastic in appearance (FIGS. 8D–I). This is in contrast to control vector transfected cells, which exhibited a cobblestone morphology (FIGS. 8D–8I).

The data disclosed herein also demonstrate that there were increased numbers of dead cells and cell debris in the antisense transfected cells indicating, without wishing to be bound by any particular theory, increased cell turnover in REMODEL antisense transfected cells.

Increased cell turnover was determined by establishing growth curves of the clones (FIG. 9A) and measuring [$^3$H]-thymidine incorporation in the clones (FIG. 9B) in parallel experiments. Even though cell counts were similar between control and antisense REMODEL transfected cells at all time points, [$^3$H]-thymidine incorporation was significantly higher in the antisense REMODEL transfected cells at all time points examined (FIG. 9B). Increased cell turnover in the antisense transfected cells indicates that cell viability is reduced by shortening the cell life span. Together with the altered adhesion phenotype of the cells, the data suggests, without wishing to be bound by any particular theory, that REMODEL is involved in cell-matrix and cell-cell interaction(s).

Expression of REMODEL in Transgenics

Transgenic mice were generated in which the coding region of REMODEL was under the control of the CMV promoter. Breeding of a REMODEL transgenic female with a REMODEL transgenic male give rise to mouse pups that exhibited hemorrhaging in the hip and shoulder regions. The bleeding appeared to originate from the long bones (FIG. 10A). In one instance bleeding also occurred in smaller bones of the foot. X-ray examination of the skeleton revealed that all transgenic mice were smaller than corresponding non-transgenic mice (FIG. 10B). This was particularly evident in the long bones. Dissection of the dorsal skin revealed protrusion of the spinal cord similar to a phenotype seen in spina bifida disorders (FIG. 10C).

Skeletal preparations of the control and transgenic pups were prepared using standard methods in order to further investigate the skeletal abnormalities. In these preparations (FIGS. 11A–11J) mineralized bone was stained using Alizarin Red (pink color depicted as darker gray) and cartilage is stained using Alcian Blue (blue color depicted as lighter gray). The data disclosed herein demonstrate that there was a striking decrease in cartilage formation affecting all sites of cartilage generation including the extremities, particularly the distal phalanges (FIG. 11A compared with FIG. 11B). Cartilage was completely missing from the vertebra and intervertebral joints in the remodel transgenic mice (FIG. 11D) compared with normal pups (FIG. 11C), leaving the posterior parts of the vertebrae and the intervertebral joints without cartilage.

The absence of cartilage in the posterior parts of the vertebra surrounding the spinal cord is the most likely reason for the protrusion of the spinal cord leading the spina bifida phenotype. The anterior parts of the ribs exhibited strikingly reduced cartilage formation, which was most pronounced in the more caudal ribs (FIG. 11F compared with FIG. 11E).

Another finding was the marked decrease in the density of the mineralized bone which gave the flat bones of the skull a more transparent appearance (compare FIG. 11H with FIG. 11G). Without wishing to be bound by any particular theory, the decreased bone density is expected to result in weaker bones with increased tendency to fracture. Indeed, the hemorrhaging observed in the shoulder and hip regions was found to be the result of fractured long bones such as the humerus (FIGS. 11I and 11J) and femur.

The data disclosed herein using transgenic mice indicate that REMODEL plays an important role in bone growth. Similar to the frog embryo injection experiments wherein REMODEL mRNA mediated a failure of dorsal closure, the mouse transgenics also exhibit spina bifida-like defects of the spinal column.

These findings demonstrate that altered expression of REMODEL is affecting vital mechanisms of bone formation. In particular, increased REMODEL expression inhibits cartilage and bone formation resulting in reduced bone growth and bone mineralization which gives rise to more fragile bones. Furthermore, without wishing to be bound by any particular theory, the data disclosed herein suggest that inhibition of REMODEL expression can lead to the opposite phenotype with increased cartilage formation and increased bone density and strength. The level of REMODEL expression could thus be a predictor of bone formation, bone density and bone strength. Further, inhibiting REMODEL expression may be useful for diseases, disorders, or conditions associated with decreased bone density, bone formation and bone strength such as, but not limited, osteoporosis, and the like.

The data disclosed herein demonstrate that REMODEL is expressed selectively in settings where remodeling occurs, i.e., skin incisional wounds, bone, and the like. Without wishing to be bound by any particular theory, these data suggest that the role of REMODEL is not restricted to the vasculature but instead REMODEL expression is be relevant to events in wound healing in general, including bone formation, bone density and bone strength.

Wound healing is characterized by the formation of granulation tissue from connective tissue surrounding the damaged area and its components are inflammatory cells, fibroblasts and myofibroblasts (smooth muscle α-actin positive). As the wound closes and evolves into a scar, there is an important decrease in cellularity and a specific disappearance of myofibroblasts (Desmouliere et al., 1997, Int. J. Biochem. Cell. Biol. 29:19–30; Desmouliere et al., 1995, Am. J. Pathol. 146:56–66). This cell loss has been shown to occur by apoptosis (Desmouliere et al., 1995, Am. J. Pathol. 146:56–66). Failure to decrease this cellularity may contribute to hypertrophic scarring and keloid formation (Chipev et al., 2000, Cell Death Differ. 7:166–176; Messadi et al., 1999, Wound Repair Regen. 7:511–517). The response of the adventitia to balloon injury (Smith et al., 1999, Circ. Res. 84:1212–1222) and the response of the myocardium to infarction are very similar (Takemura et al., 1998, Circ. Res. 82: 1130–1138; Takemura et al., 1998, Circ. Res. 82:1231–1233) with early accumulation of myofibroblasts and subsequent loss of cells by apoptosis as disclosed elsewhere herein resulting in an acellular matrix-rich structure. It should be emphasized that, as demonstrated by data disclosed elsewhere herein, REMODEL is induced in these myofibroblasts while it is not expressed in the dedifferentiated smooth muscle cells (SMC) of the neointima. While smooth muscle α-actin is down-regulated in the dedifferentiated, proliferating SMC of the neointima, it is induced in the myofibroblasts of the adventitia (Smith et al., 1999, Circ. Res. 84:1212–1222) but is lost from the adventitial cells within 2 weeks after injury.

REMODEL expression may play a role in other clinically relevant situations of fibrosis, including liver fibrosis and pulmonary fibrosis. In liver fibrosis, apoptosis of hepatic stellate cells has been implicated in the fibrotic process and targeting apoptosis may be promising strategy for antifibrotic therapies (Cales et al., 1998, Biomed. Pharmacother. 52:259–263). TGFβ has been identified as the major factor responsible for fibrosis in the bleomycin-induced lung fibrosis model (Wang et al., 1999, Thorax 54:805–812). Finally, since REMODEL is expressed in developing bone it should be mentioned that apoptosis is an integral part of endochondral ossification and bone fracture healing with chondrocytes and osteoblasts undergoing apoptosis (Einhom et al., 1998, Clin. Orthop. S7–21; Olmedo et al., 1999, J. Orthop. Trauma 13:356–362). The prominent expression of REMODEL in developing bone further suggests, without wishing to be bound by any particular theory, that REMODEL is involved in regulating calcification since inhibition of calcification is an important event in cell death (Kim, 1995, Scanning Microsc. 9:1137–1178; Kockx et al, 1998, Arterioscler. Thromb. Vasc. Biol. 18:1519–1522).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a human REMODEL, wherein the sequence of said nucleic acid consists of SEQ ID NO:3.

2. An isolated chimeric nucleic acid, said chimeric nucleic acid comprising a nucleic acid encoding a tag polypeptide covalently linked to a nucleic acid encoding a human REMODEL, wherein said nucleic acid encoding said human REMODEL consists of the nucleic acid sequence of SEQ ID NO:3.

3. The nucleic acid of claim 2, wherein said tag polypeptide is selected from the group consisting of a green fluorescent protein tag polypeptide, an influenza virus hemagglutinin tag polypeptide, a myc tag polypeptide, a glutathione-S-transferase tag polypeptide, a myc-pyruvate kinase tag polypeptide, a His6 tag polypeptide, a FLAG tag polypeptide, and a maltose binding protein tag polypeptide.

4. A vector comprising the nucleic acid of claim 1.

5. The vector of claim 4, said vector further comprising a promoter/regulatory nucleic acid sequence operably linked thereto.

6. A recombinant cell comprising the isolated nucleic acid of claim 1.

7. A recombinant cell comprising the vector of claim 4.

8. An isolated nucleic acid encoding a human REMODEL, wherein the sequence of said isolated nucleic acid consists of a nucleic acid complementary with a nucleic acid consisting of the sequence of SEQ ID NO:3.

9. A recombinant cell comprising the isolated nucleic acid of claim 8.

10. A composition comprising the isolated nucleic acid of claim 8 and a pharmaceutically-acceptable carrier.

11. A composition comprising the isolated nucleic acid of claim 1 and a pharmaceutically-acceptable carrier.

* * * * *

UNITED STATES PATENT AND TRADEMARK OFFICE
CERTIFICATE OF CORRECTION

PATENT NO. : 6,630,325 B1
DATED : October 7, 2003
INVENTOR(S) : Volkhard Lindner and Robert E. Friesel It is certified that error appears in the above-identified patent and that said Letters Patent is hereby corrected as shown below:

Column 1,
Line 5, insert;
-- STATEMENT REGARDING FEDERALLY SPONSORED RESEARCH OR DEVELOPMENT
This invention was supported in part by US Government funds (National Institutes of Health Grant No. RR15555), and the US Government may therefore have certain rights in the invention. --

Signed and Sealed this

Fourteenth Day of June, 2005

JON W. DUDAS
*Director of the United States Patent and Trademark Office*

SEQUENCE LISTING

<160> NUMBER OF SEQ ID NOS: 9

<210> SEQ ID NO 1
<211> LENGTH: 1192
<212> TYPE: DNA
<213> ORGANISM: Rattus sp.

<400> SEQUENCE: 1

-continued

| | |
|---|---|
| atgcggccgg ccgcagagct gggccagacg ctgagcaggg ccgggctctg ccgacccctt | 60 |
| tgcctcctgc tctgcgcttc gcagctaccg cacacgatgc accccaagg ccgcgccgcc | 120 |
| tccccacagc tgctgctcgg cctcttcctt gtgctactgc tgcttctgca gctgtccgcg | 180 |
| ccgtccagcg cctctgagaa tcccaaggtg aagcaaaaag cgctgatccg cagagggaa | 240 |
| gtggtagacc tgtataatgg gatgtgccta caaggaccag caggagttcc tggtcgcgat | 300 |
| gggagccctg gggccaatgg cattcctggc acaccgggaa tcccaggtcg ggatggattc | 360 |
| aaaggagaga aaggggagtg cttaagggaa agctttgagg aatcctggac cccaaactac | 420 |
| aagcagtgtt catggagttc acttaattat ggcatagatc ttgggaaaat tgcggaatgt | 480 |
| acattcacaa agatgcgatc caacagcgct cttcgagttc tgttcagtgg ctcgcttcgg | 540 |
| ctcaaatgca ggaatgcttg ctgtcaacgc tggtatttta cctttaatgg agctgaatgt | 600 |
| tcaggacctc ttcccattga agctatcatc tatctggacc aaggaagccc tgagttaaat | 660 |
| tcaactatta atattcatcg tacttcctcc gtggaaggac tctgtgaagg gattggtgct | 720 |
| ggactggtag acgtggccat ctgggtcggc acctgttcag attacccccaa aggagacgct | 780 |
| tctactgggt ggaattctgt gtcccgcatc atcattgaag aactaccaaa ataaagcccc | 840 |
| tgaaggtttc attccctgcc tcatttactt gttaaatcaa gcctctggat gggtcattta | 900 |
| aatgacattt cagaagtcac ttatgtgctc agccaaatga aaaagcaaag ttaaatacgt | 960 |
| ttacagacca aagtgtgatc tcacacttta agatctagca ttatccattt tatttcaacc | 1020 |
| aaagatggtt tcaggatttt atttctcatt gattactttt tgagcctata taccggaatg | 1080 |
| ctgttatagt ctttaatatt tcctactgtt gacattttga aacatataaa agttatgtct | 1140 |
| ttgtaagagc tgtatagaat tattttatat gttaaataaa tgcttcaaac aa | 1192 |

<210> SEQ ID NO 2
<211> LENGTH: 245
<212> TYPE: PRT
<213> ORGANISM: Rattus sp.

<400> SEQUENCE: 2

Met His Pro Gln Gly Arg Ala Ala Ser Pro Gln Leu Leu Gly Leu
 1               5                  10                  15

Phe Leu Val Leu Leu Leu Leu Gln Leu Ser Ala Pro Ser Ser Ala
                20                  25                  30

Ser Glu Asn Pro Lys Val Lys Gln Lys Ala Leu Ile Arg Gln Arg Glu
             35                  40                  45

Val Val Asp Leu Tyr Asn Gly Met Cys Leu Gln Gly Pro Ala Gly Val
         50                  55                  60

Pro Gly Arg Asp Gly Ser Pro Gly Ala Asn Gly Ile Pro Gly Thr Pro
 65                  70                  75                  80

Gly Ile Pro Gly Arg Asp Gly Phe Lys Gly Glu Lys Gly Glu Cys Leu
                 85                  90                  95

Arg Glu Ser Phe Glu Glu Ser Trp Thr Pro Asn Tyr Lys Gln Cys Ser
            100                 105                 110

Trp Ser Ser Leu Asn Tyr Gly Ile Asp Leu Gly Lys Ile Ala Glu Cys
        115                 120                 125

Thr Phe Thr Lys Met Arg Ser Asn Ser Ala Leu Arg Val Leu Phe Ser
    130                 135                 140

Gly Ser Leu Arg Leu Lys Cys Arg Asn Ala Cys Cys Gln Arg Trp Tyr
145                 150                 155                 160

Phe Thr Phe Asn Gly Ala Glu Cys Ser Gly Pro Leu Pro Ile Glu Ala

```
                165                 170                 175
Ile Ile Tyr Leu Asp Gln Gly Ser Pro Glu Leu Asn Ser Thr Ile Asn
                    180                 185                 190

Ile His Arg Thr Ser Ser Val Glu Gly Leu Cys Glu Gly Ile Gly Ala
            195                 200                 205

Gly Leu Val Asp Val Ala Ile Trp Val Gly Thr Cys Ser Asp Tyr Pro
210                 215                 220

Lys Gly Asp Ala Ser Thr Gly Trp Asn Ser Val Ser Arg Ile Ile Ile
225                 230                 235                 240

Glu Glu Leu Pro Lys
                245

<210> SEQ ID NO 3
<211> LENGTH: 1220
<212> TYPE: DNA
<213> ORGANISM: Homo sapiens

<400> SEQUENCE: 3
acgagggcgg cctcggagcg cggcggagcc agacgctgac cacgttcctc tcctcggtct    60
cctccgcctc cagctccgcg ctgcccggca gccgggagcc atgcgacccc agggccccgc   120
cgcctccccg cagcggctcc gcggcctcct gctgctcctg ctgctgcagc tgcccgcgcc   180
gtcgagcgcc tctgagatcc ccaaggggaa gcaaaaggcg cagctccggc agagggaggt   240
ggtggacctg tataatggaa tgtgcttaca agggccagca ggagtgcctg gtcgagacgg   300
gagccctggg gccaatggca ttccgggtac acctgggatc ccaggtcggg atggattcaa   360
aggagaaaag ggggaatgtc tgagggaaag ctttgaggag tcctggacac ccaactacaa   420
gcagtgttca tggagttcat tgaattatgg catagatctt gggaaaattg cggagtgtac   480
atttacaaag atgcgttcaa atagtgctct aagagttttg ttcagtggct cacttcggct   540
aaaatgcaga aatgcatgct gtcagcgttg gtatttcaca ttcaatggag ctgaatgttc   600
aggacctctt cccattgaag ctataaattta tttggaccaa ggaagccctg aaatgaattc   660
aacaattaat attcatcgca cttcttctgt ggaaggactt tgtgaaggaa ttggtgctgg   720
attagtggat gttgctatct gggttggcac ttgttcagat tacccaaaag gagatgcttc   780
tactggatgg aattcagttt ctcgcatcat tattgaagaa ctaccaaaat aaatgcttta   840
attttcattt gctacctctt tttttattat gccttggaat ggttcactta aatgacattt   900
taaataagtt tatgtataca tctgaatgaa aagcaaagct aaatatgttt acagaccaaa   960
gtgtgatttc acactgtttt taaatctagc attattcatt ttgcttcaat caaaagtggt  1020
ttcaatattt ttttagttgg ttagaatact ttcttcatag tcacattctc tcaacctata  1080
atttggaata ttgttgtggt cttttgtttt ttctcttagt atagcatttt taaaaaaata  1140
taaaagctac caatctttgt acaatttgta aatgttaaga atttttttta tatctgttaa  1200
ataaaaatta tttccaacaa                                              1220

<210> SEQ ID NO 4
<211> LENGTH: 243
<212> TYPE: PRT
<213> ORGANISM: Homo sapiens

<400> SEQUENCE: 4

Met Arg Pro Gln Gly Pro Ala Ala Ser Pro Gln Arg Leu Arg Gly Leu
 1               5                  10                  15

Leu Leu Leu Leu Leu Leu Gln Leu Pro Ala Pro Ser Ser Ala Ser Glu
```

```
                    20                  25                  30
Ile Pro Lys Gly Lys Gln Lys Ala Gln Leu Arg Gln Arg Glu Val Val
            35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Gly Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys

<210> SEQ ID NO 5
<211> LENGTH: 277
<212> TYPE: PRT
<213> ORGANISM: Rattus sp.
<400> SEQUENCE: 5

Met Arg Pro Ala Ala Glu Leu Gly Gln Thr Leu Ser Arg Ala Gly Leu
1               5                   10                  15

Cys Arg Pro Leu Cys Leu Leu Leu Cys Ala Ser Gln Leu Pro His Thr
            20                  25                  30

Met His Pro Gln Gly Arg Ala Ala Ser Pro Gln Leu Leu Leu Gly Leu
        35                  40                  45

Phe Leu Val Leu Leu Leu Leu Gln Leu Ser Ala Pro Ser Ser Ser Ala
    50                  55                  60

Ser Glu Asn Pro Lys Val Lys Gln Lys Ala Leu Ile Arg Gln Arg Glu
65                  70                  75                  80

Val Val Asp Leu Tyr Asn Gly Met Cys Leu Gln Gly Pro Ala Gly Val
                85                  90                  95

Pro Gly Arg Asp Gly Ser Pro Gly Ala Asn Gly Ile Pro Gly Thr Pro
            100                 105                 110

Gly Ile Pro Gly Arg Asp Gly Phe Lys Gly Glu Lys Gly Glu Cys Leu
        115                 120                 125

Arg Glu Ser Phe Glu Glu Ser Trp Thr Pro Asn Tyr Lys Gln Cys Ser
    130                 135                 140

Trp Ser Ser Leu Asn Tyr Gly Ile Asp Leu Gly Lys Ile Ala Glu Cys
145                 150                 155                 160
```

```
Thr Phe Thr Lys Met Arg Ser Asn Ser Ala Leu Arg Val Leu Phe Ser
                165                 170                 175
Gly Ser Leu Arg Leu Lys Cys Arg Asn Ala Cys Cys Gln Arg Trp Tyr
            180                 185                 190
Phe Thr Phe Asn Gly Ala Glu Cys Ser Gly Pro Leu Pro Ile Glu Ala
        195                 200                 205
Ile Ile Tyr Leu Asp Gln Gly Ser Pro Glu Leu Asn Ser Thr Ile Asn
    210                 215                 220
Ile His Arg Thr Ser Ser Val Glu Gly Leu Cys Glu Gly Ile Gly Ala
225                 230                 235                 240
Gly Leu Val Asp Val Ala Ile Trp Val Gly Thr Cys Ser Asp Tyr Pro
                245                 250                 255
Lys Gly Asp Ala Ser Thr Gly Trp Asn Ser Val Ser Arg Ile Ile Ile
                260                 265                 270
Glu Glu Leu Pro Lys
        275
```

<210> SEQ ID NO 6
<211> LENGTH: 403
<212> TYPE: RNA
<213> ORGANISM: Artificial Sequence
<220> FEATURE:
<223> OTHER INFORMATION: Description of Artificial Sequence:REMODEL
      antisense ribonucleoprobe

<400> SEQUENCE: 6

```
ccacccagua gaagcgucuc cuuuggggua aucugaacag gugccgaccc agauggccac    60
gucuaccagu ccagcaccaa ucccuucaca gaguccuucc acggaggaag uacgaugaau   120
auuaauaguu gaauuuaacu cagggcuucc uugguccaga uagaugauag cuucaauggg   180
aagagguccu gaacauucag cuccauuaaa gguaaaauac cagcguugac agcaagcauu   240
ccugcauuug agccgaagcg agccacugaa cagaaucuga agagcgcugu uggaucgcau   300
cuuugugaau guacauuccg caauuuuccc aagaucuaug ccauaauuaa gugaaccuca   360
ugaacacugc uuguaguuug ggguccagga uuccucaaag cuu                     403
```

<210> SEQ ID NO 7
<211> LENGTH: 15
<212> TYPE: PRT
<213> ORGANISM: Artificial Sequence
<220> FEATURE:
<223> OTHER INFORMATION: Description of Artificial
      Sequence:carboxy-terminal amino acids of REMODEL

<400> SEQUENCE: 7

```
Gly Trp Asn Ser Val Ser Arg Ile Ile Ile Glu Glu Leu Pro Lys
 1               5                  10                  15
```

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence:insulin
      signal peptide

<400> SEQUENCE: 8

```
Met Ala Leu Leu Val His Phe Leu Pro Leu Leu Ala Leu Leu Ala Leu
 1               5                  10                  15
Trp Glu Pro Lys Pro Thr Gln Ala
```

```
<210> SEQ ID NO 9
<211> LENGTH: 734
<212> TYPE: DNA
<213> ORGANISM: Artificial Sequence
<220> FEATURE:
<223> OTHER INFORMATION: Description of Artificial Sequence:myc-tagged
      REMODEL construct

<400> SEQUENCE: 9
atggccccca aggccgcgcc gcctccccac agctgctgct cggcctcttc cttgtgctac        60
tgctgcttct gcagctgtcc gcgccgtcca gcgcctctga gaatcccaag gtgaagcaaa       120
aagcgctgat ccggcagagg gaagtggtag acctgtataa tgggatgtgc ctacaaggac       180
cagcaggagt tcctggtcgc gatgggagcc ctggggccaa tggcattcct ggcacaccgg       240
gaatcccagg tcgggatgga ttcaaaggag agaaagggga gtgcttaagg gaaagctttg       300
aggaatcctg gaccccaaac tacaagcagt gttcatggag ttcacttaat tatggcatag       360
atcttgggaa aattgcggaa tgtacattca caaagatgcg atccaacagc gctcttcgag       420
ttctgttcag tggctcgctt cggctcaaat gcaggaatgc ttgctgtcaa cgctggtatt       480
ttacctttaa tggagctgaa tgttcaggac ctcttcccat tgaagctatc atctatctgg       540
accaaggaag ccctgagtta aattcaacta ttaatattca tcgtacttcc tccgtggaag       600
gactctgtga agggattggt gctggactgg tagacgtggc catctgggtc ggcacctgtt       660
cagattaccc caaaggagac gcttctactg ggtggaattc tgtgtcccgc atcatcattg       720
aagaactacc aaaa                                                        734
```